(12) United States Patent
Canney et al.

(10) Patent No.: US 10,544,117 B2
(45) Date of Patent: *Jan. 28, 2020

(54) 5-HYDROXYTRYPTAMINE RECEPTOR 7 ACTIVITY MODULATORS AND THEIR METHOD OF USE

(71) Applicant: Temple University—Of the Commonwealth System of Higher Education, Philadelphia, PA (US)

(72) Inventors: Daniel J. Canney, Ambler, PA (US); Benjamin E. Blass, Philadelphia, PA (US); Rong Gao, Eugene, OR (US); Magid Abou-Gharbia, Exton, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/510,152

(22) PCT Filed: Sep. 10, 2015

(86) PCT No.: PCT/US2015/049303
§ 371 (c)(1),
(2) Date: Mar. 9, 2017

(87) PCT Pub. No.: WO2016/040554
PCT Pub. Date: Mar. 17, 2016

(65) Prior Publication Data
US 2017/0298037 A1    Oct. 19, 2017

Related U.S. Application Data

(60) Provisional application No. 62/048,476, filed on Sep. 10, 2014.

(51) Int. Cl.
*C07D 405/12* (2006.01)
*A61K 31/496* (2006.01)
*C07D 307/33* (2006.01)
*C07D 307/94* (2006.01)
*C07D 405/06* (2006.01)

(52) U.S. Cl.
CPC ......... *C07D 307/33* (2013.01); *C07D 307/94* (2013.01); *C07D 405/06* (2013.01); *C07D 405/12* (2013.01)

(58) Field of Classification Search
CPC .................................................. C07D 405/12
See application file for complete search history.

(56) References Cited

U.S. PATENT DOCUMENTS

| | | | |
|---|---|---|---|
| 5,977,116 A | 2/1999 | Pineiro et al. | |
| 9,802,924 B2 * | 10/2017 | Canney | C07D 405/12 |
| 2004/0229874 A1 | 11/2004 | Bright et al. | |
| 2009/0170824 A1 | 7/2009 | Piniero et al. | |
| 2009/0203676 A1 | 8/2009 | Barba et al. | |
| 2010/0069390 A1 | 3/2010 | Breder | |
| 2010/0197700 A1 | 8/2010 | Badescu et al. | |
| 2012/0208823 A1 | 8/2012 | Hauel et al. | |
| 2013/0252181 A1 | 9/2013 | Momose et al. | |
| 2014/0315801 A1 | 10/2014 | Raeppel et al. | |
| 2015/0291539 A1 | 10/2015 | Canney et al. | |
| 2015/0336962 A1 | 11/2015 | Zak et al. | |
| 2016/0185785 A1 | 6/2016 | Ioannidis et al. | |
| 2016/0303084 A1 | 10/2016 | Chen et al. | |
| 2017/0298037 A1 | 10/2017 | Canney et al. | |
| 2018/0016261 A1 * | 1/2018 | Canney | C07D 307/33 |
| 2018/0016262 A1 * | 1/2018 | Canney | C07D 307/33 |

FOREIGN PATENT DOCUMENTS

EP    1875899    1/2008

OTHER PUBLICATIONS

Burger's Medicinal Chemistry,edited by Manfred E. Wolff, 5th Ed. Part 1, pp. 975-977 (1995).*
Banker et al. "Modern Pharmaceutics", 3rd Ed. p. 596 (1996).*
Gao et al. Med Chem Res (2014) 23:1023-1030.*
Bhandure et al. Med Chem Res (2011) 20:558-565.*
Kaiser et al. J.Med. Chem. vol. 35, 4415-4424 (1992).*
Wagner et al. Pol. J. Pharmacol. vol. 29, pp. 565-569. (Year: 1977).*
Gouault et al. Tetrahedron Letters vol. 41, pp. 7293-7297. (Year: 2000).*
Pytliak et al., "Serotonin receptors—from molecular biology to clinical applications," 2011, Physiol. Res, 60:15-25.
Chen et al., 2011, "Rational Drug Design Leading to the Identification of a Potent 5-HT2C Agonist Lacking 5-HT2B Activity," ACS Medicinal Chemistry Letters 2:929-932.
Vanhoenacker et. al., 2000, "5-HT7 receptors: current knowledge and future prospects," Trends in Pharmacological Sciences 21:70-77.
Hedlund et al., 2004, "Functional, molecular and pharmacological advances in 5-HT7 receptor research," Trends in Pharmacological Sciences 25:481-486.
Cowen and Lucki, 2011, "Serotonin revisited," Psychopharmacology 213:167-169.

(Continued)

*Primary Examiner* — Emily A Bernhardt
(74) *Attorney, Agent, or Firm* — Proskauer Rose LLP; Fangli Chen

(57) ABSTRACT

Pharmaceutical compositions of the invention comprise functionalized lactone derivatives of formula (I)

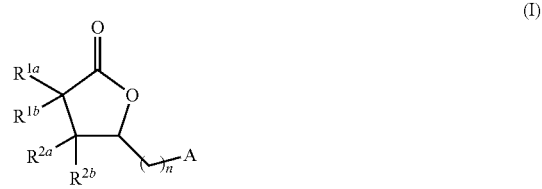

having a disease-modifying action in the treatment of diseases associated with dysregulation of 5-hydroxytryptamine receptor 7 activity.

2 Claims, No Drawings

(56) References Cited

OTHER PUBLICATIONS

Martin et al., "The effects of morphine- and nalorphine-like drugs int he nondependent and morphine-dependent chronic spinal dog", J. Pharmacol. Exp. Ther., 1976, 197:517-532.
Matsumoto, "Sigma Receptors: Historical Perspective and Background", In Sigma Receptors: Chemistry, Cell Biology and Clinical Implications; Matsumoto, R. R., Bowen, W. D., Su, T.-P., Eds; Springer Science: New York, NY, 2007, pp. 1-23.
Collier et al., "Imaging sigma receptors: applications in drug development", Curr. Pharm. Des., 2007, 13:51-72.
Hellewell et al., "A sigma-like binding site in rat pheochromocytoma (PC12) cells: decreased affinity for (+)- benzomorphans and lower molecular weight suggest a different sigma receptor form from that of guinea pig brain", Brain Res., 1990, 527:244-253.
Xu et al., "Identification of the PGRMC1 protein complex as the putative sigma-2 receptor binding site", Nat. Commun., 2011, 2, 380.
Izzo et al., "Alzheimer's therapeutics targeting amyloid Beta 1-42 oligomers I: Abeta 42 oligomer binding to specific neuronal receptors is displaced by drug candidates that improve cognitive deficits", PLoS One, 2014, 9:e111898.
Izzo et al., "Alzheimer's therapetuics targeting amyloid Beta 1-42 oligomers II: Sigma-2/PGRMC1 receptors mediate Abeta 42 oligomer binding and synaptotoxicity", PLoS One, 2014, 9:e111899.
PubChem Substance Record for SID 80872463, Create Date: Jun. 13, 2009.
Guo et al., "Sigma-2 Receptor ligands: Neurobiological effects", Current Medicinal Chemistry, 2015, 22:989-1003.
Skuza, "Pharmacology of sigma (σ) receptor ligands from a behavioral perspective", Current Pharmaceutical Design, 2012, 18:863-874.
Bhandare and Canney, 2014, "Bioisosteric Replacement and Related Analogs in the Design, Synthesis and Evaluation of Ligands for Muscarinic Acetylcholine Receptors," Med. Chem. 10:361-375.
Guseva et al., 2014, "Cellular mechanisms of the 5-HT7 receptor-mediated signaling," Frontiers in Behavioral Neuroscience 8:1-8.
Abbas et al., 2009, "Amisulpride is a potent 5-HT7 antagonist: relevance for antidepressant actions in vivo," Psychopharmacology 205:119-128.
Stanton et al., 1993, "Antagonism of the five cloned human muscarinic cholinergic receptors expressed in CHO-K1 cells by antidepressants and antihistaminics," Biochem. Pharmacology 45:2352-2354.
Kruse et al., 2014, "Muscarinic acetylcholine receptors: novel opportunities for drug development," Nat. Rev. 13:549-560.
Suckling et al., 2007, "M4 agonists/5HT7 antagonists with potential as antischizophrenic drugs: Serominic compounds," Bio. Med. Chem. Lett. 17:2649-2655.
Shen et al., 1993, "Molecular Cloning and Expression of a 5-Hydroxytryptamine7 Serotonin Receptor Subtype," J. Biol. Chem. 268:18200-18204.

* cited by examiner

5-HYDROXYTRYPTAMINE RECEPTOR 7 ACTIVITY MODULATORS AND THEIR METHOD OF USE

CROSS-REFERENCE TO RELATED APPLICATIONS

This application is the U.S. National Stage Application filed under 35 U.S.C. § 371 of International Patent Application No. PCT/US15/49303, filed Sep. 10, 2015, which claims priority to U.S. Patent Application Ser. No. 62/048,476, filed Sep. 10, 2014, the entire contents of which are incorporated herein by reference in their entireties.

STATEMENT OF FEDERALLY FUNDED RESEARCH

The U.S. Government has a paid-up license in this invention and the right in limited circumstances to require the patent owner to license others on reasonable terms as provided for by the terms of grant number HHSN-271-2008-00025-C awarded by the National Institute of Mental Health.

FIELD OF INVENTION

Embodiments of the invention are directed to novel compounds useful as modulators of 5-hydroxytryptamine receptor 7 (5-HT7) activity and their method of use. Embodiments are further directed to a novel chemotype useful for the treatment diseases that are associated with dysregulation of 5-hydroxytryptamine receptor 7 activity.

BACKGROUND OF THE INVENTION methylnin was discovered in the late 1940s and is present in both the peripheral and central nervous systems [Physiol. Res, 60 (2011) 15-25; Psychopharmacology 213 (2011) 167-169]. Serotonin or 5-hydroxytryptamine (5-HT) is a monoamine neurotransmitter of the indolalkylamine group that acts at synapses of nerve cells. Seven distinct families of serotonin receptors have been identified and at least 20 subpopulations have been cloned on the basis of sequence similarity, signal transduction coupling and pharmacological characteristics. The seven families of 5-HT receptor are named 5-HT$_1$, 5-HT$_2$, 5-HT$_3$, 5-HT$_4$, 5-HT$_5$, 5-HT$_6$, and 5-HT$_7$ and each of these receptors in turn has subfamilies or subpopulations. The signal transduction mechanism for all seven families have been studied and it is known that activation of 5-HT$_1$ and 5-HT$_5$ receptors causes a decrease in intracellular cAMP whereas activation of 5-HT$_2$, 5-HT$_3$, 5-HT$_4$, 5-HT$_6$, and 5-HT$_7$ results in an increase in intracellular IP3 and DAG. The 5-HT pathways in the brain are important targets for drug development in the area of CNS disorders. The neurotransmitter binds to its a G-protein coupled receptor and is involved in a wide variety of actions including cognition, mood, anxiety, attention, appetite, cardiovascular function, vasoconstriction, and sleep among others [ACS Medicinal Chemistry Letters 2 (2011) 929-932; Physiol. Res, 60 (2011) 15-25].

BRIEF SUMMARY OF THE INVENTION

The present invention is directed toward novel 5-hydroxytryptamine receptor 7 (5-HT$_7$) activity modulators, compounds of formula (I),

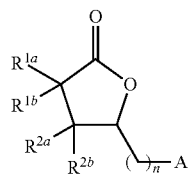

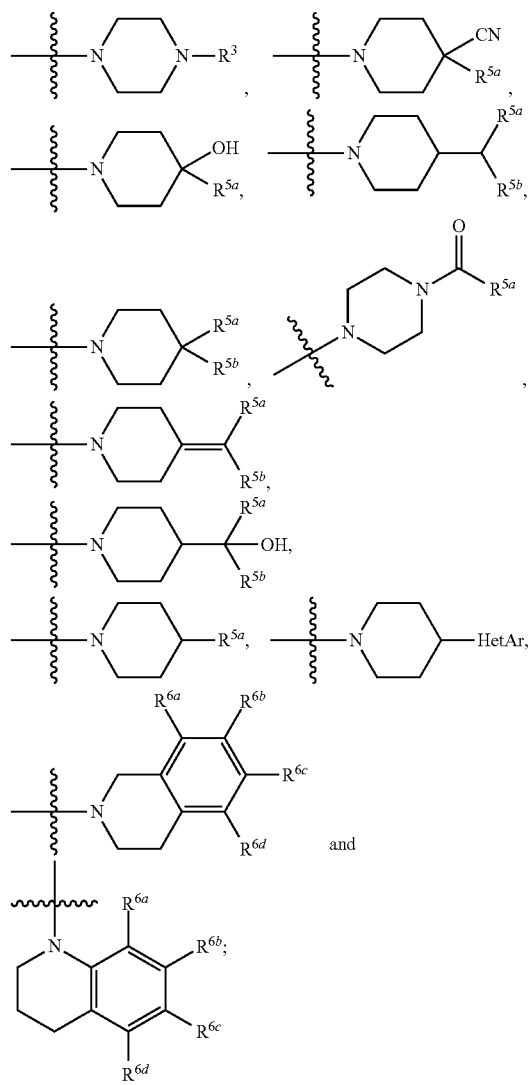

Including hydrates, solvates, pharmaceutically acceptable salts, prodrugs and complexes thereof, wherein:
A is selected from a group consisting of $R^{1a}$ and $R^{1b}$ are independently selected from a group consisting of hydrogen, $C_{1-6}$ linear alkyl, $C_{1-6}$ branched alkyl, and optionally substituted aryl, or $R^{1a}$ and $R^{1b}$ are taken together with the atom to which they are bound to form a ring having from 3 to 7 ring atoms;
$R^{2a}$ and $R^{2b}$ are independently selected from a group consisting of hydrogen, $C_{1-6}$ linear alkyl, $C_{1-6}$ branched alkyl, and optionally substituted aryl, or $R^{2a}$ and $R^{2b}$ are taken together with the atom to which they are bound to form a ring having from 3 to 7 ring atoms;

$R^3$ is selected from a group consisting of $C_{1-6}$ linear alkyl, $C_{1-6}$ branched alkyl, $C_{3-7}$ cycloalkyl, optionally substituted aryl, optionally substituted heteroaryl,

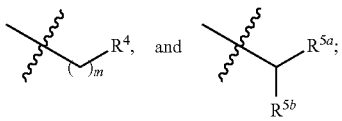

$R^4$ is optionally substituted aryl;
$R^{5a}$ and $R^{5b}$ are each independently optionally substituted aryl;
$R^{6a}$, $R^{6b}$, $R^{6c}$, and $R^{6d}$ are each independently selected from a group consisting of hydrogen, halogen, OH, $C_{1-6}$ linear alkyl, $C_{1-6}$ branched alkyl, $C_{1-6}$ alkoxy, $C_{1-6}$ haloalkyl, $C_{1-6}$ haloalkoxy, cyano, $NH(C_{1-6}$ alkyl), $N(C_{1-6}$ alkyl$)_2$, NHC(O)$R^7$, C(O)NHR$^7$, C(O)N(R$^7)_2$, SH, SC$_{1-6}$ alkyl, SO$^2$NH$_2$, SO$_2$NHR$^7$, SO$_2$R$^7$, and NHSO$_2$R$^7$;
$R^7$ is independently selected at each occurrence from a group consisting of $C_{1-6}$ linear alkyl, $C_{1-6}$ branched alkyl, and $C_{3-7}$ cycloalkyl;
HetAr is optionally substituted heteroaryl:
n is 1, 2, or 3;
m is 1 or 2;

The present invention further relates to compositions comprising:
an effective amount of one or more compounds according to the present invention and an excipient.

The present invention also relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, said method comprising administering to a subject an effective amount of a compound or composition according to the present invention.

The present invention yet further relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, wherein said method comprises administering to a subject a composition comprising an effective amount of one or more compounds according to the present invention and an excipient.

The present invention also relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, and diseases that involve dysregulation of 5-hydroxytryptamine receptor 7 activity. Said methods comprise administering to a subject an effective amount of a compound or composition according to the present invention.

The present invention yet further relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, and diseases that involve dysregulation of 5-hydroxytryptamine receptor 7 activity, wherein said method comprises administering to a subject a composition comprising an effective amount of one or more compounds according to the present invention and an excipient.

The present invention also relates to a method for treating or preventing diseases or conditions associated with dysregulation of 5-hydroxytryptamine receptor 7 activity. Said methods comprise administering to a subject an effective amount of a compound or composition according to the present invention.

The present invention yet further relates to a method for treating or preventing diseases or conditions associated with dysregulation of 5-hydroxytryptamine receptor 7 activity, wherein said method comprises administering to a subject a composition comprising an effective amount of one or more compounds according to the present invention and an excipient.

The present invention further relates to a process for preparing the 5-hydroxytryptamine receptor 7 activity modulators of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

There is evidence that suggests a role for the 5-HT7 receptor in a number of medical disorders. 5-HT7 receptor activity modulators are likely to have a beneficial effect on patients suffering from these disorders. The disorders in which 5-HT7 dysregulation plays a role and modulation of 5-HT7 receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et. al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, and bipolar disorder (WO20040229874).

There is a long felt need for new 5-HT7 modulators that will provide therapeutic relief from patients suffering from diseases associated with dysregulation of 5-hydroxytryptamine receptor 7 activity. The invention addresses the need to identify novel 5-HT7 modulators capable of treating disease associated with dysregulation of 5-hydroxytryptamine receptor 7 activity. The present invention addresses the need to develop new therapeutic agents for the treatment and prevention of circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder.

The 5-hydroxytryptamine receptor 7 activity modulators of the present invention are capable of treating and preventing diseases associated with dysregulation of 5-hydroxytryptamine receptor 7 activity, for example circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder. It has been discovered that the 5-hydroxytryptamine receptor 7 play a role in a number of medical disorders, and therefore, 5-HT7 receptor activity modulators are likely to have a beneficial effect on patients suffering from these disorders. The disorders in which 5-HT7 dysregulation plays a role and modulation of 5-HT7 receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et. al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, and bipolar disorder (WO20040229874). Without wishing to be limited by theory, it is believed that 5-hydroxytryptamine receptor 7 receptor activity modulators of the present invention can ameliorate, abate, otherwise cause to be controlled, diseases associated with dysregulation of 5-hydroxytryptamine receptor 7 activity. The diseases include, but are not limited to circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2amino$, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —CF$_3$, —CF$_2$CF$_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "haloalkoxy" refers to the group —O-haloalkyl, wherein the haloalkyl group is as defined above. Examples of haloalkoxy groups include, but are not limited to, fluoromethoxy, difluoromethoxy, trifluoromethoxy, and pentafluoroethoxyl.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, 1H-benzo[d]imidazol-2(3H)-onyl, 1H-benzo[d]imidazolyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

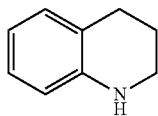

is, for the purposes of the present invention, considered a heterocyclic unit. 6,7-Dihydro-5H-cyclopentapyrimidine having the formula:

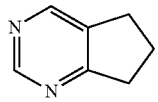

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

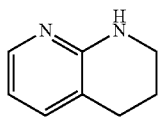

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^8$, —SR$^8$, —N(R$^8$)$_2$, —NR$^8$C(O)R$^8$, —SO$_2$R$^8$, —SO$_2$OR$^8$, —SO$_2$N(R$^8$)$_2$, —C(O)R$^8$, —C(O)OR$^8$, —C(O)N(R$^8$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^8$; wherein R$^8$, at each occurrence, independently is hydrogen, —OR$^9$, —SR$^9$, —C(O)R$^9$, —C(O)OR$^9$, —C(O)N(R$^9$)$_2$, —SO$_2$R$^9$, —S(O)$_2$OR$^9$, —N(R$^9$)$_2$, —NR$^9$C(O)R$^9$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^x$ units taken together with the atom(s) to which they are bound form an optionally substituted carbocycle or heterocycle wherein said carbocycle or heterocycle has 3 to 7 ring atoms; wherein R$^9$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^9$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{10}$; for example, —OH, —OCH$_3$, —OCH$_2$CH$_3$, —OCH$_2$CH$_2$CH$_3$;
ii) —C(O)R$^{10}$; for example, —COCH$_3$, —COCH$_2$CH$_3$, —COCH$_2$CH$_2$CH$_3$;
iii) —C(O)OR$^{10}$; for example, —CO$_2$CH$_3$, —CO$_2$CH$_2$CH$_3$, —CO$_2$CH$_2$CH$_2$CH$_3$;
iv) —C(O)N(R$^{10}$)$_2$; for example, —CONH$_2$, —CONHCH$_3$, —CON(CH$_3$)$_2$;
v) —N(R$^{10}$)$_2$; for example, —NH$_2$, —NHCH$_3$, —N(CH$_3$)$_2$, —NH(CH$_2$CH$_3$);

vi) halogen: —F, —Cl, —Br, and —I;
vii) —CH$_e$X$_g$; wherein X is halogen, m is from 0 to 2, e+g=3; for example, CH$_2$F, —CHF$_2$, —CF$_3$, —CCl$_3$, or —CBr$_3$;
viii) —SO$_2$R$^{10}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{10}$)C(O)R$^{10}$;
xiii) Oxo (=O);
xiv) Heterocycle; and
xv) Heteroaryl.

wherein each R$^{10}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{10}$ units can be taken together to form a ring comprising 3-7 ring atoms. In certain aspects, each R$^{10}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

For the purposes of the present invention the terms "compound," "analog," and "composition of matter" stand equally well for the 5-hydroxytryptamine receptor 7 activity modulators described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^9$)$_2$, each R$^9$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The 5-Hydroxytryptamine Receptor 7 Activity Modulators

The 5-hydroxytryptamine receptor 7 activity modulators of the present invention include all enantiomeric and diastereomeric forms alts thereof having the formula

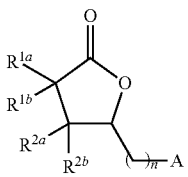

(I)

Including hydrates, solvates, pharmaceutically acceptable salts, prodrugs and complexes thereof, wherein:

A is selected from a group consisting of

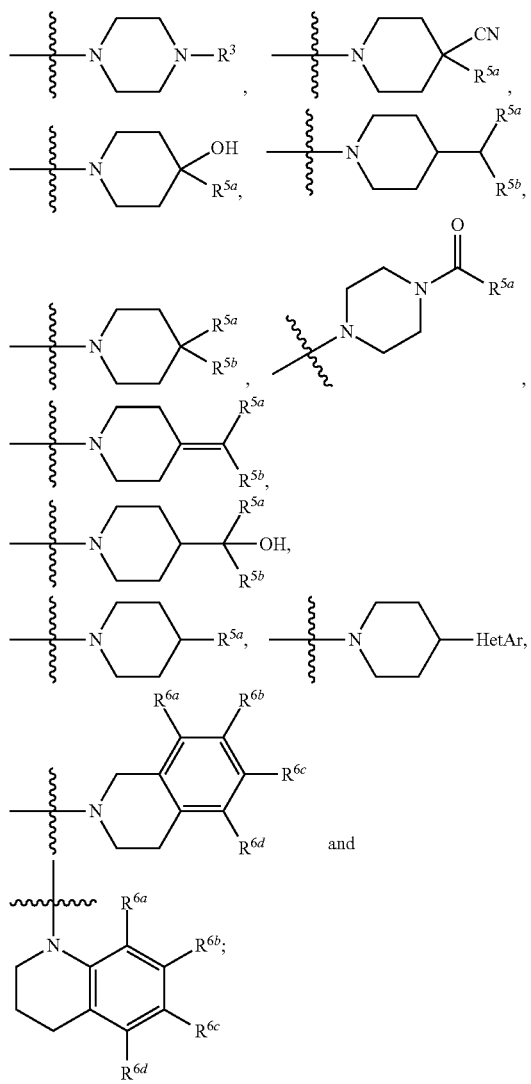

and $R^{1a}$ and $R^{1b}$ are independently selected from a group consisting of hydrogen, $C_{1-6}$ linear alkyl, $C_{1-6}$ branched alkyl, and optionally substituted aryl, or $R^{1a}$ and $R^{1b}$ are taken together with the atom to which they are bound to form a ring having from 3 to 7 ring atoms;

$R^{2a}$ and $R^{2b}$ are independently selected from a group consisting of hydrogen, $C_{1-6}$ linear alkyl, $C_{1-6}$ branched alkyl, and optionally substituted aryl, or $R^{2a}$ and $R^{2b}$ are taken together with the atom to which they are bound to form a ring having from 3 to 7 ring atoms;

$R^3$ is selected from a group consisting of $C_{1-6}$ linear alkyl, $C_{1-6}$ branched alkyl, $C_{3-7}$ cycloalkyl, optionally substituted aryl, optionally substituted heteroaryl,

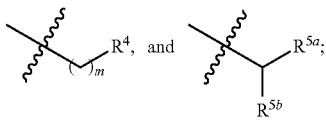

$R^4$ is optionally substituted aryl;

$R^{5a}$ and $R^{5b}$ are each independently optionally substituted aryl;

$R^{6a}$, $R^{6b}$, $R^{6c}$, and $R^{6d}$ are each independently selected from a group consisting of hydrogen, halogen, OH, $C_{1-6}$ linear alkyl, $C_{1-6}$ branched alkyl, $C_{1-6}$ alkoxy, $C_{1-6}$ haloalkyl, $C_{1-6}$ haloalkoxy, cyano, NH($C_{1-6}$ alkyl), N($C_{1-6}$ alkyl)$_2$, NHC(O)R$^7$, C(O)NHR$^7$, C(O)N(R$^7$)$_2$, SH, SC$_{1-6}$ alkyl, SO$^2$NH$_2$, SO$_2$NHR$^7$, SO$_2$R$^7$, and NHSO$_2$R$^7$;

$R^7$ is independently selected at each occurrence from a group consisting of $C_{1-6}$ linear alkyl, $C_{1-6}$ branched alkyl, and $C_{3-7}$ cycloalkyl;

HetAr is optionally substituted heteroaryl;

n is 1, 2, or 3;

and m is 1 or 2.

The embodiments of the present invention include compounds having formula (II):

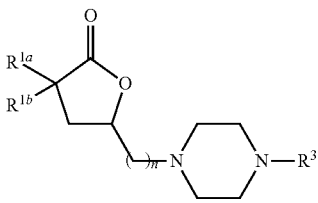

(II)

Including hydrates, solvates, enantiomers, diastereomers, pharmaceutically acceptable salts, and complexes thereof.

The embodiments of the present invention include compounds having formula (III):

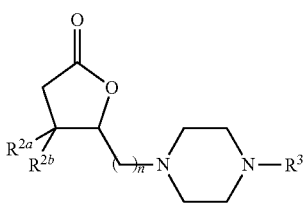

(III)

Including hydrates, solvates, enantiomers, diastereomers, pharmaceutically acceptable salts, and complexes thereof.

The embodiments of the present invention include compounds having formula (IV):

(IV)

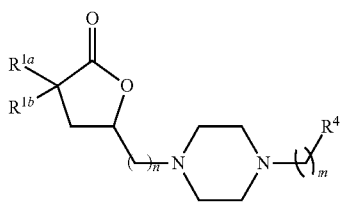

Including hydrates, solvates, enantiomers, diastereomers, pharmaceutically acceptable salts, and complexes thereof.

The embodiments of the present invention include compounds having formula (V):

(V)

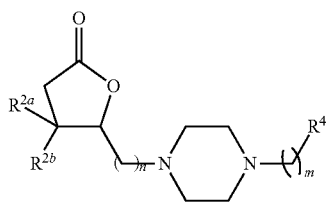

Including hydrates, solvates, enantiomers, diastereomers, pharmaceutically acceptable salts, and complexes thereof.

The embodiments of the present invention include compounds having formula (VI):

(VI)

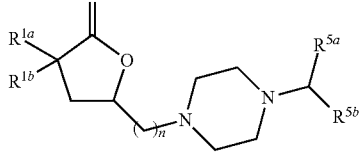

Including hydrates, solvates, enantiomers, diastereomers, pharmaceutically acceptable salts, and complexes thereof.

The embodiments of the present invention include compounds having formula (VII):

(VII)

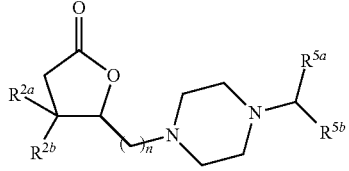

Including hydrates, solvates, enantiomers, diastereomers, pharmaceutically acceptable salts, and complexes thereof.

The embodiments of the present invention include compounds having formula (VIII):

(VIII)

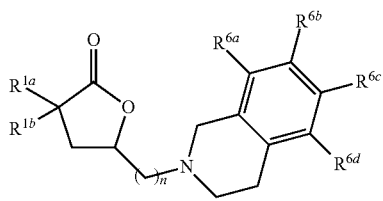

Including hydrates, solvates, enantiomers, diastereomers, pharmaceutically acceptable salts, and complexes thereof.

The embodiments of the present invention include compounds having formula (IX):

(IX)

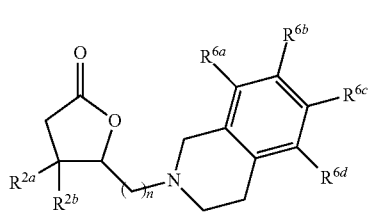

Including hydrates, solvates, enantiomers, diastereomers, pharmaceutically acceptable salts, and complexes thereof.

The embodiments of the present invention include compounds having formula (X):

(X)

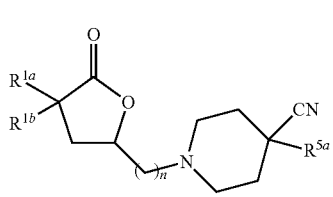

Including hydrates, solvates, enantiomers, diastereomers, pharmaceutically acceptable salts, and complexes thereof.

The embodiments of the present invention include compounds having formula (XI):

(XI)

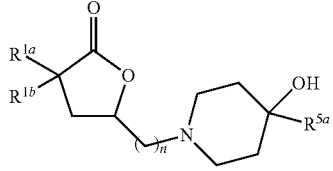

Including hydrates, solvates, enantiomers, diastereomers, pharmaceutically acceptable salts, and complexes thereof.

The embodiments of the present invention include compounds having formula (XII):

(XII)

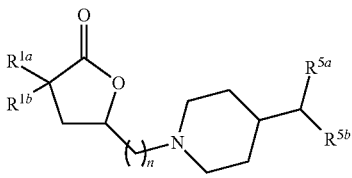

Including hydrates, solvates, enantiomers, diastereomers, pharmaceutically acceptable salts, and complexes thereof.

The embodiments of the present invention include compounds having formula (XIII):

(XIII)

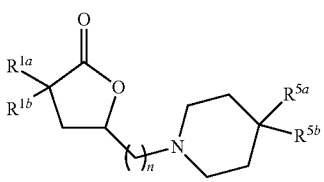

Including hydrates, solvates, enantiomers, diastereomers, pharmaceutically acceptable salts, and complexes thereof.

The embodiments of the present invention include compounds having formula (XIV):

(XIV)

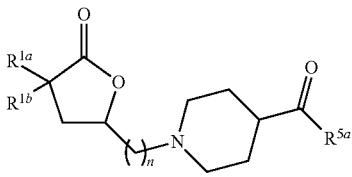

Including hydrates, solvates, enantiomers, diastereomers, pharmaceutically acceptable salts, and complexes thereof.

The embodiments of the present invention include compounds having formula (XV):

(XV)

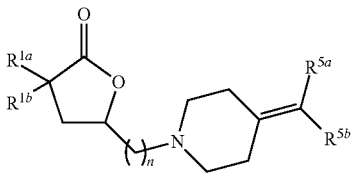

Including hydrates, solvates, enantiomers, diastereomers, pharmaceutically acceptable salts, and complexes thereof.

The embodiments of the present invention include compounds having formula (XVI):

(XVI)

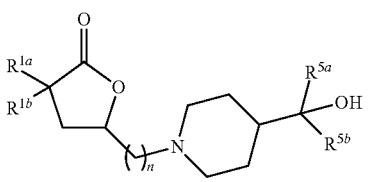

Including hydrates, solvates, enantiomers, diastereomers, pharmaceutically acceptable salts, and complexes thereof.

The embodiments of the present invention include compounds having formula (XVII):

(XVII)

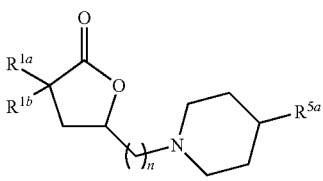

Including hydrates, solvates, enantiomers, diastereomers, pharmaceutically acceptable salts, and complexes thereof.

The embodiments of the present invention include compounds having formula (XVIII):

(XVIII)

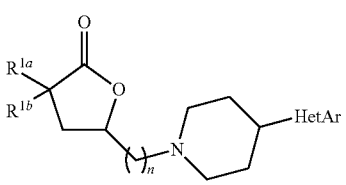

Including hydrates, solvates, enantiomers, diastereomers, pharmaceutically acceptable salts, and complexes thereof.

In some embodiments A is

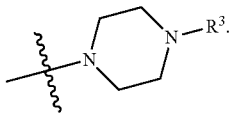

In some embodiments A is

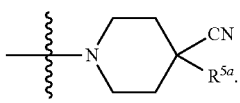

In some embodiments A is

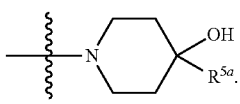

In some embodiments A is

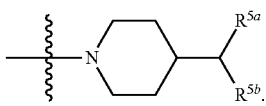

In some embodiments A is

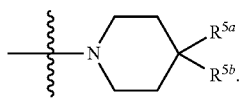

In some embodiments A is

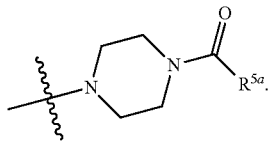

In some embodiments A is

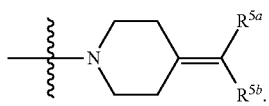

In some embodiments A is

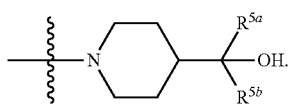

In some embodiments A is

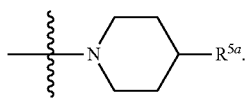

In some embodiments A is

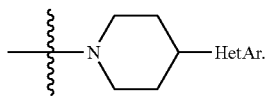

In some embodiments A is

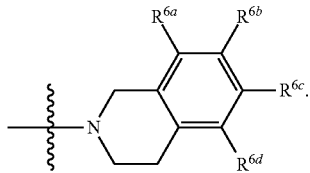

In some embodiments A is

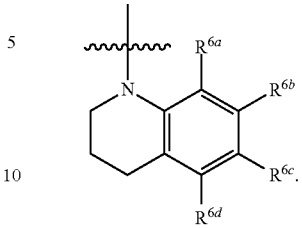

In some embodiments $R^{1a}$ is hydrogen.
In some embodiments $R^{1a}$ is $C_{1-6}$ linear alkyl.
In some embodiments $R^{1a}$ is $C_{1-6}$ branched alkyl.
In some embodiments $R^{1a}$ is optionally substituted aryl.
In some embodiments $R^{1b}$ is hydrogen.
In some embodiments $R^{1b}$ is $C_{1-6}$ linear alkyl.
In some embodiments $R^{1b}$ is $C_{1-6}$ branched alkyl.
In some embodiments $R^{1b}$ is optionally substituted aryl.
In some embodiments $R^{1a}$ and $R^{1b}$ are taken together with the atom to which they are bound to form a ring having 3 ring atoms.
In some embodiments $R^{1a}$ and $R^{1b}$ are taken together with the atom to which they are bound to form a ring having 4 ring atoms.
In some embodiments $R^{1a}$ and $R^{1b}$ are taken together with the atom to which they are bound to form a ring having 5 ring atoms.
In some embodiments $R^{1a}$ and $R^{1b}$ are taken together with the atom to which they are bound to form a ring having 6 ring atoms.
In some embodiments $R^{1a}$ and $R^{1b}$ are taken together with the atom to which they are bound to form a ring having 7 ring atoms.
In some embodiments $R^{2a}$ is hydrogen.
In some embodiments $R^{2a}$ is $C_{1-6}$ linear alkyl.
In some embodiments $R^{2a}$ is $C_{1-6}$ branched alkyl.
In some embodiments $R^{2a}$ is optionally substituted aryl.
In some embodiments $R^{2b}$ is hydrogen.
In some embodiments $R^{2b}$ is $C_{1-6}$ linear alkyl.
In some embodiments $R^{2b}$ is $C_{1-6}$ branched alkyl.
In some embodiments $R^{2b}$ is optionally substituted aryl.
In some embodiments $R^{2a}$ and $R^{2b}$ are taken together with the atom to which they are bound to form a ring having 3 ring atoms.
In some embodiments $R^{2a}$ and $R^{2b}$ are taken together with the atom to which they are bound to form a ring having 4 ring atoms.
In some embodiments $R^{2a}$ and $R^{2b}$ are taken together with the atom to which they are bound to form a ring having 5 ring atoms.
In some embodiments $R^{2a}$ and $R^{2b}$ are taken together with the atom to which they are bound to form a ring having 6 ring atoms.
In some embodiments $R^{2a}$ and $R^{2b}$ are taken together with the atom to which they are bound to form a ring having 7 ring atoms.
In some embodiments $R^3$ is $C_{1-6}$ linear alkyl.
In some embodiments $R^3$ is $C_{1-6}$ branched alkyl.
In some embodiments $R^3$ is $C_{3-7}$ cycloalkyl.
In some embodiments $R^3$ is optionally substituted aryl.
In some embodiments $R^3$ is optionally substituted heteroaryl.

In some embodiments $R^3$ is

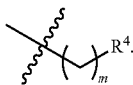

In some embodiments $R^3$ is

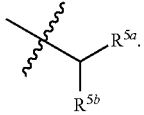

In some embodiments $R^4$ is optionally substituted aryl.
In some embodiments $R^{5a}$ is optionally substituted aryl.
In some embodiments $R^{5b}$ is optionally substituted aryl.
In some embodiments $R^{6a}$ is hydrogen.
In some embodiments $R^{6a}$ is halogen.
In some embodiments $R^{6a}$ is OH.
In some embodiments $R^{6a}$ is $C_{1-6}$ linear alkyl.
In some embodiments $R^{6a}$ is $C_{1-6}$ branched alkyl.
In some embodiments $R^{6a}$ is $C_{1-6}$ alkoxy.
In some embodiments $R^{6a}$ is $C_{1-6}$ haloalkyl.
In some embodiments $R^{6a}$ is $C_{1-6}$ haloalkoxy.
In some embodiments $R^{6a}$ is cyano.
In some embodiments $R^{6a}$ is $NH(C_{1-6}$ alkyl).
In some embodiments $R^{6a}$ is $N(C_{1-6}$ alkyl$)_2$.
In some embodiments $R^{6a}$ is $NHC(O)R^7$.
In some embodiments $R^{6a}$ is $C(O)NHR^7$.
In some embodiments $R^{6a}$ is $C(O)N(R^7)_2$.
In some embodiments $R^{6a}$ is SH.
In some embodiments $R^{6a}$ is $SC_{1-6}$ alkyl.
In some embodiments $R^{6a}$ is $SO^2NH_2$.
In some embodiments $R^{6a}$ is $SO_2NHR^7$.
In some embodiments $R^{6a}$ is $SO_2R^7$.
In some embodiments $R^{6a}$ is $NHSO_2R^7$.
In some embodiments $R^{6b}$ is hydrogen.
In some embodiments $R^{6b}$ is halogen.
In some embodiments $R^{6b}$ is OH.
In some embodiments $R^{6b}$ is $C_{1-6}$ linear alkyl.
In some embodiments $R^{6b}$ is $C_{1-6}$ branched alkyl.
In some embodiments $R^{6b}$ is $C_{1-6}$ alkoxy.
In some embodiments $R^{6b}$ is $C_{1-6}$ haloalkyl.
In some embodiments $R^{6b}$ is $C_{1-6}$ haloalkoxy.
In some embodiments $R^{6b}$ is cyano.
In some embodiments $R^{6b}$ is $NH(C_{1-6}$ alkyl).
In some embodiments $R^{6b}$ is $N(C_{1-6}$ alkyl$)_2$.
In some embodiments $R^{6b}$ is $NHC(O)R^7$.
In some embodiments $R^{6b}$ is $C(O)NHR^7$.
In some embodiments $R^{6b}$ is $C(O)N(R^7)_2$.
In some embodiments $R^{6b}$ is SH.
In some embodiments $R^{6b}$ is $SC_{1-6}$ alkyl.
In some embodiments $R^{6b}$ is $SO^2NH_2$.
In some embodiments $R^{6b}$ is $SO_2NHR^7$.
In some embodiments $R^{6b}$ is $SO_2R^7$.
In some embodiments $R^{6b}$ is $NHSO_2R^7$.
In some embodiments $R^{6c}$ is hydrogen.
In some embodiments $R^{6c}$ is halogen.
In some embodiments $R^{6c}$ is OH.
In some embodiments $R^{6c}$ is $C_{1-6}$ linear alkyl.
In some embodiments $R^{6c}$ is $C_{1-6}$ branched alkyl.
In some embodiments $R^{6c}$ is $C_{1-6}$ alkoxy.
In some embodiments $R^{6c}$ is $C_{1-6}$ haloalkyl.
In some embodiments $R^{6c}$ is $C_{1-6}$ haloalkoxy.
In some embodiments $R^{6c}$ is cyano.
In some embodiments $R^{6c}$ is $NH(C_{1-6}$ alkyl)
In some embodiments $R^{6c}$ is $N(C_{1-6}$ alkyl$)_2$.
In some embodiments $R^{6c}$ is $NHC(O)R^7$.
In some embodiments $R^{6c}$ is $C(O)NHR^7$.
In some embodiments $R^{6c}$ is $C(O)N(R^7)_2$.
In some embodiments $R^{6c}$ is SH.
In some embodiments $R^{6c}$ is $SC_{1-6}$ alkyl.
In some embodiments $R^{6c}$ is $SO^2NH_2$.
In some embodiments $R^{6c}$ is $SO_2NHR^7$.
In some embodiments $R^{6c}$ is $SO_2R^7$.
In some embodiments $R^{6c}$ is $NHSO_2R^7$.
In some embodiments $R^{6d}$ is hydrogen.
In some embodiments $R^{6d}$ is halogen.
In some embodiments $R^{6d}$ is OH.
In some embodiments $R^{6d}$ is $C_{1-6}$ linear alkyl.
In some embodiments $R^{6d}$ is $C_{1-6}$ branched alkyl.
In some embodiments $R^{6d}$ is $C_{1-6}$ alkoxy.
In some embodiments $R^{6d}$ is $C_{1-6}$ haloalkyl.
In some embodiments $R^{6d}$ is $C_{1-6}$ haloalkoxy.
In some embodiments $R^{6d}$ is cyano.
In some embodiments $R^{6d}$ is $NH(C_{1-6}$ alkyl).
In some embodiments $R^{6d}$ is $N(C_{1-6}$ alkyl$)_2$.
In some embodiments $R^{6d}$ is $NHC(O)R^7$.
In some embodiments $R^{6d}$ is $C(O)NHR^7$.
In some embodiments $R^{6d}$ is $C(O)N(R^7)_2$.
In some embodiments R6d is SH.
In some embodiments $R^{6d}$ is $SC_{1-6}$ alkyl.
In some embodiments $R^{6d}$ is $SO^2NH_2$.
In some embodiments $R^{6d}$ is $SO_2NHR^7$.
In some embodiments $R^{6d}$ is $SO_2R^7$.
In some embodiments $R^{6d}$ is $NHSO_2R^7$.
In some embodiments $R^7$ is $C_{1-6}$ linear alkyl.
In some embodiments $R^7$ is $C_{1-6}$ branched alkyl.
In some embodiments $R^7$ is $C_{3-7}$ cycloalkyl.
HetAr is optionally substituted heteroaryl.
In some embodiments n is 1.
In some embodiments n is 2.
In some embodiments n is 3.
In some embodiments m is 1.
In some embodiments m is 2.

Exemplary embodiments include compounds having the formula (I) or a pharmaceutically acceptable salt form thereof defined herein below in Table 1.

TABLE 1

| Entry | Structure | Entry | Structure |
|---|---|---|---|
| 230010 | 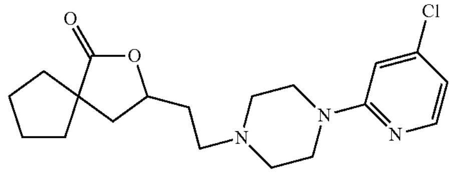 [SMILES: O=C1OC(CCN2CCN(c3cc(Cl)ccn3)CC2)CC12CCCC2] | 160152 | 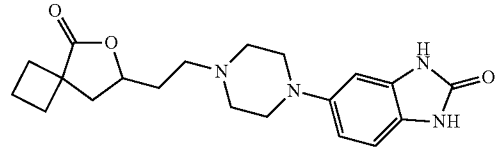 [SMILES: O=C1OC(CCN2CCN(c3ccc4[nH]c(=O)[nH]c4c3)CC2)CC12CCC2] |

TABLE 1-continued
| Entry | Structure | Entry | Structure |
|---|---|---|---|
| 230012 | 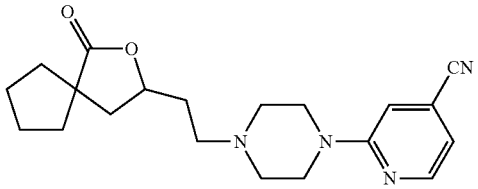 [SMILES: N#Cc1ccnc(N2CCN(CCC3CC4(CCCC4)C(=O)O3)CC2)c1] | 160153 | 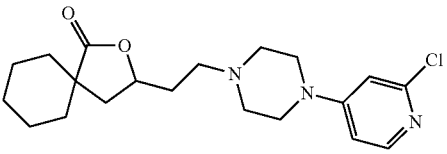 [SMILES: O=C1OC(CCN2CCN(c3ccnc(Cl)c3)CC2)CC12CCCCC2] |
| 230009 | 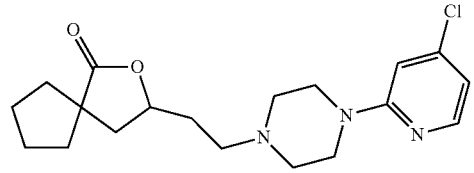 [SMILES: O=C1OC(CCN2CCN(c3cc(Cl)ccn3)CC2)CC12CCCC2] | 160154 | 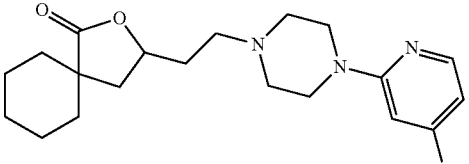 |
| 230011 | 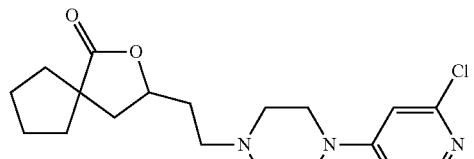 | 160155 | 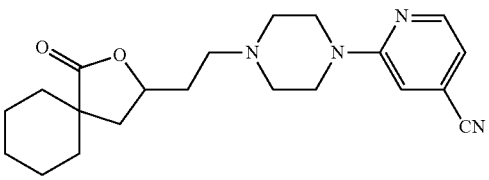 [SMILES: N#Cc1ccnc(N2CCN(CCC3CC4(CCCCC4)C(=O)O3)CC2)c1] |
| 230016 | 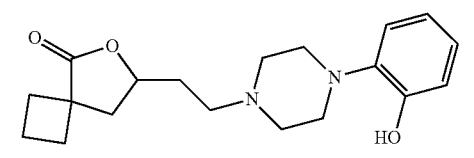 [SMILES: O=C1OC(CCN2CCN(c3ccccc3O)CC2)CC12CCC2] | 160156 | 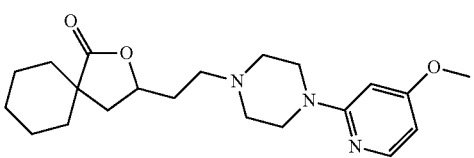 [SMILES: COc1ccnc(N2CCN(CCC3CC4(CCCCC4)C(=O)O3)CC2)c1] |
| 230015 | 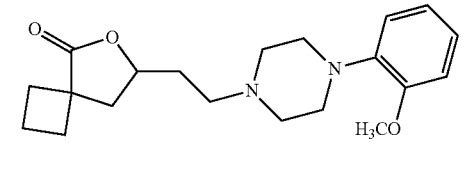 [SMILES: COc1ccccc1N1CCN(CCC2CC3(CCC3)C(=O)O2)CC1] | 160157 | 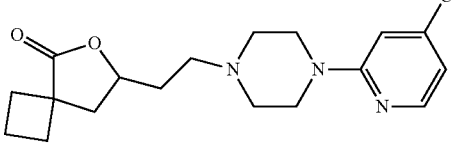 |
| 230014 | 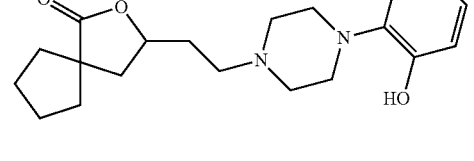 | 160158 | 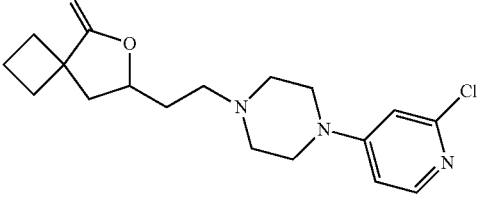 |
| 230013 | 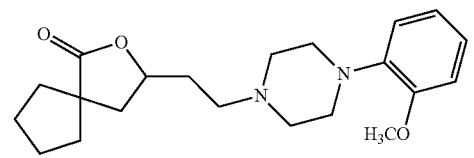 | 160159 | 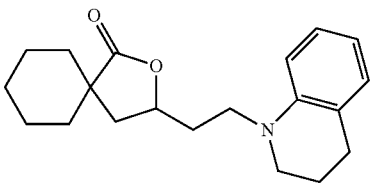 [SMILES: O=C1OC(CCN2CCCc3ccccc32)CC12CCCCC2] |
| 230008 | 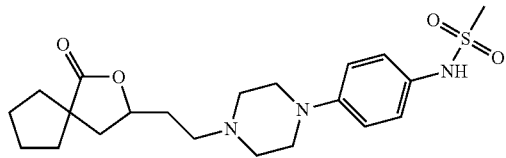 [SMILES: CS(=O)(=O)Nc1ccc(N2CCN(CCC3CC4(CCCC4)C(=O)O3)CC2)cc1] | 160160 | 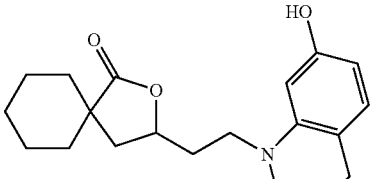 |

TABLE 1-continued
| Entry | Structure | Entry | Structure |
|---|---|---|---|
| 160145 | 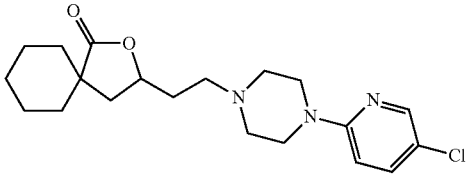 [SMILES: O=C1OC(CCN2CCN(c3ccc(Cl)cn3)CC2)CC12CCCCC2] | 160161 | 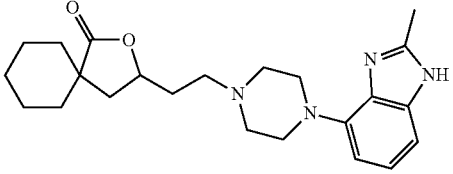 [SMILES: Cc1nc2c(N3CCN(CCC4CC5(CCCCC5)C(=O)O4)CC3)cccc2[nH]1] |
| 160146 | 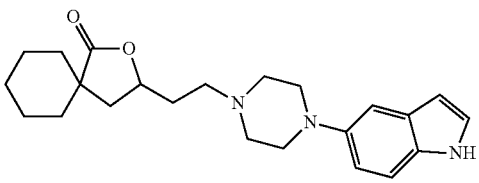 [SMILES: O=C1OC(CCN2CCN(c3ccc4[nH]ccc4c3)CC2)CC12CCCCC2] | 160162 | 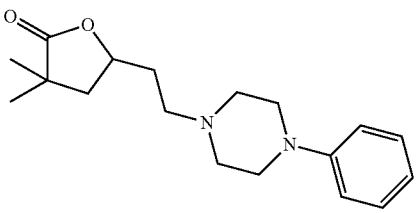 [SMILES: CC1(C)CC(CCN2CCN(c3ccccc3)CC2)OC1=O] |
| 160147 | 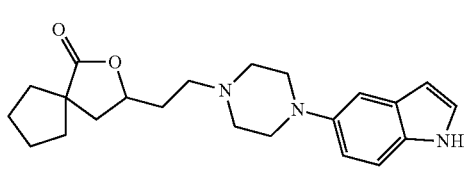 [SMILES: O=C1OC(CCN2CCN(c3ccc4[nH]ccc4c3)CC2)CC12CCCC2] | 160163 | 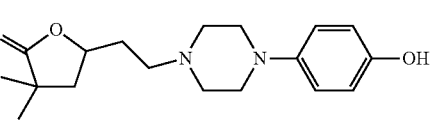 |
| 160148 | 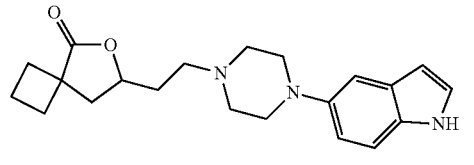 [SMILES: O=C1OC(CCN2CCN(c3ccc4[nH]ccc4c3)CC2)CC12CCC2] | 160164 | 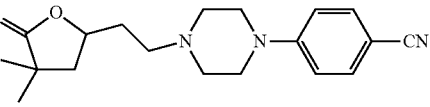 |
| 160149 | 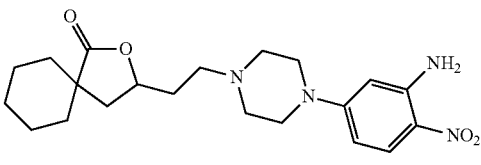 [SMILES: Nc1cc(N2CCN(CCC3CC4(CCCCC4)C(=O)O3)CC2)ccc1[N+](=O)[O-]] | 160165 | 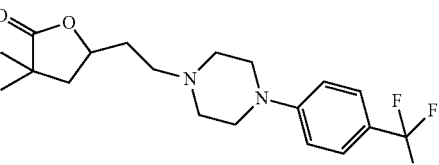 |
| 160150 | 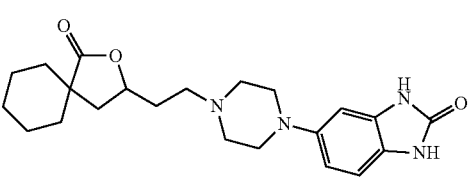 [SMILES: O=C1OC(CCN2CCN(c3ccc4[nH]c(=O)[nH]c4c3)CC2)CC12CCCCC2] | 160166 | 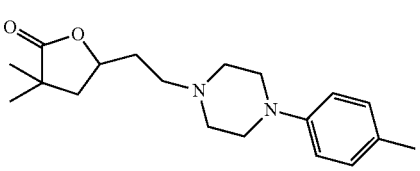 [SMILES: Cc1ccc(N2CCN(CCC3CC(C)(C)C(=O)O3)CC2)cc1] |
| 160151 | 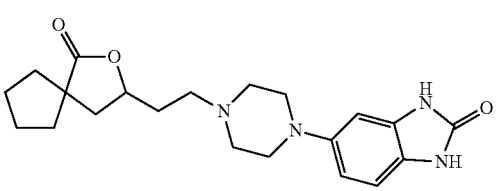 [SMILES: O=C1OC(CCN2CCN(c3ccc4[nH]c(=O)[nH]c4c3)CC2)CC12CCCC2] | 230039 | 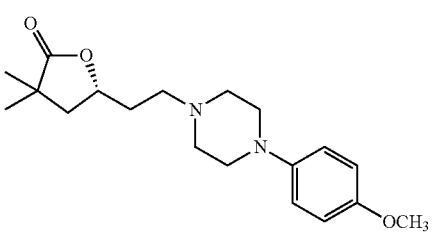 [SMILES: COc1ccc(N2CCN(CC[C@@H]3CC(C)(C)C(=O)O3)CC2)cc1] |
| 230046 | 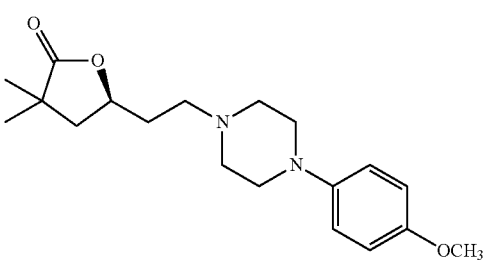 [SMILES: COc1ccc(N2CCN(CC[C@H]3CC(C)(C)C(=O)O3)CC2)cc1] | 230040 | 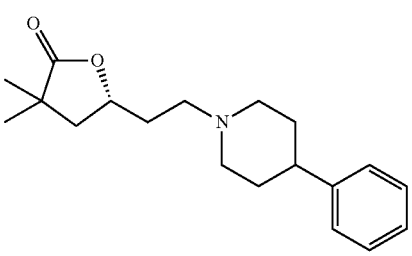 [SMILES: CC1(C)C[C@@H](CCN2CCC(c3ccccc3)CC2)OC1=O] |

TABLE 1-continued

| Entry | Structure | Entry | Structure |
|---|---|---|---|
| 230047 | 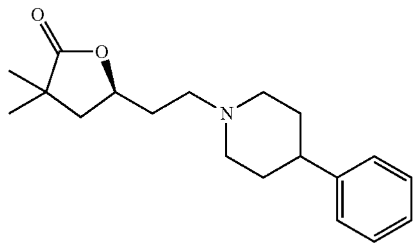 [SMILES: CC1(C)C[C@H](CCN2CCC(c3ccccc3)CC2)OC1=O] | 230057 | 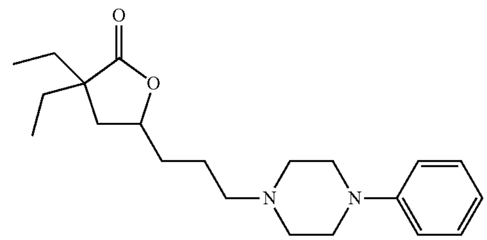 [SMILES: CCC1(CC)CC(CCCN2CCN(c3ccccc3)CC2)OC1=O] |
| 230058 | 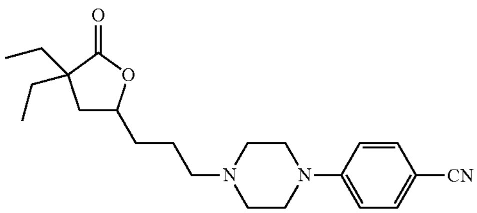 | 230059 | 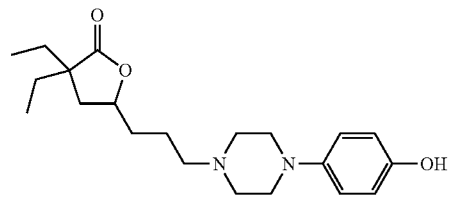 [SMILES: CCC1(CC)CC(CCCN2CCN(c3ccc(O)cc3)CC2)OC1=O] |
| 230060 | 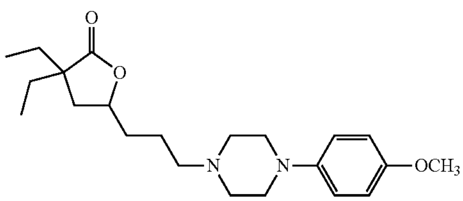 [SMILES: CCC1(CC)CC(CCCN2CCN(c3ccc(OC)cc3)CC2)OC1=O] | 230061 | 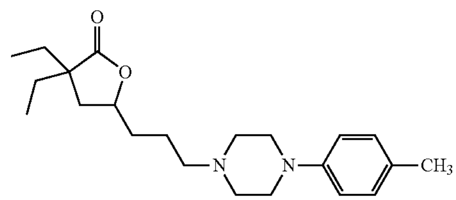 [SMILES: CCC1(CC)CC(CCCN2CCN(c3ccc(C)cc3)CC2)OC1=O] |
| 230062 | 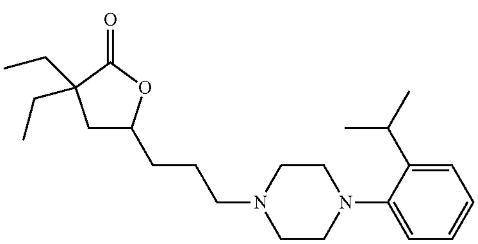 [SMILES: CCC1(CC)CC(CCCN2CCN(c3ccccc3C(C)C)CC2)OC1=O] | 230063 | 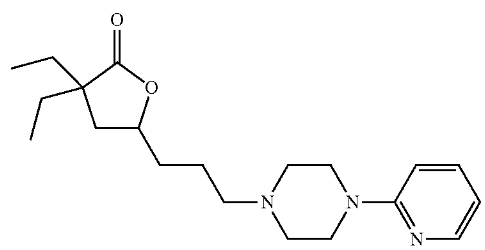 [SMILES: CCC1(CC)CC(CCCN2CCN(c3ccccn3)CC2)OC1=O] |
| 230068 | 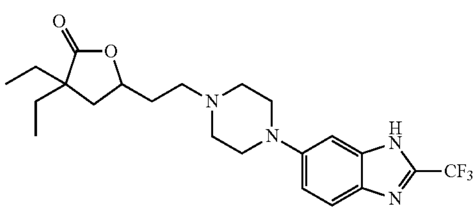 [SMILES: CCC1(CC)CC(CCN2CCN(c3ccc4nc(C(F)(F)F)[nH]c4c3)CC2)OC1=O] | 230069 | 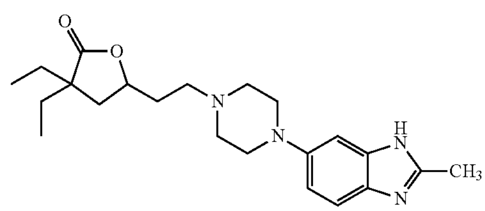 [SMILES: CCC1(CC)CC(CCN2CCN(c3ccc4nc(C)[nH]c4c3)CC2)OC1=O] |
| 230070 | 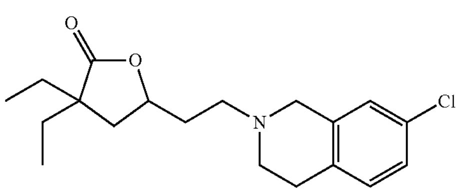 [SMILES: CCC1(CC)CC(CCN2CCc3ccc(Cl)cc3C2)OC1=O] | 230071 | 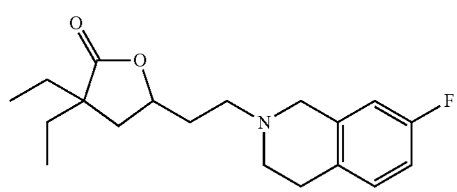 [SMILES: CCC1(CC)CC(CCN2CCc3ccc(F)cc3C2)OC1=O] |

TABLE 1-continued

| Entry | Structure | Entry | Structure |
|---|---|---|---|
| 230083 | 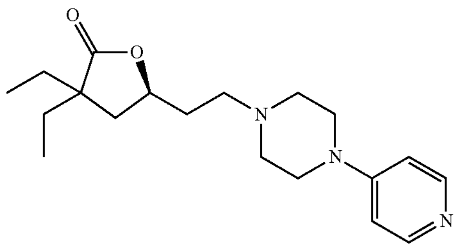 [SMILES: CCC1(CC)C[C@H](CCN2CCN(c3ccncc3)CC2)OC1=O] | | |

For the purposes of demonstrating the manner in which the compounds of the present invention are named and referred to herein, the compound having the formula:

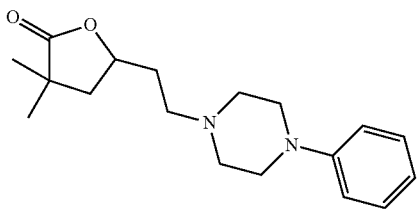 [SMILES: CC1(C)CC(CCN2CCN(c3ccccc3)CC2)OC1=O]

has the chemical name dihydro-3,3-dimethyl-5-(2-(4-phenylpiperazin-1-yl)ethyl)furan-2(3H)-one.

For the purposes of the present invention, a compound depicted by the racemic formula, for example:

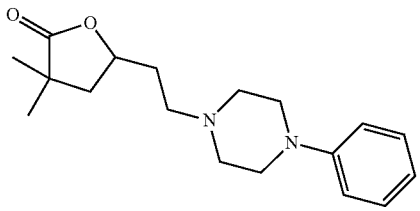 [SMILES: CC1(C)CC(CCN2CCN(c3ccccc3)CC2)OC1=O]

will stand equally well for either of the two enantiomers having the formula:

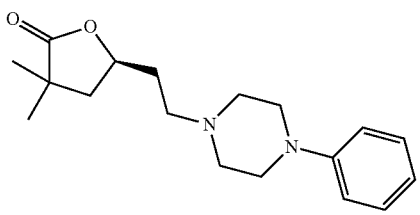 [SMILES: CC1(C)C[C@H](CCN2CCN(c3ccccc3)CC2)OC1=O]

or the formula:

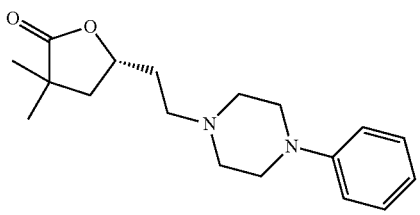 [SMILES: CC1(C)C[C@@H](CCN2CCN(c3ccccc3)CC2)OC1=O]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the 5-hydroxytryptamine receptor 7 activity modulators of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of the disclosure may be prepared according to the process outlined in Scheme 1.

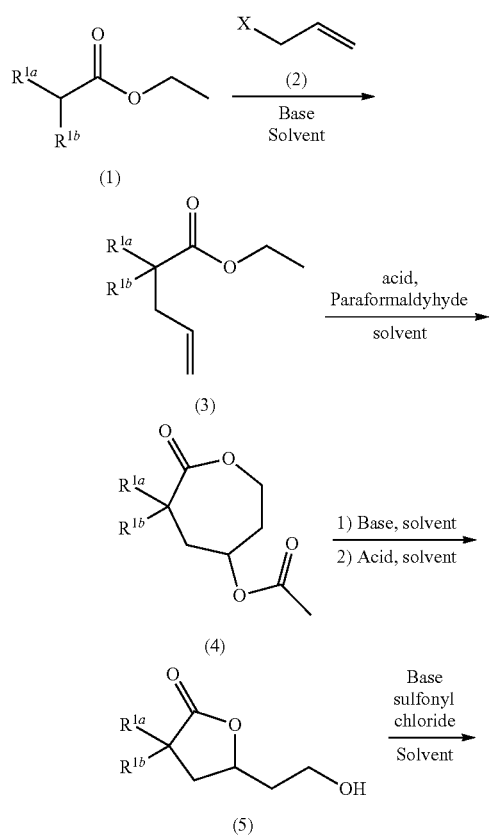

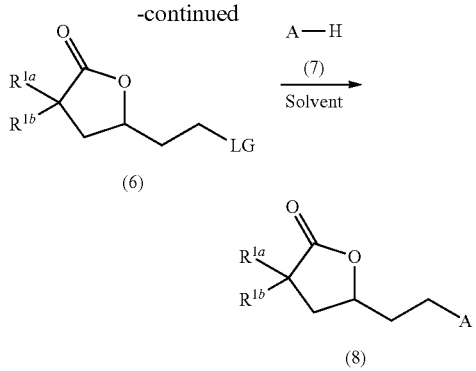

A suitably substituted compound of formula (1), a known compound or compound prepared by known methods, is reacted with a compound of the formula (2), wherein X is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in an organic solvent such as tetrahydrofuran, 1,4-dioxane, 1,2-dimethoxyethane, dimethylformamide, dimethylacetamide, and the like, to provide a compound of the formula (3). A compound of the formula (3) is then treated with paraformaldehyde in the presence of an acid such as sulfuric acid, hydrochloric acid, and the like, in an the presence of acetic acid, and optionally in an organic solvent such as methanol, ethanol, tetrahydrofuran, 1,4-dioxane, 1,2-dimethoxyethane, dimethylformamide, dimethylacetamide, and the like, optionally with heating, optionally with microwave irradiation to provide a compound of the formula (4). A compound of the formula (4) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, to provide a compound of the formula (5). A compound of the formula (5) is then converted to a compound of the formula (6), wherein LG is a mesylate, tosylate, nosylate, and the like, using methods that are known to one skilled in the art. Thus, a compound of the formula (5) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (6). A compound of the formula (6) is reacted with a compound of the formula (7), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (8).

Alternatively, compounds of formula (8) may be prepared according to the process outlined in Scheme 2:

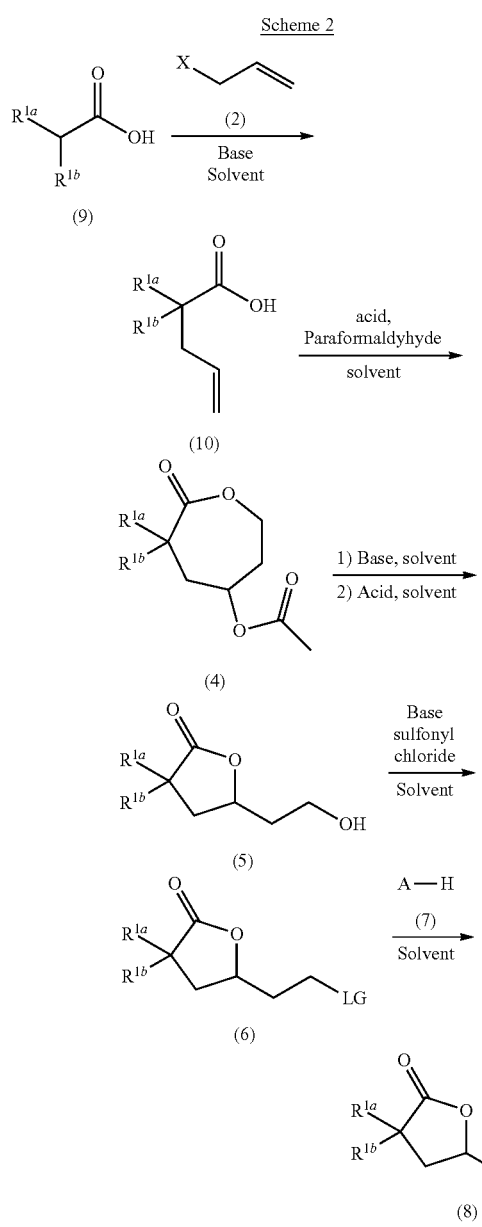

mide, dimethylacetamide, and the like, optionally with heating, optionally with microwave irradiation to provide a compound of the formula (4). A compound of the formula (4) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, optionally with heating, to provide a compound of the formula (5). A compound of the formula (5) is then converted to a compound of the formula (6), wherein LG is a mesylate, tosylate, nosylate, and the like, using methods that are known to one skilled in the art. Thus, a compound of the formula (5) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (6). A compound of the formula (6) is reacted with a compound of the formula (7), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (8).

Compounds of formula (21) may be prepared according to the process outlined in Scheme 3.

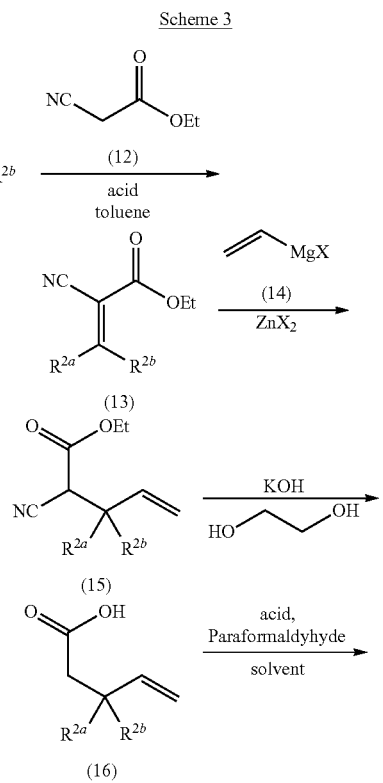

A suitably substituted compound of formula (9), a known compound or compound prepared by known methods, is reacted with a compound of the formula (2), wherein X is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, n-butyl lithium, sec-butyl lithium, tert-butyl lithium, and the like in an organic solvent such as tetrahydrofuran, 1,4-dioxane, 1,2-dimethoxyethane, dimethylformamide, dimethylacetamide, and the like, to provide a compound of the formula (10). A compound of the formula (10) is then treated with paraformaldehyde in the presence of an acid such as sulfuric acid, hydrochloric acid, and the like, in the presence of acetic acid, and optionally in an organic solvent such as methanol, ethanol, tetrahydrofuran, 1,4-dioxane, 1,2-dimethoxyethane, dimethylforma-

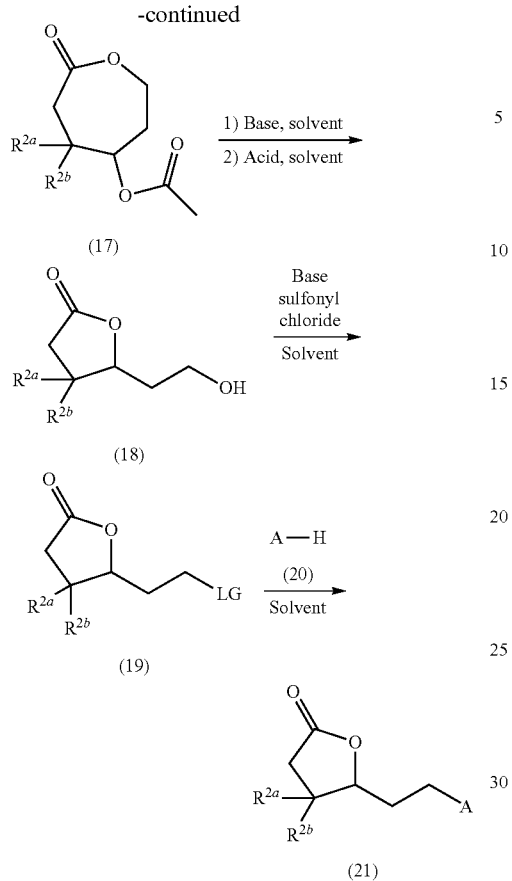

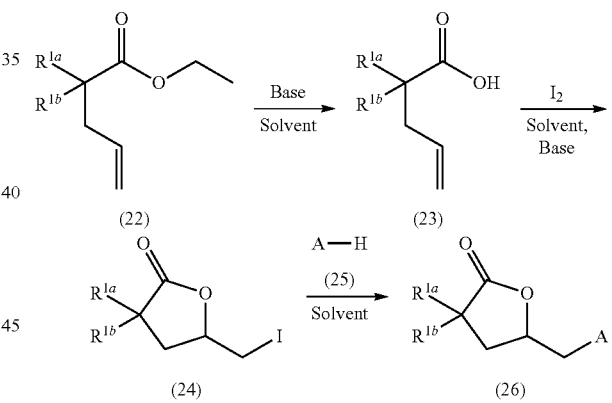

potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, optionally with heating, to provide a compound of the formula (18). A compound of the formula (18) is then converted to a compound of the formula (19), wherein LG is a mesylate, tosylate, nosylate, and the like, using methods that are known to one skilled in the art. Thus, a compound of the formula (18) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (19). A compound of the formula (19) is reacted with a compound of the formula (20), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (21).

Compounds of formula (26) may be prepared according to the process outlined in Scheme 4.

A suitably substituted compound of formula (11), a known compound or compound prepared by known methods, is reacted with a compound of the formula (12), in the presence of an ammonium salt such as ammonium acetate, ammonium formate, ammonium sulfate, ammonium chloride, and the like, in the presence of an acid such as formic acid, acetic acid, hydrochloric acid, sulfuric acid, and the like, in an organic solvent such as toluene, benzene, p-xylene, m-xylene, o-xylene, tetrahydrofuran, 1,4-dioxane, dimethylformamide, and the like, optionally with heating, optionally with microwave irradiation to provide a compound of the formula (13). A compound of the formula (13) is then reacted with a compound of the formula (14), wherein X is a halogen, in the presence of a compound of the formula $ZnX_2$, wherein X is a halogen, in an organic solvent such as tetrahydrofuran, 1,4-dioxane, 1,2-dimethoxyethane, dimethylformamide, dimethylacetamide, and the like to provide a compound of the formula (15). A compound of the formula (15) is then reacted with a base such as potassium hydroxide, sodium hydroxide, lithium hydroxide, potassium carbonate, sodium carbonate, lithium carbonate, and the like, in a solvent such as methanol, ethanol, isopropanol, ethylene glycol, propylene glycol, water, and the like, optionally with heating to provide a compound of the formula (16). A compound of the formula (16) is reacted with paraformaldehyde in the presence of an acid such as sulfuric acid, hydrochloric acid, and the like, in the presence of acetic acid, optionally in the presence of a solvent such as methanol, ethanol, tetrahydrofuran, 1,4-dioxane, dimethyl formamide, and the like, optionally with heating to provide a compound of the formula (17). A compound of the formula (17) is then treated with a base such as sodium hydroxide, A compound of the formula (22) is reacted with a base such as sodium hydroxide, potassium hydroxide, lithium hydroxide, sodium carbonate, potassium carbonate, lithium carbonate and the like, in the presence of a solvent such as methanol, ethanol, isopropanol, water, and the like, optionally with heating, optionally with microwave irradiation to provide a compound of the formula (23). A compound of the formula (23) is then reacted with iodine in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, and the like to provide a compound of the formula (24). A compound of the formula (24) is reacted with a compound of the formula (25), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (26).

Compounds of formula (35) may be prepared according to the process outlined in Scheme 5.

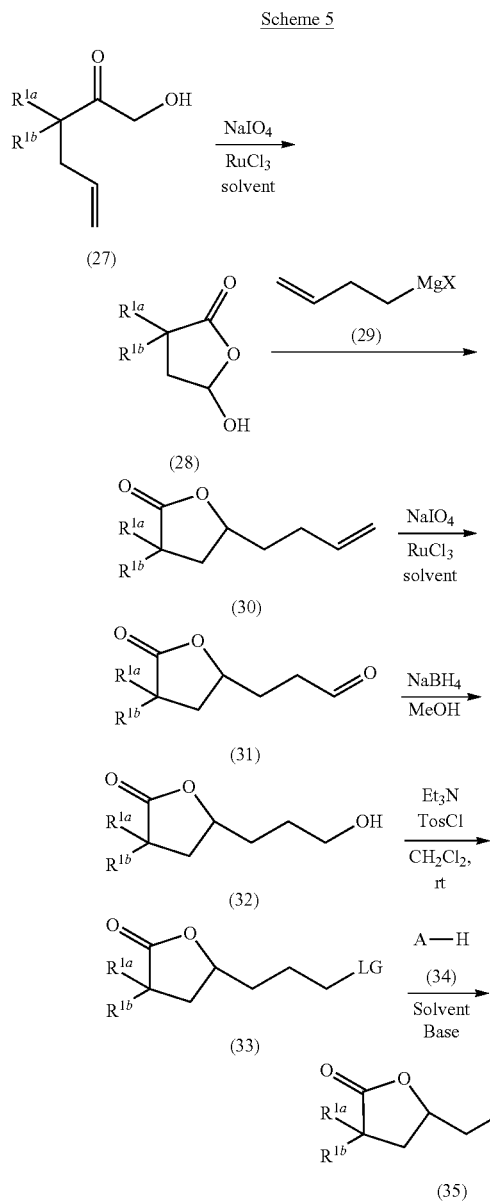

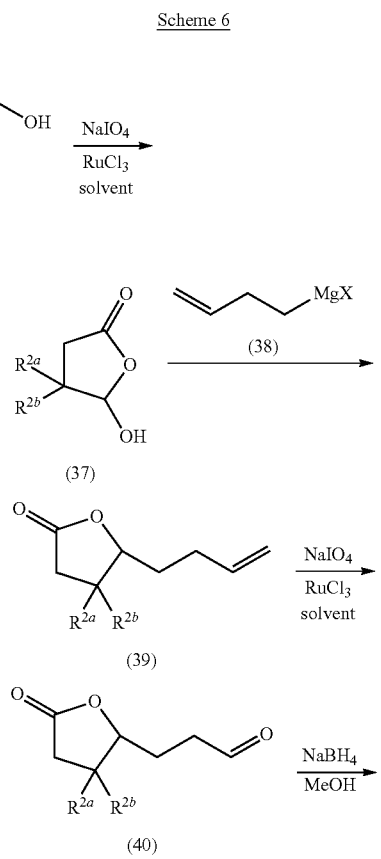

in a solvent such as acetonitrile, methanol, ethanol, isopropanol, and the like, to provide a compound of the formula (31). A compound of the formula (31) is reacted with a reducing agent such as lithium borohydride, sodium borohydride, sodium cyanoborohydride and the like, in a solvent such as methanol, ethanol, isopropanol, acetonitrile, and the like to provide a compound of the formula (32). A compound of the formula (32) is then converted to a compound of the formula (33), wherein LG is a mesylate, tosylate, nosylate, and the like, using methods that are known to one skilled in the art. Thus, a compound of the formula (32) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (33). A compound of the formula (33) is reacted with a compound of the formula (34), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (35).

Compounds of formula (44) may be prepared according to the process outlined in Scheme 6.

A compound of the formula (27) is reacted with ruthenium chloride in the presence of sodium periodate in a solvent such as acetonitrile, methanol, ethanol, isopropanol, and the like, to provide a compound of the formula (28). A compound of the formula (28) is reacted with a compound of the formula (29), a known compound or compound prepared by known methods, wherein x is a halogen, in the presence of a solvent such as ethyl ether, tetrahydrofuran, 1,4-dioxane and the like to provide a compound of the formula (30). A compound of the formula (30) is reacted with ruthenium chloride in the presence of sodium periodate

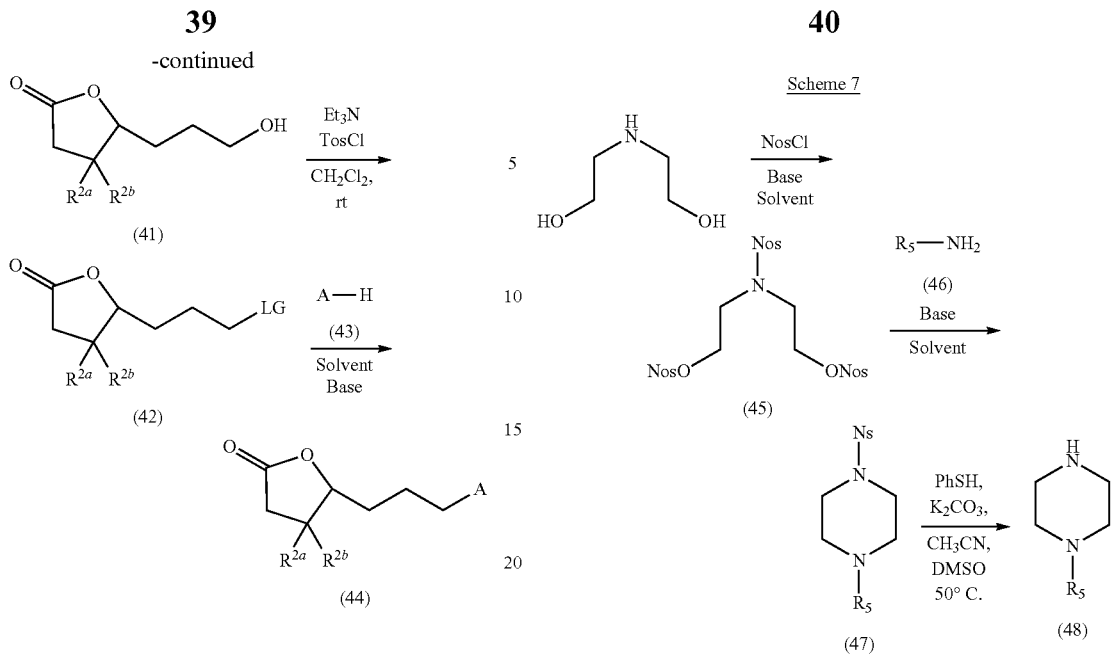

Scheme 7

A compound of the formula (36) is reacted with ruthenium chloride in the presence of sodium periodate in a solvent such as acetonitrile, methanol, ethanol, isopropanol, and the like, to provide a compound of the formula (37). A compound of the formula (37) is reacted with a compound of the formula (38), a known compound or compound prepared by known methods, wherein x is a halogen, in the presence of a solvent such as ethyl ether, tetrahydrofuran, 1,4-dioxane and the like to provide a compound of the formula (39). A compound of the formula (39) is reacted with ruthenium chloride in the presence of sodium periodate in a solvent such as acetonitrile, methanol, ethanol, isopropanol, and the like, to provide a compound of the formula (40). A compound of the formula (40) is reacted with a reducing agent such as lithium borohydride, sodium borohydride, sodium cyanoborohydride and the like, in a solvent such as methanol, ethanol, isopropanol, acetonitrile, and the like to provide a compound of the formula (41). A compound of the formula (41) is then converted to a compound of the formula (42), wherein LG is a mesylate, tosylate, nosylate, and the like, using methods that are known to one skilled in the art. Thus, a compound of the formula (41) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N, N-dimethylformamide, tetrahydrofuran, 1,4-dioxane and the like to provide a compound of the formula (42). A compound of the formula (42) is reacted with a compound of the formula (43), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (44).

Compounds of formula (48) may be prepared according to the process outlined in Scheme 7.

Diethanolamine is reacted with 4-nitrobenzenesulfonyl chloride (NosCl) in the presence of a base such as triethylamine, diisopropylethylamine, pyridine, 2,6-lutidine, and the like in a solvent such as tetrahydrofuran, 1,4-dioxane, methylene chloride and the like to provide a compound of the formula (45). A compound of the formula (45) is then reacted with a compound of the formula (46), a known compound or one prepared by known methods, in the presence of a base such as triethylamine, diisopropylethylamine, pyridine, 2,6-lutidine, and the like, in a solvent such as acetonitrile, methanol, ethanol, dimethyl formamide, optionally with heating, optionally with microwave irradiation to provide a compound of the formula (47). A compound of the formula (47) is reacted with a thiophenol in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, acetonitrile and the like, optionally in the presence of dimethylsulfoxide, optionally with heating, optionally with microwave irradiation, to provide a compound of the formula (48).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

The practice of the invention is illustrated by the following non-limiting examples. The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

In the examples that follow, $^1$H-NMR spectra were obtained on a Varian Mercury 300-MHz NMR. Purity (%)

and mass spectral data were determined with a Waters Alliance 2695 HPLC/MS (Waters Symmetry C18, 4.6×75 mm, 3.5 m) with a 2996 diode array detector from 210-400 nm.

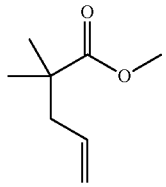

Preparation of methyl 2,2-dimethylpent-4-enoate: This reaction was performed in oven-dried glassware under a nitrogen atmosphere. To a well-stirred solution of freshly prepared lithium diisopropylammide (1M, 1.10 equiv) in dry 35 ml tetrahydrofuran, isobutyric acid methyl ester (3.32 g, 32.6 mmol, 1.0 equiv) was added dropwise during 0.5 hours at −78° C. The mixture was allowed to stir at this temperature for 30 min followed by the addition of allyl bromide (5.35 g, 44.0 mmol) and Hexamethylphosphoramide (HMPA) (2.91 g, 16.3 mmol) dropwise over 0.5 h. The reaction mixture was stirred overnight at room temperature, quenched with 10% HCl (while cooling in ice bath) until acidic (pH=2). The organic layer was separated and the aqueous layer was extracted with hexanes (3×100 mL). The extract was washed with 10% NaHCO$_3$ (200 mL) and brine (200 mL). The solution was then dried over MgSO$_4$, concentrated in vacuo and distilled to give pure product. $^1$H NMR (400 MHz, CDCl$_3$) δ 5.73 (dd, J=9.4, 17.7, 1H), 5.04 (dd, J=1.9, 13.5, 2H), 4.12 (q, J=7.1, 2H), 2.28 (d, J=7.4, 2H), 1.25 (t, J=7.1, 3H), 1.17 (s, 6H); $^{13}$C NMR (101 MHz, CDCl$_3$) δ 177.42, 134.42, 117.88, 77.68, 77.36, 77.04, 60.35, 44.91, 42.25, 24.92, 14.35

The following compounds can be prepared by the procedure of methyl 2,2-dimethylpent-4-enoate. The skilled practitioner will know how to substitute the appropriate reagents, starting materials and purification methods known to those skilled in the art, in order to prepare the compounds provided herein.

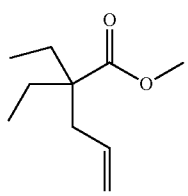

Preparation of Ethyl 2,2-diethylpent-4-enoate: The title compound was prepared according to the procedure for methyl 2,2-dimethylpent-4-enoate, except 2-ethyl-butyric acid ethyl ester was substituted for isobutyric acid methyl ester $^1$H NMR (300 MHz, CDCl$_3$) δ 5.68 (dd, J=9.9, 17.2, 1H), 5.16-4.97 (m, 2H), 4.14 (q, J=7.1, 2H), 2.33 (d, J=7.4, 2H), 1.59 (dt, J=6.5, 7.5, 5H), 1.26 (t, J=7.1, 3H), 0.80 (t, J=7.5, 6H)

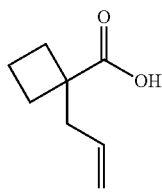

Preparation of 1-allylcyclobutanecarboxylic acid: This reaction was performed in oven-dried glassware under a nitrogen atmosphere. To a well-stirred solution of freshly prepared lithium diisopropylammide (1M, 10.76 mmol, 2.30 equiv) in dry 107 ml tetrahydrofuran, cyclobutanecarboxylic acid (4.68 g, 46.8 mmol, 1.0 equiv) was added dropwise during 0.5 hours at 0° C. The mixture was heated to 50° C. for 6 hours, then cooled to 0° C. followed by the addition of NaI (0.697 g, 4.68 mmol, 0.1 equiv) in one portion and a mixture of allyl bromide (7.58 g, 63.2 mmol, 1.35 equiv) and HMPA (4.18 g, 23.4 mmol, 0.5 equiv) dropwise over 0.5 hr. The reaction mixture was stirred overnight at room temperature, quenched with 10% HCl (while cooling in ice bath) until acidic (pH=2). The organic layer was separated and the aqueous layer was extracted with ether (3×250 mL). The organic phases were combined and washed with brine. The solution was then dried over MgSO$_4$ and concentrated in vacuo to afford a crude oil which was purified through flash chromatography (silica; ethyl acetate/hexanes, 1%-10%). $^1$H NMR (400 MHz, CDCl$_3$) δ 5.77 (ddt, J=7.1, 10.2, 17.2, 1H), 5.17-4.99 (m, 2H), 2.59-2.38 (m, 4H), 2.07-1.84 (m, 4H). $^{13}$C NMR (101 MHz, CDCl$_3$) δ 184.04, 133.90, 118.19, 47.20, 41.74, 29.57, 15.65; Rf, 0.43 (Hexane:Ethyl Acetate 10:1); HRMS (CI): [M+H], calcd for C$_8$H$_{13}$O$_2$, 141.0916; found 141.0911.

The following compounds can be prepared by the procedure of 1-allylcyclobutanecarboxylic acid. The skilled practitioner will know how to substitute the appropriate reagents, starting materials and purification methods known to those skilled in the art, in order to prepare the compounds provided herein.

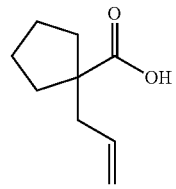

Preparation of 1-allylcyclopentanecarboxylic acid: The title compound was prepared according to the procedure for 1-allylcyclobutanecarboxylic acid, except cyclopentane carboxylic acid was substituted for cyclobutanecarboxylic acid: $^1$H NMR (400 MHz, CDCl$_3$) δ 5.77 (ddt, J=7.2, 10.2, 17.4, 1H), 5.17-4.94 (m, 2H), 2.38 (d, J=7.2, 2H), 2.20-2.02 (m, 2H), 1.79-1.47 (m, 6H). $^{13}$C NMR (101 MHz, CDCl$_3$) δ 184.94, 134.96, 118.02, 53.75, 42.96, 35.89, 25.47. Rf, 0.50 (Hexane:Ethyl Acetate 10:1); HRMS (CI): [M+H], calcd for C$_9$H$_{15}$O$_2$, 155.1072; found 155.1068.

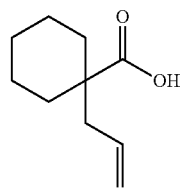

Preparation of 1-allylcyclohexanecarboxylic acid: The title compound was prepared according to the procedure for 1-allylcyclobutanecarboxylic acid, except cyclohexane carboxylic acid was substituted for cyclobutanecarboxylic acid: $^1$H NMR (400 MHz, CDCl$_3$) δ 12.13 (broad, 1H), 5.83-5.63

(m, 1H), 5.12-5.00 (m, 2H), 2.27 (m, 2H), 2.04 (m, 2H), 1.66-1.50 (m, 3H), 1.49-1.33 (m, 2H), 1.33-1.17 (m, 3H)

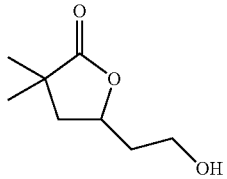

Preparation of 5-(2-Hydroxy-ethyl)-3,3-dimethyl-dihydro-furan-2-one: A mixture of glacial acetic acid (28.6 g, 477 mmol, 53.6 equiv), paraformaldehyde (0.80 g, 26.7 mmol, 3.0 equiv) and $H_2SO_4$ (0.5 g, 4.45 mmol, 0.57 equiv) was stirred for 30 min at 70° C. before methyl 2,2-dimethylpent-4-enoate (1.26 g, 8.9 mmol, 1.0 equiv) was added dropwise during 10 min. The reaction mixture was then maintained at 70-80° C. and allowed to stir overnight. Acetic acid was removed under reduced pressure and the reaction was quenched with 10% $NaHCO_3$ solution. The mixture was then extracted with ethyl acetate (3×50 mL) and the combined organic phase was concentrated in vacuo to give a crude oil. The crude oil was used for next step without further purification.

A mixture of the crude oil (200 mg, 1.0 mmol, 1 equiv) and 30% NaOH (800 mg NaOH, 20 mmol, 20 equiv) aqueous solution was refluxed for 2 hours. The mixture was cooled in an ice bath and excess 30% $H_2SO_4$ was added until acidic (pH<2). The resulting mixture was extracted with ethyl acetate (3×25 mL), the combined organic phase was washed with 10% $NaHCO_3$, (50 mL), brine (50 mL), dried over $MgSO_4$ and concentrated in vacuo to give a crude product which was further purified by column chromatography (Ethyl acetate/Hexanes, 10%-60%) $^1$H NMR (400 MHz, $CDCl_3$) δ 4.70-4.60 (m, 1H), 3.90-3.78 (m, 2H), 2.22 (dd, J=5.9, 12.7, 1H), 1.98-1.87 (m, 2H), 1.80 (dd, J=5.9, 12.7, 1H), 1.28 (d, J=4.8, 6H). $^{13}$C NMR (101 MHz, $CDCl_3$) δ 182.26, 75.01, 59.58, 43.93, 40.62, 38.69, 25.31, 24.61; Rf, 0.34 (Hexane:Ethyl Acetate 1:1); Anal. Calcd for $C_8H_{14}O_3$: C, 60.74; H, 8.92. Found: C, 60.47; H, 8.86.

The following compounds can be prepared by the procedure of 5-(2-Hydroxy-ethyl)-3,3-dimethyl-dihydro-furan-2-one. The skilled practitioner will know how to substitute the appropriate reagents, starting materials and purification methods known to those skilled in the art, in order to prepare the compounds provided herein.

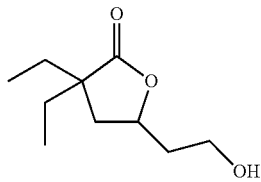

Preparation of 3,3-diethyl-5-(2-hydroxyethyl)dihydro-furan-2(3H)-one: The title compound was prepared according to the procedure for 5-(2-Hydroxy-ethyl)-3,3-dimethyl-dihydro-furan-2-one, except ethyl 2,2-diethylpent-4-enoate was substituted for methyl 2,2-dimethylpent-4-enoate: $^1$H NMR (400 MHz, $CDCl_3$) δ 4.62 (dtd, J=5.3, 7.3, 9.5, 1H), 3.78 (t, J=6.1, 2H), 3.20 (s, 1H), 2.19 (dd, J=6.8, 13.1, 1H), 1.97-1.81 (m, 3H), 1.70-1.56 (m, 4H), 0.93 (dt, J=7.5, 20.7, 6H); $^{13}$C NMR (101 MHz, $CDCl_3$) δ 181.46, 75.10, 58.91, 48.77, 39.13, 37.76, 29.21, 28.30, 8.83, 8.73; Rf, 0.36 (Hexane:Ethyl Acetate 5:2); Anal. Calcd for $C_{10}H_{18}O_3$: C, 64.49; H, 9.74. Found: C, 64.20; H, 9.57.

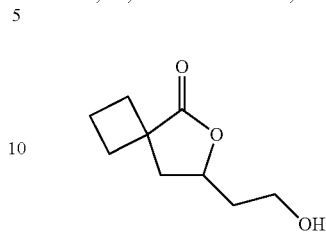

Preparation of 7-(2-hydroxyethyl)-6-oxaspiro[3.4]octan-5-one: The title compound was prepared according to the procedure for 5-(2-Hydroxy-ethyl)-3,3-dimethyl-dihydro-furan-2-one, except 1-allylcyclobutanecarboxylic acid was substituted for methyl 2,2-dimethylpent-4-enoate: $^1$H NMR (400 MHz, $CDCl_3$) δ 4.60-4.50 (m, 1H), 3.82 (t, J=5.9, 2H), 2.61-2.40 (m, 3H), 2.19-1.96 (m, 5H). 1.92-185 (m, 2H); $^{13}$C NMR (101 MHz, $CDCl_3$) δ 181.25, 75.46, 59.66, 44.62, 42.42, 38.47, 31.95, 29.64, 16.79; Rf, 0.40 (Hexane:Ethyl Acetate 1:2); calcd for $C_9H_{15}O_3$, 171.1021; found 171.1016.

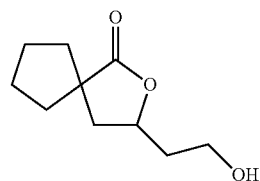 [SMILES: O=C1OC(CCO)CC12CCCC2]

Preparation of 3-(2-hydroxyethyl)-2-oxaspiro[4.4]nonan-1-one: The title compound was prepared according to the procedure for 5-(2-Hydroxy-ethyl)-3,3-dimethyl-dihydro-furan-2-one, except 1-allylcyclopentanecarboxylic acid was substituted for methyl 2,2-dimethylpent-4-enoate: $^1$H NMR (400 MHz, $CDCl_3$) δ 4.65-4.56 (m, 1H), 3.84-3.76 (m, 2H), 2.74 (s, 1H), 2.28 (dd, J=5.8, 12.6, 1H), 2.20-2.10 (m, 1H), 2.00-1.56 (m, 10H); $^{13}$C NMR (101 MHz, $CDCl_3$) δ 183.02, 75.77, 59.20, 50.35, 43.41, 38.41, 37.49, 36.93, 25.67, 25.58; Rf, 0.46 (Hexane:Ethyl Acetate 1:2); HRMS (CI): [M+H], calcd for $C_{10}H_{17}O_3$, 185.1178; found 185.1171.

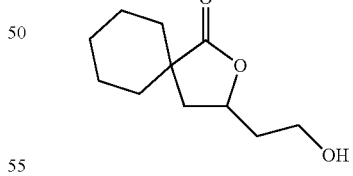

Preparation of 3-(2-hydroxyethyl)-2-oxaspiro[4.5]decan-1-one: The title compound was prepared according to the procedure for 5-(2-Hydroxy-ethyl)-3,3-dimethyl-dihydro-furan-2-one, except 1-allylcyclohexanecarboxylic acid was substituted for methyl 2,2-dimethylpent-4-enoate: $^1$H NMR (400 MHz, $CDCl_3$) δ 4.62 (m, 1H), 3.82 (t, J=5.9, 2H), 2.43 (dd, J=6.2, 12.9, 1H), 2.22 (s, 1H), 2.00-1.17 (m, 13H). $^{13}$C NMR (101 MHz, $CDCl_3$) δ 181.96, 75.37, 59.55, 45.13, 39.88, 38.91, 34.54, 31.71, 25.57, 22.42, 22.36; Rf, 0.46 (Hexane:Ethyl Acetate 1:2); Anal. Calcd for $C_{11}H_{18}O_3$: C, 66.64; H, 9.15. Found: C, 66.48; H, 9.17.

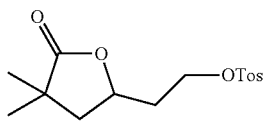

Preparation of 2-(4,4-dimethyl-5-oxotetrahydrofuran-2-yl)ethyl 4-methylbenzenesulfonate: To a stirred solution of 5-(2-Hydroxy-ethyl)-3,3-dimethyl-dihydro-furan-2-one (0.316 g, 2 mmol, 1.0 equiv) and Et$_3$N (0.152 g, 1.5 mmol, 1.5 equiv) in dry dichloromethane, a solution of p-TosCl (0.475 g, 2.5 mmol, 1.25 equiv) in dichloromethane was added drop wise at 0° C. The resulting mixture was stirred at 0° C. for 1 hour and allowed to stir overnight at room temperature. Then, the reaction mixture was diluted with dichloromethane (50 mL), washed with 10% HCl, brine, dried over MgSO$_4$ and concentrated in vacuo to afford yellowish oil. This crude product was then purified by flash chromatography (silica gel; Ethyl acetate/Hexanes, 0%-40%) to afford desired tosylate. $^1$H NMR (300 MHz, CDCl$_3$) δ 7.72 (m, 2H), 7.29 (m, 2H), 4.39 (m, 1H), 4.10 (m, 2H), 2.38 (s, 3H), 2.09 (m, 1H), 1.93 (m, 2H), 1.65 (m, 1H), 1.16 (d, J=4.8, 6H); $^{13}$C NMR (101 MHz, CDCl$_3$)$^{13}$C NMR (101 MHz, CDCl$_3$) δ 181.26, 145.16, 132.53, 130.03, 127.84, 77.68, 77.36, 77.04, 72.93, 66.83, 42.99, 40.23, 34.97, 24.82, 24.12, 21.57; HRMS (CI): [M+H]313.1; Anal. Calcd for C$_{15}$H$_{20}$O$_5$S: C, 57.67; H, 6.45. Found: C, 57.85; H, 6.63.

The following compounds can be prepared by the procedure of 2-(4,4-dimethyl-5-oxotetrahydrofuran-2-yl)ethyl 4-methylbenzenesulfonate. The skilled practitioner will know how to substitute the appropriate reagents, starting materials and purification methods known to those skilled in the art, in order to prepare the compounds provided herein.

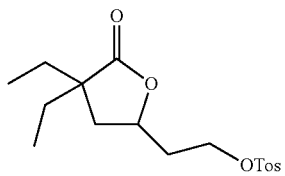

Preparation of 2-(4,4-diethyl-5-oxotetrahydrofuran-2-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3,3-diethyl-5-(2-hydroxyethyl)dihydrofuran-2(3H)-one was substituted for 5-(2-Hydroxy-ethyl)-3,3-dimethyl-dihydro-furan-2-one: $^1$H NMR (300 MHz, CDCl$_3$) δ 7.79 (d, J=8.3 Hz, 2H), 7.36 (d, J=8.0 Hz, 2H), 4.55-4.33 (m, 1H), 4.14 (dd, J=6.5, 13.3 Hz, 3H), 2.46 (s, 3H), 2.21-1.84 (m, 3H), 1.83-1.68 (m, 1H), 1.58 (t, J=7.4 Hz, 4H), 0.89 (dt, J=7.5, 18.0 Hz, 6H); $^{13}$C NMR (101 MHz, CDCl$_3$) δ 180.33, 145.30, 132.72, 130.15, 128.03, 77.68, 77.36, 77.04, 73.18, 66.95, 48.67, 37.53, 35.82, 29.14, 28.23, 21.76, 8.81, 8.74. Anal. Calcd for C$_{17}$H$_{24}$O$_5$S: C, 59.98; H, 7.11. Found: C, 60.27; H, 7.25.

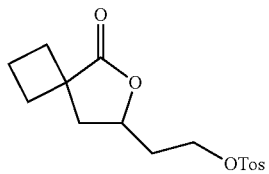

Preparation of 2-(5-oxo-6-oxaspiro[3.4]octan-7-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 7-(2-hydroxyethyl)-6-oxaspiro[3.4]octan-5-one was substituted for 5-(2-Hydroxy-ethyl)-3,3-dimethyl-dihydro-furan-2-one: $^1$H NMR (400 MHz, CDCl$_3$) δ 7.77 (d, J=8.3 Hz, 2H), 7.35 (d, J=8.0 Hz, 2H), 4.37 (tdd, J=8.8, 6.0, 4.3 Hz, 1H), 4.21-4.05 (m, 2H), 2.57-2.32 (m, 6H), 2.19-1.82 (m, 7H); $^{13}$C NMR (101 MHz, CDCl$_3$) δ 180.41, 145.24, 132.68, 130.10, 128.02, 73.38, 66.76, 44.33, 41.79, 35.10, 31.72, 29.28, 21.76, 16.51.

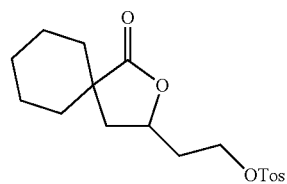

Preparation of 2-(1-oxo-2-oxaspiro[4.4]nonan-3-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3-(2-hydroxyethyl)-2-oxaspiro[4.4]nonan-1-one was substituted for 5-(2-Hydroxy-ethyl)-3,3-dimethyl-dihydro-furan-2-one: $^1$H NMR (400 MHz, CDCl$_3$) δ 7.79 (d, J=8.3 Hz, 2H), 7.36 (d, J=8.0 Hz, 2H), 4.51-4.35 (m, 1H), 4.25-4.06 (m, 2H), 2.45 (s, 3H), 2.28-2.08 (m, 2H), 2.08-1.91 (m, 2H), 1.87-1.52 (m, 9H); $^{13}$C NMR (101 MHz, CDCl$_3$) δ 181.90, 145.26, 132.76, 130.12, 128.07, 73.71, 66.85, 50.19, 43.07, 37.44, 36.81, 35.19, 25.61, 25.50, 21.79.

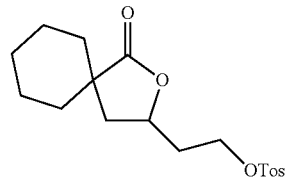

Preparation of 2-(1-oxo-2-oxaspiro[4.5]decan-3-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3-(2-hydroxyethyl)-2-oxaspiro[4.5]decan-1-one was substituted for 5-(2-Hydroxy-ethyl)-3,3-dimethyl-dihydro-furan-2-one: $^1$H NMR (400 MHz, CDCl$_3$) δ 7.79 (d, J=8.3 Hz, 2H), 7.36 (d, J=8.0 Hz, 2H), 4.51-4.38 (m, 1H), 4.26-4.12 (m, 2H), 2.45 (s, 3H), 2.36 (dd, J=12.9, 6.2 Hz, 1H), 2.12-1.87 (m, 2H), 1.85-1.68 (m, 3H), 1.65-1.50 (m, 5H), 1.43-1.14 (m, 3H); $^{13}$C NMR (101 MHz, CDCl$_3$) δ 180.97, 145.27, 132.76, 130.12, 128.07, 73.28, 66.85, 44.96, 39.48, 35.58, 34.35, 31.52, 25.37, 22.23, 22.16, 21.80.

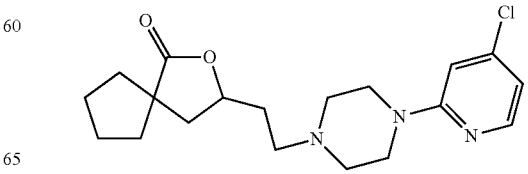

Preparation of 3-(2-(4-(4-chloropyridin-2-yl)piperazin-1-yl)ethyl)-2-oxaspiro[4.4]nonan-1-one: To a small vial, 2-(1-oxo-2-oxaspiro[4.4]nonan-3-yl)ethyl 4-methylbenzenesulfonate (50 mg, 0.15 mmol, 1.0 equiv) was added and dissolved in 5 mL tetrahydrofuran. 1-(4-chloropyridin-2-yl)piperazine (58 mg, 0.30 mmol, 2.0 equiv) was then added. The reaction was stirred at 60° C. for 3 days. The solution was allowed to cool to room temperature and was then diluted with deionized water (5 mL) and ethyl acetate (5 mL). The layers were separated and the aqueous layer was washed 2×5 mL ethyl acetate. The organic layers were combined and dried over $Na_2SO_4$ and then concentrated under reduced pressure. The resulting crude oil was purified through flash chromatography (silica gel; methanol/dichloromethane, 0-10%). $^1$H NMR (400 MHz, Chloroform-d) δ 7.96 (d, J=6.0 Hz, 1H), 6.58 (d, J=2.3 Hz, 1H), 6.50 (dd, J=6.0, 2.3 Hz, 1H), 4.42 (m, 1H), 3.29 (br, 4H), 2.53 (br, 6H), 2.18 (m, 2H), 1.85-1.55 (m, 10H). LC/MS M+1=364.20.

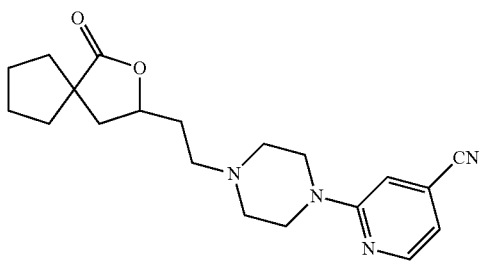 [SMILES: N#Cc1ccnc(N2CCN(CCC3CC4(CCCC4)C(=O)O3)CC2)c1]

Preparation of 2-(4-(2-(1-oxo-2-oxaspiro[4.4]nonan-3-yl)ethyl)piperazin-1-yl)isonicotinonitrile: The title compound was prepared according to the procedure for 3-(2-(4-(4-chloropyridin-2-yl)piperazin-1-yl)ethyl)-2-oxaspiro[4.4]nonan-1-one except 2-(piperazin-1-yl)isonicotinonitrile was substituted for 1-(4-chloropyridin-2-yl)piperazine. $^1$H NMR (400 MHz, Chloroform-d) δ 8.21 (d, 5.0 Hz, 1H), 6.73 (s, 1H), 6.69 (d, J=5.0 Hz, 1H), 4.42 (m, 1H), 3.52 (br, 4H), 4.50 (br, 6H), 2.19 (m, 2H), 1.79-1.56 (m, 10H). LC/MS M+1=355.20.

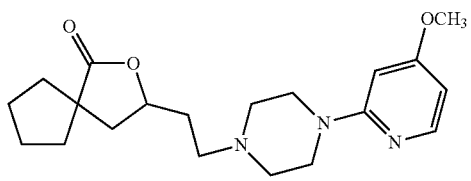 [SMILES: COc1ccnc(N2CCN(CCC3CC4(CCCC4)C(=O)O3)CC2)c1]

Preparation of 3-(2-(4-(4-methoxypyridin-2-yl)piperazin-1-yl)ethyl)-2-oxaspiro[4.4]nonan-1-one: The title compound was prepared according to the procedure for 3-(2-(4-(4-chloropyridin-2-yl)piperazin-1-yl)ethyl)-2-oxaspiro[4.4]nonan-1-one except 1-(4-methoxypyridin-2-yl)piperazine was substituted for 1-(4-chloropyridin-2-yl)piperazine. $^1$H NMR (400 MHz, Chloroform-d) δ 7.97 (d, J=5.8 Hz, 1H), 6.20 (dd, J=5.8, 2.0 Hz, 1H), 6.03 (d, J=2.0 Hz, 1H), 4.42 (m, 1H), 3.74 (s, 3H), 3.46 (br, 4H), 2.50 (br, 6H), 2.18 (m, 2H), 1.8-1.6 (m, 10H). LC/MS M+1=360.20.

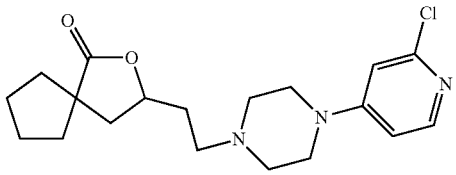 [SMILES: O=C1OC(CCN2CCN(c3ccnc(Cl)c3)CC2)CC12CCCC2]

Preparation of 3-(2-(4-(2-chloropyridin-4-yl)piperazin-1-yl)ethyl)-2-oxaspiro[4.4]nonan-1-one: The title compound was prepared according to the procedure for 3-(2-(4-(4-chloropyridin-2-yl)piperazin-1-yl)ethyl)-2-oxaspiro[4.4]nonan-1-one except 1-(2-chloropyridin-4-yl)piperazine was substituted for 1-(4-chloropyridin-2-yl)piperazine. $^1$H NMR (400 MHz, Chloroform-d) δ 8.19 (d, J=6.5 Hz, 1H), 6.71 (d, J=2.5 Hz, 1H), 6.68 (dd, J=6.5, 2.5 Hz, 1H), 4.36 (m, 1H), 3.76 (br, 4H), 3.30 (br, 6H), 2.26 (m, 2H), 1.80-1.52 (m, 10H). LC/MS M+1=364.20.

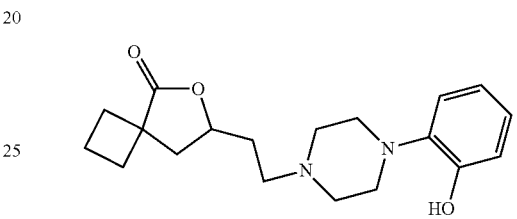

Preparation of 7-(2-(4-(2-hydroxyphenyl)piperazin-1-yl)ethyl)-6-oxaspiro[3.4]octan-5-one: To a small vial, 2-(5-oxo-6-oxaspiro[3.4]octan-7-yl)ethyl 4-methylbenzenesulfonate (50 mg, 0.15 mmol, 1.0 equiv) was added and dissolved in 5 mL tetrahydrofuran. 2-(piperazin-1-yl)phenol (27.54 mg, 0.15 mmol, 1.0 equiv) was added along with 30 µL of triethylamine (0.21 mmol, 1.4 equiv). The reaction was stirred at 60° C. for 3 days. The solution was allowed to cool to room temperature and was then diluted with deionized water (5 mL) and ethyl acetate (5 mL). The layers were separated and the aqueous layer was washed 2×5 mL ethyl acetate. The organic layers were combined and dried over $Na_2SO_4$ and then concentrated under reduced pressure. The resulting crude oil was purified through flash chromatography (silica gel; methanol/dichloromethane, 0-10%). $^1$H NMR (400 MHz, Chloroform-d) δ 7.09 (m, 2H), 6.89 (dd, J=8.2, 1.2 Hz, 1H), 6.85 (td, J=7.5 1.2 Hz, 1H), 4.34 (m, 1H), 3.70 (b, 4H), 3.27-3.14 (m, 6H), 2.51 (m, 2H), 2.37 (m, 1H), 2.19 (m, 1H), 2.1-1.9 (m, 6H). LC/MS M+1=331.20.

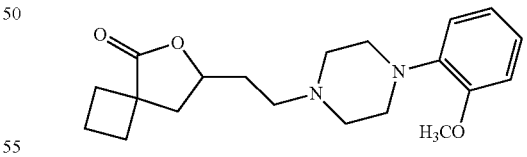

Preparation of 7-(2-(4-(2-methoxyphenyl)piperazin-1-yl)ethyl)-6-oxaspiro[3.4]octan-5-one: The title compound was prepared according to the procedure for 7-(2-(4-(2-hydroxyphenyl)piperazin-1-yl)ethyl)-6-oxaspiro[3.4]octan-5-one except 1-(2-methoxyphenyl)piperazine was substituted for 2-(piperazin-1-yl)phenol. $^1$H NMR (400 MHz, Chloroform-d) δ 7.19 (td, J=8.0, 1.5 Hz, 1H), 7.07 (dd, J=8.0, 1.5 Hz, 1H), 7.00 (td, J=8.0, 1.0 Hz, 1H), 6.95 (dd, J=8.0, 1.0 Hzm 1H), 4.41 (m, 1H), 3.90 (s, 3H), 3.8-3.2 (br, 10H), 2.58 (m, 2H), 2.45 (m, 1H), 2.24 (m, 1H), 2.20-2.00 (m, 6H). LC/MS M+1=345.20.

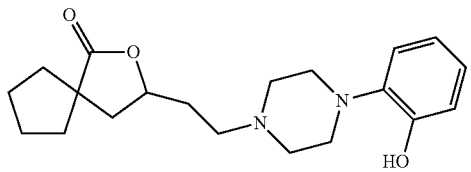 [SMILES: O=C1OC(CCN2CCN(c3ccccc3O)CC2)CC12CCCC2]

Preparation of 3-(2-(4-(2-hydroxyphenyl)piperazin-1-yl) ethyl)-2-oxaspiro[4.4]nonan-1-one: The title compound was prepared according to the procedure for 7-(2-(4-(2-hydroxyphenyl)piperazin-1-yl)ethyl)-6-oxaspiro[3.4]octan-5-one except 2-(1-oxo-2-oxaspiro[4.4]nonan-3-yl)ethyl 4-methylbenzenesulfonate was substituted for 2-(5-oxo-6-oxaspiro[3.4]octan-7-yl)ethyl 4-methylbenzenesulfonate. $^1$H NMR (400 MHz, Chloroform-d) δ 7.07 (m, 2H), 6.88 (dd, J=8.0, 0.8 Hz, 1H), 6.84 (td, J=7.7, 0.8 Hz, 1H), 4.38 (m, 1H), 3.69 (br, 4H), 3.35-3.05 (br, 6H), 2.22 (m, 2H), 2.08 (m, 2H), 1.80 (m, 4H), 1.63 (m, 3H), 1.56 (m, 1H). LC/MS M+1=345.20.

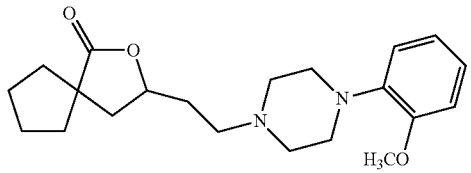 [SMILES: COc1ccccc1N1CCN(CCC2CC3(CCCC3)C(=O)O2)CC1]

Preparation of 3-(2-(4-(2-methoxyphenyl)piperazin-1-yl) ethyl)-2-oxaspiro[4.4]nonan-1-one: The title compound was prepared according to the procedure for 7-(2-(4-(2-hydroxyphenyl)piperazin-1-yl)ethyl)-6-oxaspiro[3.4]octan-5-one except 2-(1-oxo-2-oxaspiro[4.4]nonan-3-yl)ethyl 4-methylbenzenesulfonate was substituted for 2-(5-oxo-6-oxaspiro[3.4]octan-7-yl)ethyl 4-methylbenzenesulfonate and 1-(2-methoxyphenyl)piperazine was substituted for 2-(piperazin-1-yl)phenol. $^1$H NMR (400 MHz, Chloroform-d) δ 7.11 (td, J=8.0, 1.5 Hz, 1H), 6.99 (dd, J=8.0, 1.5 Hz, 1H), 6.90 (td, J=7.8, 1.2 Hz, 1H), 6.87 (dd, J=8.2, 1.2 Hz, 1H), 4.37 (m, 1H), 3.81 (s, 3H), 3.78-3.20 (br, 10H), 2.20 (m, 2H), 2.05 (m, 2H), 1.78 (m, 4H), 1.62 (m, 3H), 1.55 (m, 1H). LC/MS M+1=359.20.

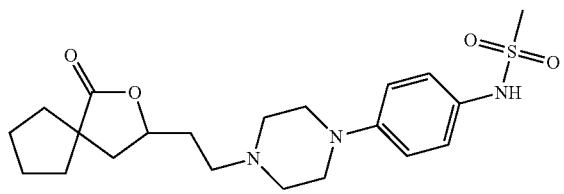 [SMILES: CS(=O)(=O)Nc1ccc(N2CCN(CCC3CC4(CCCC4)C(=O)O3)CC2)cc1]

Preparation of N-(4-(4-(2-(1-oxo-2-oxaspiro[4.4]nonan-3-yl)ethyl)piperazin-1-yl)phenyl)methanesulfonamide: The title compound was prepared according to the procedure for 7-(2-(4-(2-hydroxyphenyl)piperazin-1-yl)ethyl)-6-oxaspiro[3.4]octan-5-one except 2-(1-oxo-2-oxaspiro[4.4]nonan-3-yl)ethyl 4-methylbenzenesulfonate was substituted for 2-(5-oxo-6-oxaspiro[3.4]octan-7-yl)ethyl 4-methylbenzenesulfonate and N-(4-(piperazin-1-yl)phenyl)methanesulfonamide was substituted for 2-(piperazin-1-yl)phenol. $^1$H NMR (400 MHz, Chloroform-d) δ 7.07 (d, J=8.9 Hz, 2H), 6.81 (d, J=8.9 Hz, 2H), 4.40 (m, 1H), 3.11 (m, 4H), 2.87 (s, 3H), 2.49 (br, 6H), 2.17 (m, 2H), 1.90-1.60 (m, 10H). LC/MS M+1=422.2.

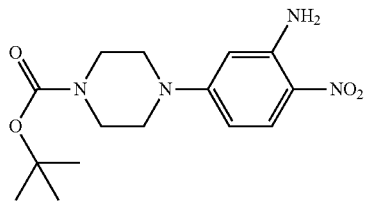 [SMILES: CC(C)(C)OC(=O)N1CCN(c2ccc([N+](=O)[O-])c(N)c2)CC1]

Preparation of Tert-butyl 4-(3-amino-4-nitrophenyl) piperazine-1-carboxylate: To a solution of 5-chloro-2-nitrobenzenamine (1.5 g, 8.6 mmol) in 15 mL N, N-dimethyl acetamide, tert-butyl piperazine-1-carboxylate (2.4 g, 13.0 mmol) and potassium carbonate (3.6 g, 26 mmol) were added and stirred at 140° C. for 18 hours. The reaction was cooled to room temperature and filtered. The filtrate was concentrated to an oil under reduced pressure. The oil was diluted with water (200 mL) and filtered. The precipitate was washed with ether (50 mL) and dried under high vacuum to yield (1.57 g, 56%) of 1 as yellow solid. $^1$H NMR (400 MHz, Chloroform-d) δ 8.03 (d, J=9.6 Hz, 1H), 6.25 (dd, J=9.6 Hz, J=2.6 Hz, 1H)), 6.17 (bs, 2H), 5.93 (d, J=2.6 Hz, 1H), 3.56 (t, J=5.5 Hz, 4H), 3.35 (t, J=5.5 Hz, 4H), 1.48 (s, 9H). LC/MS M+1=323.2.

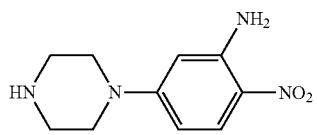 [SMILES: Nc1cc(N2CCNCC2)ccc1[N+](=O)[O-]]

Preparation of 2-nitro-5-(piperazin-1-yl) benzenamine: To a solution of tert-butyl 4-(3-amino-4-nitrophenyl) piperazine-1-carboxylate (0.1 g, 0.31 mmol) in 20 mL Dichloromethane, 2 mL trifluroacetic acid was added and the reaction was stirred at 1 hour. The solvent was removed under reduced pressure. The oil obtained was dissolved in 20 mL methanol and amberlite IRA-400(OH) resin (1 g) was added and stirred for 30 min. The resin was filtered and the solvent was removed under vacuum to a solid (0.030 g, 45%). LC/MS M+1=223.2.

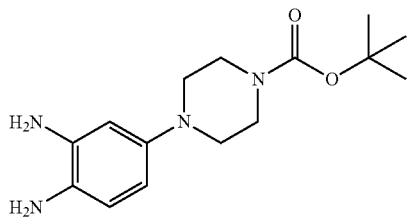 [SMILES: CC(C)(C)OC(=O)N1CCN(c2ccc(N)c(N)c2)CC1]

Preparation of Tert-butyl 4-(3, 4-diaminophenyl) piperazine-1-carboxylate

To a solution of tert-butyl 4-(3-amino-4-nitrophenyl) piperazine-1-carboxylate (1 g, 3.1 mmol) in 50 mL methanol 10% Pd/C (0.2 g) was added and stirred under a hydrogen gas at atmospheric pressure for 20 hours. The reaction mixture was filtered through a patch of celite and the solvent was removed under reduced pressure to a solid (0.7 g, 77%). $^1$H NMR (400 MHz, Chloroform-d) δ 6.57 (d, J=8.3 Hz, 1H), 6.28 (d, J=2.5 Hz, 1H), 6.24 (dd, J=8.3 Hz, J=2.5 Hz, 1H), 3.49 (t, J=4.9 Hz, 4H), 2.90 (t, J=4.8 Hz, 4H), 1.40 (s, 9H). LC/MS M+1=293.2.

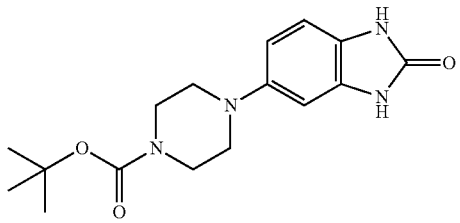 [SMILES: CC(C)(C)OC(=O)N1CCN(c2ccc3[nH]c(=O)[nH]c3c2)CC1]

Preparation of Tert-butyl 4-(2, 3-dihydro-2-oxo-1H-benzo[d]imidazol-6-yl) piperazine-1-carboxylate: To a solution of tert-butyl 4-(3,4-diaminophenyl)piperazine-1-carboxylate (0.44 g, 1.50 mmol) in 25 mL dichloromethane imidazole (0.27 g, 1.65 mmol) triethylamine (0.45 g, 4.5 mmol) were added and stirred for 18 hours. The solvent was removed under reduced pressure and the oil obtained was purified by flash chromatography to a solid (0.17 g, 36%). $^1$H NMR (400 MHz, Chloroform-d) δ 8.0 (s, 1H), 7.8 (s, 1H), 6.85 (d, J=8.4 Hz, 1H), 6.62 (dd, J=8.4 Hz, J=2.52 Hz, 1H), 6.60 (s, 1H), 3.51 (t, J=4.9 Hz, 4H), 2.96 (t, J=5.2 Hz, 4H), 1.42 (s, 9H). LC/MS M+1=319.2.

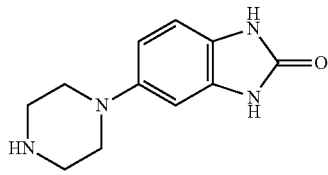 [SMILES: O=c1[nH]c2ccc(N3CCNCC3)cc2[nH]1]

Preparation of 5-(piperazin-1-yl)-1H-benzo[d]imidazol-2(3H)-one: To a solution of tert-butyl 4-(2,3-dihydro-2-oxo-1H-benzo[d]imidazol-6-yl)piperazine-1-carboxylate (0.1 g, 0.31 mmol) in 3 mL Dichloromethane, 1 mL trifluroacetic acid was added and stirred for 2 hours. The solvent was removed under reduced pressure. The oil obtained was dissolved in 30 mL of methanol and Amberlite IRA-400 (OH) resin (1 g) was added and stirred for 15 min. The resin was filtered and the solvent was removed under vacuum to a solid (0.06 g, 92%). $^1$H NMR (400 MHz, DMSO-d$_6$) δ 10.38 (s, 1H), 10.27 (s, 1H), 6.76 (d, J=8.4 Hz, 1H), 6.52 (dd, J=8.4 Hz, J=2.3 Hz, 1H), 6.49 (d, J=2.1 Hz, 1H), 3.88 (m, 4H), 2.81 (m, 4H). LC/MS M+23=241.10.

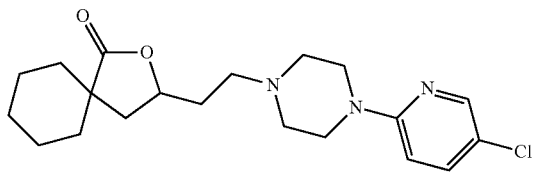 [SMILES: O=C1OC(CCN2CCN(c3ccc(Cl)cn3)CC2)CC12CCCCC2]

Preparation of 3-{2-[4-(5-Chloro-pyridin-2-yl)-piperazin-1-yl]-ethyl}-2-oxa-spiro[4.5]decan-1-one: To a solution of 2-(1-oxo-2-oxaspiro[4.5]decan-3-yl)ethyl 4-methylbenzenesulfonate (0.050 g, 0.15 mmol) in 4 mL Tetrahydrofuran, 1-(5-chloropyridin-2-yl)piperazine (0.073 g, 0.37 mmol) was added and stirred at 60° C. for 48 hours. The precipitate was filtered. The filtrate was concentrated to an oil under reduced pressure. The crude oil was purified by reverse phase flash chromatography using acetonitrile/H$_2$O/0.1% formic acid as eluent (5% acetonitrile to 95% acetonitrile over a 15 minute gradient) to afforded 3-{2-[4-(5-Chloro-pyridin-2-yl)-piperazin-1-yl]-ethyl}-2-oxa-spiro[4.5]decan-1-one (0.027 g, 51%) as an off white solid. $^1$H NMR (400 MHz, Chloroform-d) δ 8.12 (d, J=2.4 Hz, 1H), 7.43 (dd, J=9.0 Hz, J=2.6 Hz, 1H), 6.59 (d, J=9.0 Hz, 1H) 4.52 (m, 1H), 3.53 (pen, J=5.6 Hz, J=1.4 Hz, 4H) 2.57 (m, 4H), 2.54 (m, 2H), 2.43 (m, 1H), 1.86 (m, 4H), 1.69 (m, 6H), 1.35 (m, 3H). LC/MS M+1=378.2.

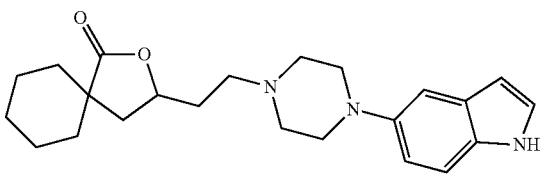 [SMILES: O=C1OC(CCN2CCN(c3ccc4[nH]ccc4c3)CC2)CC12CCCCC2]

Preparation of 3-{2-[4-(1H-Indol-5-yl)-piperazin-1-yl]-ethyl}-2-oxa-spiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-indole was substituted for 1-(5-chloropyridin-2-yl)piperazine. $^1$H NMR (400 MHz, Chloroform-d) δ 8.34 (s, 1H), 8.11 (s, 1H), 7.31 (d, J=8.7 Hz, 1H), 7.19 (d, J=2.4 Hz, 2H), 6.94 (dd, J=9.0 Hz, J=2.2 Hz, 1H), 6.47 (m, 1H), 4.47 (m, 1H), 3.28 (t, J=4.9 Hz, 4H) 2.96 (m, 4H), 2.85 (m, 2H), 2.43 (m, 1H), 2.07 (m, 2H), 1.67 (m, 8H), 1.35 (m, 3H). LC/MS M+1=382.2.

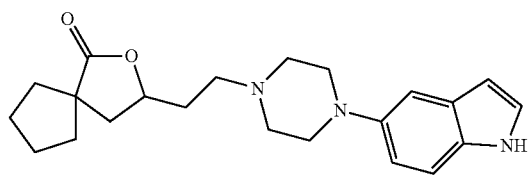 [SMILES: O=C1OC(CCN2CCN(c3ccc4[nH]ccc4c3)CC2)CC12CCCC2]

Preparation of 3-{2-[4-(1H-Indol-5-yl)-piperazin-1-yl]-ethyl}-2-oxa-spiro[4.4]nonan-1-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-indole was substituted for 1-(5-chloropyridin-2-yl)piperazine and 2-(1-oxo-2-oxaspiro[4.4]nonan-3-yl)ethyl 4-methylbenzenesulfonate was substituted for 2-(5-oxo-6-oxaspiro[3.4]octan-7-yl)ethyl 4-methylbenzenesulfonate. $^1$H NMR (400 MHz, Chloroform-d) δ 8.31 (s, 1H), 8.10 (s, 1H), 7.31 (d, J=8.8 Hz, 1H), 7.18 (s, 2H), 6.94 (dd, J=8.7 Hz, J=2.2 Hz, 1H), 6.47 (m, 1H), 4.47 (m, 1H), 3.28 (t, J=4.7 Hz, 4H) 2.96 (m, 4H), 2.86 (m, 2H), 2.27 (m, 1H), 2.07 (m, 2H), 1.85 (m, 9H). LC/MS M+1=369.2.

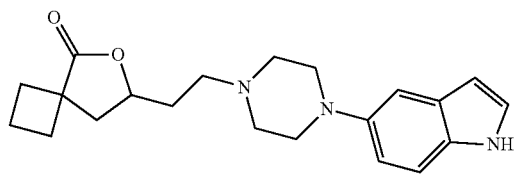 [SMILES: O=C1OC(CCN2CCN(c3ccc4[nH]ccc4c3)CC2)CC12CCC2]

Preparation of 7-{2-[4-(1H-Indol-5-yl)-piperazin-1-yl]-ethyl}-6-oxa-spiro[3.4]octan-5-one: The title compound was prepared according to the procedure for 3-{2-[4-(5-Chloro-pyridin-2-yl)-piperazin-1-yl]-ethyl}-2-oxa-spiro [4.5]decan-1-one except 5-(piperazin-1-yl)-1H-indole was substituted for 1-(5-chloropyridin-2-yl)piperazine and 2-(5-oxo-6-oxaspiro[3.4]octan-7-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 8.09 (s, 1H), 7.75 (s, 1H), 7.32 (d, J=9 Hz, 1H), 7.19 (s, 2H), 6.94 (dd, J=8.8 Hz, J=2.0 Hz, 1H), 6.45 (m, 1H), 4.43 (m, 1H), 3.39 (m, 4H) 3.25 (m, 4H), 2.93 (m, 2H), 2.54 (m, 1H), 2.43 (m, 2H), 2.02 (m, 7H). LC/MS M+1=354.2.

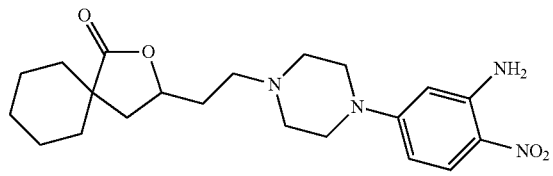 [SMILES: Nc1cc(N2CCN(CCC3CC4(CCCCC4)C(=O)O3)CC2)ccc1[N+](=O)[O-]]

Preparation of 3-(2-(4-(-3-amino-4-nitrophenyl)piperazin-1-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 2-nitro-5-(piperazin-1-yl) aniline was substituted for 1-(5-chloropyridin-2-yl) piperazine. ¹H NMR (400 MHz, Chloroform-d) δ 7.95 (d, J=9.7 Hz, 1H), 6.19 (dd, J=9.7 Hz, J=2.5 Hz, 1H), 6.18 (bs, 2H), 5.89 (d, J=2.5 Hz, 1H), 4.42 (m, 1H), 3.34 (t, J=4.9 Hz, 4H) 2.96 (m, 4H), 2.32 (m, 1H), 1.85 (m, 3H), 1.74 (m, 3H), 1.58 (m, 3H), 1.42 (m, 1H), 1.30 (m, 1H), 1.18 (m, 1H). LC/MS M+1=403.2.

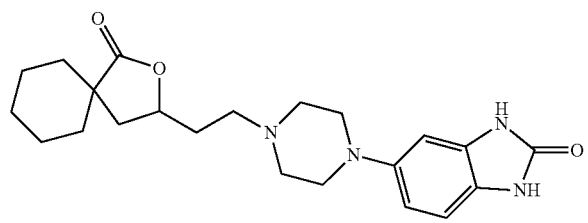 [SMILES: O=C1OC(CCN2CCN(c3ccc4[nH]c(=O)[nH]c4c3)CC2)CC12CCCCC2]

Preparation of 5-(4-(2-(1-oxo-2-oxaspiro[4.5]decan-3-yl) ethyl)piperazin-1-yl)-1H-benzo[d]imidazol-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-benzo[d]imidazol-2(3H)-one was substituted for 1-(5-chloropyridin-2-yl)piperazine. ¹H NMR (400 MHz, Chloroform-d) δ 6.93 (d, J=9.1 Hz, 1H), 6.75 (d, J=2.2 Hz, 1H), 6.74 (d, J=2.2 Hz, 1H), 4.55 (m, 1H), 3.13 (t, J=4.4 Hz, 4H) 2.67 (t, J=4.9 Hz, 4H), 2.52 (m, 1H), 2.50 (m, 2H), 1.93 (m, 2H), 1.74 (m, 6H), 1.52 (m, 3H), 1.34 (m, 2H). LC/MS M+1=399.2.

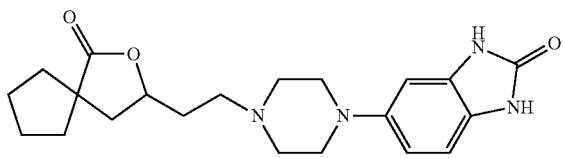 [SMILES: O=C1OC(CCN2CCN(c3ccc4[nH]c(=O)[nH]c4c3)CC2)CC12CCCC2]

Preparation of 5-(4-(2-(1-oxo-2-oxaspiro[4.4]nonan-3-yl) piperazin-1-yl)-1H-benzo[d]imidazol-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-benzo[d]imidazol-2(3H)-one was substituted for 1-(5-chloropyridin-2-yl)piperazine and 2-(1-oxo-2-oxaspiro[4.4] nonan-3-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 6.95 (d, J=9.2 Hz, 1H), 6.77 (d, J=2.2 Hz, 1H), 6.74 (d, J=2.2 Hz, 1H), 4.55 (m, 1H), 3.15 (t, J=4.4 Hz, 4H) 2.67 (t, J=4.9 Hz, 4H), 2.60 (m, 2H), 2.35 (m, 1H), 2.10 (m, 1H), 1.90 (m, 2H), 1.87 (m, 1H), 1.75 (m, 4H), 1.69 (m, 1H). LC/MS M+1=385.2.

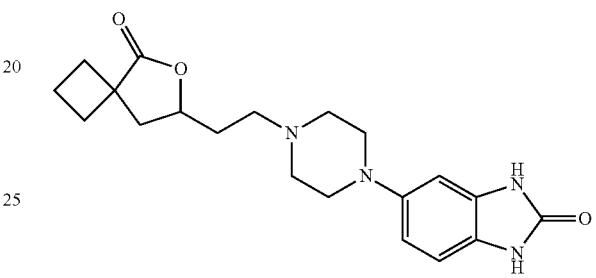

Preparation of 5-(4-(2-(1-oxo-2-oxaspiro[3.4]octan-3-yl) piperazin-1-yl)-1H-benzo[d]imidazol-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-benzo[d]imidazol-2(3H)-one was substituted for 1-(5-chloropyridin-2-yl)piperazine and 2-(5-oxo-6-oxaspiro[3.4] octan-7-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 6.95 (d, J=9.2 Hz, 1H), 6.77 (d, J=1.6 Hz, 1H), 6.75 (d, J=2.2 Hz, 1H), 4.55 (m, 1H), 3.15 (t, J=4.7 Hz, 4H) 2.67 (t, J=4.9 Hz, 4H), 2.50 (m, 4H), 2.07 (m, 4H), 1.92 (m, 4H). LC/MS M+1=371.2.

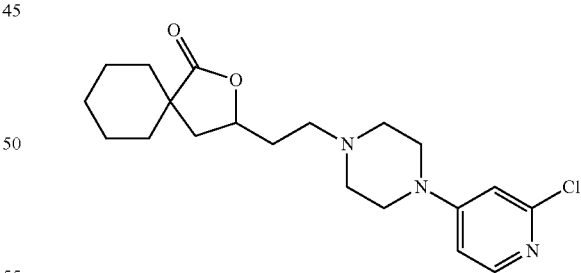

Preparation of 3-(2-(4-(2-chloropyridin-4-yl)piperazin-1-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro [4.5]decan-1-one except 1-(2-chloropyridin-4-yl)piperazine was substituted for 1-(5-chloropyridin-2-yl)piperazine. ¹H NMR (400 MHz, MeOD) δ 7.76 (d, J=6.2 Hz, 1H), 6.69 (d, J=2.2 Hz, 1H), 6.55 (dd, J=6.2 Hz, J=2.3 Hz, 1H), 4.44 (m, 1H), 3.28 (t, J=5.0 Hz, 4H) 2.45 (m, 4H), 2.34 (m, 3H), 1.75 (m, 2H), 1.60 (m, 6H), 1.37 (m, 3H), 1.20 (m, 2H). LC/MS M+1=378.2.

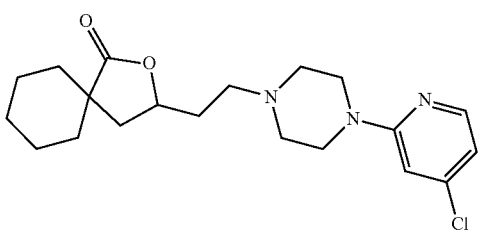 [SMILES: O=C1OC(CCN2CCN(c3cc(Cl)ccn3)CC2)CC12CCCCC2]

Preparation of 3-{2-[4-(4-Chloro-pyridin-2-yl)-piperazin-1-yl]-ethyl}-2-oxa-spiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 1-(4-chloropyridin-2-yl)piperazine was substituted for 1-(5-chloropyridin-2-yl)piperazine. $^1$H NMR (400 MHz, MeOD) δ 7.94 (d, J=6.2 Hz, 1H), 6.86 (d, J=2.3 Hz, 1H), 6.82 (dd, J=6.2 Hz, J=2.4 Hz, 1H), 4.58 (m, 1H), 3.45 (t, J=5.1 Hz, 4H) 2.62 (m, 4H), 2.53 (m, 3H), 1.92 (m, 2H), 1.75 (m, 6H), 1.53 (m, 3H), 1.36 (m, 2H). LC/MS M+1=378.2.

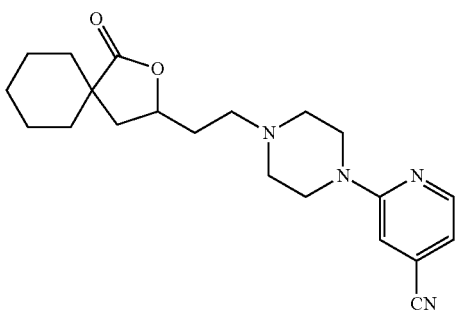 [SMILES: N#Cc1ccnc(N2CCN(CCC3CC4(CCCCC4)C(=O)O3)CC2)c1]

Preparation of 2-(4-(2-(1-oxo-2-oxaspiro[4.5]decan-3-yl)ethyl)piperazin-1-yl)isonicotinonitrile: The title compound was prepared according to the procedure for 3-{2-[4-(5-Chloro-pyridin-2-yl)-piperazin-1-yl]-ethyl}-2-oxa-spiro[4.5]decan-1-one except 2-(piperazin-1-yl)isonicotinonitrile was substituted for 1-(5-chloropyridin-2-yl)piperazine. $^1$H NMR (400 MHz, MeOD) δ 8.27 (d, J=5.0 Hz, 1H), 7.1 (s, 1H), 6.85 (dd, J=5.0 Hz, J=1.0 Hz, 1H), 4.59 (m, 1H), 3.64 (t, J=5.1 Hz, 4H) 2.62 (m, 4H), 2.52 (m, 3H), 1.94 (m, 2H), 1.75 (m, 6H), 1.54 (m, 3H), 1.36 (m, 2H). LC/MS M+1=369.2.

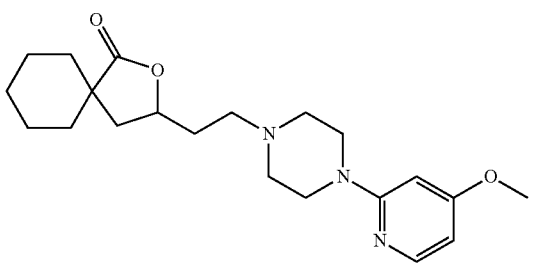 [SMILES: COc1ccnc(N2CCN(CCC3CC4(CCCCC4)C(=O)O3)CC2)c1]

Preparation of 3-(2-(4-(4-methoxypyridin-2-yl)piperazin-1-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 1-(4-methoxypyridin-2-yl)piperazine was substituted for 1-(5-chloropyridin-2-yl)piperazine. $^1$H NMR (400 MHz, MeOD) δ 7.92 (d, J=5.9 Hz, 1H), 6.37 (dd, J=5.9 Hz, J=2.1 Hz, 1H), 6.29 (d, J=2.0 Hz, 1H), 4.57 (m, 1H), 3.84 (s, 1H), 3.52 (t, J=5.1 Hz, 4H) 2.62 (m, 4H), 2.55 (m, 3H), 1.94 (m, 2H), 1.75 (m, 6H), 1.53 (m, 3H), 1.36 (m, 2H). LC/MS M+1=374.2.

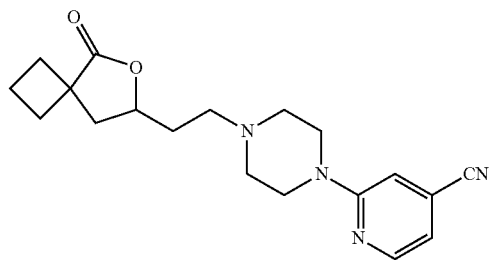 [SMILES: N#Cc1ccnc(N2CCN(CCC3CC4(CCC4)C(=O)O3)CC2)c1]

Preparation of 2-(4-(2-(5-oxo-6-oxaspiro[3.4]octan-7-yl)ethyl)piperazin-1-yl)isonicotinonitrile: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-benzo[d]imidazol-2(3H)-one was substituted for 2-(piperazin-1-yl)isonicotinonitrile and 2-(5-oxo-6-oxaspiro[3.4]octan-7-yl)ethyl 4-methylbenzenesulfonate was substituted for 2-(5-oxo-6-oxaspiro[3.4]octan-7-yl)ethyl 4-methylbenzenesulfonate. $^1$H NMR (400 MHz, MeOD) δ 8.27 (dd, J=5.0 Hz, J=1.0 Hz, 1H), 7.1 (s, 1H), 6.85 (dd, J=5.0 Hz, J=1.1 Hz, 1H), 4.49 (m, 1H), 3.63 (t, J=5.1 Hz, 4H) 2.61 (m, 4H), 2.57 (m, 4H), 2.36 (m, 1H), 2.19 (m, 1H), 2.07 (m, 4H), 1.90 (m, 2H). LC/MS M+1=341.2.

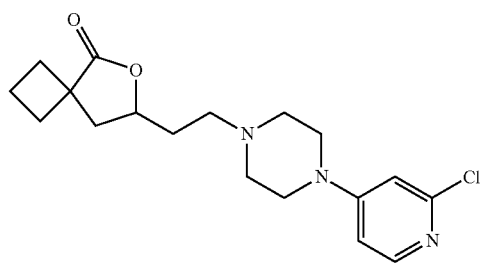 [SMILES: O=C1OC(CCN2CCN(c3ccnc(Cl)c3)CC2)CC12CCC2]

Preparation of 7-(2-(4-(2-chloropyridin-4-yl)piperazin-1-yl)ethyl)-6-oxaspiro[3.4]octan-5-one: The title compound was prepared according to the procedure for 3-{2-[4-(5-Chloro-pyridin-2-yl)-piperazin-1-yl]-ethyl}-2-oxa-spiro[4.5]decan-1-one except 5-(piperazin-1-yl)-1H-benzo[d]imidazol-2(3H)-one was substituted for 1-(2-chloropyridin-4-yl)piperazine and 2-(5-oxo-6-oxaspiro[3.4]octan-7-yl)ethyl 4-methylbenzenesulfonate was substituted for 2-(5-oxo-6-oxaspiro[3.4]octan-7-yl)ethyl 4-methylbenzenesulfonate. $^1$H NMR (400 MHz, MeOD) δ 7.93 (d, J=6.2 Hz, 1H), 6.83 (d, J=2.6 Hz, 1H), 6.82 (dd, J=6.2 Hz, J=2.4 Hz, 1H), 4.45 (m, 1H), 3.44 (t, J=5.1 Hz, 4H) 2.61 (m, 4H), 2.55 (m, 4H), 2.36 (m, 1H), 2.17 (m, 1H), 2.06 (m, 4H), 1.88 (m, 2H). LC/MS M+1=350.2.

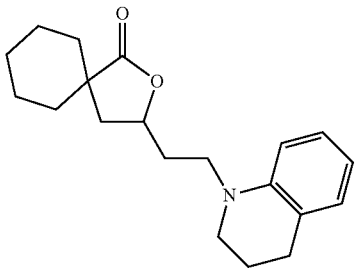 [SMILES: O=C1OC(CCN2CCCc3ccccc32)CC12CCCCC2]

Preparation of 3-(2-(3,4-dihydroquinolin-1(2H)-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 1,2,3,4-tetrahydroquinoline was substituted for 1-(5-chloropyridin-2-yl)piperazine. ¹H NMR (400 MHz, Chloroform-d) δ 7.07 (t, J=8.9 Hz 1H), 6.98 (dd, J=1.6 Hz, J=0.8 Hz, 1H), 6.59 (m, 2H), 4.49 (m, 1H), 3.48 (m, 2H), 3.31 (t, J=5.6 Hz, 2H) 2.77 (t, J=6.3 Hz, 2H), 2.41 (m, 1H), 1.97 (m, 2H), 1.85 (m, 4H), 1.66 (m, 5H), 1.37 (m, 4H). LC/MS M+1=314.2.

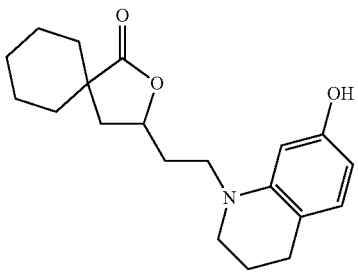 [SMILES: O=C1OC(CCN2CCCc3ccc(O)cc32)CC12CCCCC2]

Preparation of 3-(2-(7-hydroxy-3,4-dihydroquinolin-1(2H)-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 1,2,3,4-tetrahydroquinolin-7-ol was substituted for 1-(5-chloropyridin-2-yl)piperazine. ¹H NMR (400 MHz, Chloroform-d) δ 6.78 (d, J=8.0 Hz 1H), 6.13 (d, J=2.4 Hz, 1H), 6.08 (dd, J=8.0 Hz, J=2.4 Hz, 1H), 5.36 (s, 1H), 4.46 (m, 1H), 3.40 (m, 2H), 3.25 (t, J=5.1 Hz, 2H) 2.66 (t, J=6.3 Hz, 2H), 2.38 (m, 1H), 1.92 (m, 2H), 1.80 (m, 4H), 1.64 (m, 5H), 1.37 (m, 4H). LC/MS M+1=329.2.

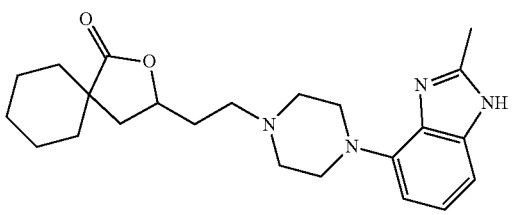 [SMILES: Cc1nc2c(N3CCN(CCC4CC5(CCCCC5)C(=O)O4)CC3)cccc2[nH]1]

Preparation of 3-(2-(4-(2-methyl-1H-benzo[d]imidazol-4-yl)piperazin-1-yl)ethyl)-2-oxaspiro[4.5]decan-1-one: The title compound was prepared according to the procedure for 3-{2-[4-(5-Chloro-pyridin-2-yl)-piperazin-1-yl]-ethyl}-2-oxa-spiro[4.5]decan-1-one except 12-methyl-7-(piperazin-1-yl)-1H-benzo[d]imidazole was substituted for 1-(5-chloropyridin-2-yl)piperazine. ¹H NMR (400 MHz, MeOD) δ 7.17 (m, 2H), 6.76 (dd, J=6.7 Hz, J=2.4 Hz, 1H), 4.60 (m, 1H), 3.73 (m, 2H) 3.49 (m, 4H) 3.19 (m, 4H), 3.07 (m, 2H), 2.60 (s, 3H), 2.11 (m, 2H), 1.79 (m, 5H), 1.54 (m, 3H), 1.38 (m, 2H). LC/MS M+1=397.2.

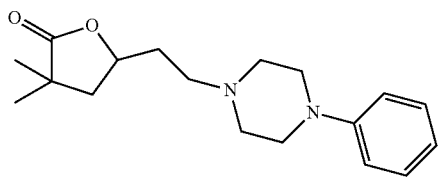 [SMILES: CC1(C)CC(CCN2CCN(c3ccccc3)CC2)OC1=O]

Preparation of dihydro-3,3-dimethyl-5-(2-(4-phenylpiperazin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 1-phenylpiperazine substituted for 1-(2-chloropyridin-4-yl)piperazine and 2-(4,4-dimethyl-5-oxotetrahydrofuran-2-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 7.32 (m, 2H), 6.99 (d, J=7.9 Hz, 1H), 6.91 (t, J=7.2 Hz, 1H), 4.58 (m, 1H), 3.26 (t, J=5.0 Hz, 4H) 2.66 (m, 4H), 2.61 (m, 2H), 2.26 (m, 1H), 1.90 (m, 3H), 1.34 (s, 3H), 1.33 (s, 3H). LC/MS M+1=303.2.

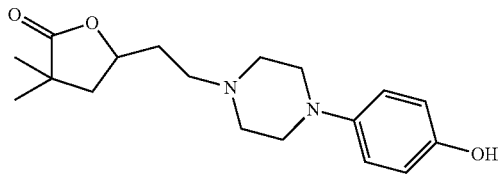 [SMILES: CC1(C)CC(CCN2CCN(c3ccc(O)cc3)CC2)OC1=O]

Preparation of dihydro-5-(2-(4-(4-hydroxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 4-(piperazin-1-yl)phenol substituted for 1-(2-chloropyridin-4-yl)piperazine and 2-(4,4-dimethyl-5-oxotetrahydrofuran-2-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 6.87 (m, 2H), 6.77 (m, 2H), 4.54 (m, 1H), 3.21 (t, J=4.9 Hz, 4H) 2.63 (m, 4H), 2.57 (m, 2H), 2.22 (m, 1H), 1.84 (m, 3H), 1.30 (s, 3H), 1.29 (s, 3H). LC/MS M+1=319.2.

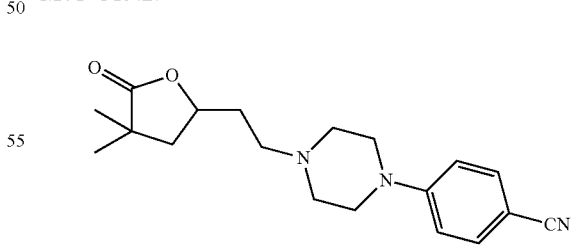

Preparation of 4-(4-(2-(tetrahydro-4,4-dimethyl-5-oxo-furan-2-yl)ethyl)piperazin-1-yl)benzonitrile: The title compound was prepared according to the procedure for 3-{2-[4-(5-Chloro-pyridin-2-yl)-piperazin-1-yl]-ethyl}-2-oxa-spiro[4.5]decan-1-one except 4-(piperazin-1-yl)benzonitrile substituted for 1-(2-chloropyridin-4-yl)piperazine and 2-(4,4-dimethyl-5-oxotetrahydrofuran-2-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 7.38 (d, J=9.0 Hz, 2H), 6.74 (d, J=9.0 Hz, 2H), 4.42 (m, 1H), 3.22 (t, J=5.0 Hz, 4H) 2.46 (m, 4H), 2.43 (m, 2H), 2.08 (m, 1H), 1.70 (m, 3H), 1.18 (s, 3H), 1.16 (s, 3H). LC/MS M+1=328.2.

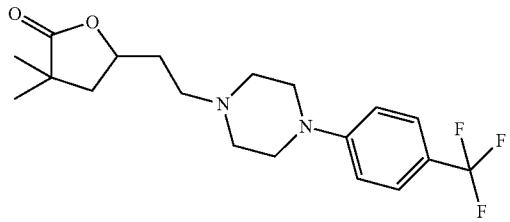 [SMILES: CC1(C)CC(CCN2CCN(c3ccc(C(F)(F)F)cc3)CC2)OC1=O]

Preparation of 5-(2-(4-(4-(trifluoromethyl)phenyl)piperazin-1-yl)ethyl)-dihydro-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 1-(4-(trifluoromethyl)phenyl)piperazine substituted for 1-(2-chloropyridin-4-yl)piperazine and 2-(4,4-dimethyl-5-oxotetrahydrofuran-2-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 7.40 (d, J=8.7 Hz, 2H), 6.84 (d, J=8.7 Hz, 2H), 4.46 (m, 1H), 3.21 (t, J=5.0 Hz, 4H) 2.53 (m, 4H), 2.47 (m, 2H), 2.11 (m, 1H), 1.78 (m, 3H), 1.21 (s, 3H), 1.20 (s, 3H). LC/MS M+1=371.2.

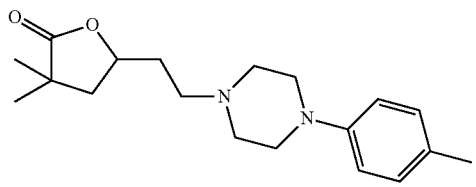 [SMILES: Cc1ccc(N2CCN(CCC3CC(C)(C)C(=O)O3)CC2)cc1]

Preparation of dihydro-3,3-dimethyl-5-(2-(4-p-tolylpiperazin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 1-(p-tolyl)piperazine substituted for 1-(2-chloropyridin-4-yl)piperazine and 2-(4,4-dimethyl-5-oxotetrahydrofuran-2-yl)ethyl 4-methylbenzenesulfonate was substituted for 2-(5-oxo-6-oxaspiro[3.4]octan-7-yl)ethyl 4-methylbenzenesulfonate. ¹H NMR (400 MHz, Chloroform-d) δ 7.09 (d, J=8.74 Hz, 2H), 6.86 (d, J=8.5 Hz, 2H), 4.54 (m, 1H), 3.17 (t, J=4.9 Hz, 4H) 2.64 (m, 4H), 2.58 (m, 2H), 2.24 (s, 3H), 1.94 (m, 1H), 1.86 (m, 3H), 1.30 (s, 3H), 1.28 (s, 3H). LC/MS M+1=317.2.

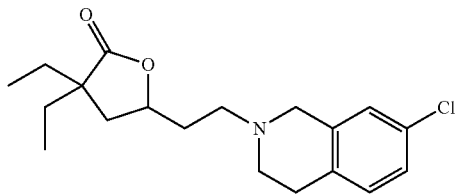 [SMILES: CCC1(CC)CC(CCN2CCc3ccc(Cl)cc3C2)OC1=O]

Preparation of 5-(2-(7-chloro-3,4-dihydroisoquinolin-2(1H)-yl)ethyl)-3,3-diethyl-dihydrofuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-(4,4-diethyl-5-oxotetrahydrofuran-2-yl)ethyl 4-methylbenzenesulfonate was substituted for 2-(1-oxo-2-oxaspiro[4.5]decan-3-yl)ethyl 4-methylbenzenesulfonate and 7-chloro-1,2,3,4-tetrahydroisoquinoline was substituted for 1-(5-chloropyridin-2-yl)piperazine. ¹H NMR (400 MHz, CDCl₃) δ 7.02 (dd, J=2.2, 8.2, 1H), 6.95 (m, 2H), 4.45 (m, 1H), 3.52 (s, 2H), 2.77 (m, 2H), 2.63 (m, 4H), 2.07 (dd, J=6.7, 13.0, 1H), 1.83 (m, 3H), 1.55 (qd, J=1.2, 7.3, 4H), 0.85 (dt, J=7.5, 15.3, 6H) LC/MS [M+H]=m/z 336.1.

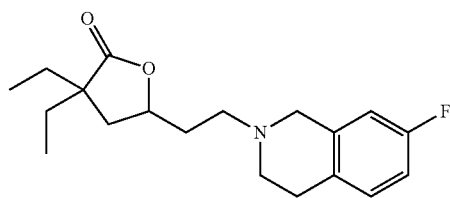 [SMILES: CCC1(CC)CC(CCN2CCc3ccc(F)cc3C2)OC1=O]

Preparation of 3,3-diethyl-5-(2-(7-fluoro-3,4-dihydroisoquinolin-2(1H)-yl)ethyl)-dihydrofuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-(4,4-diethyl-5-oxotetrahydrofuran-2-yl)ethyl 4-methylbenzenesulfonate was substituted for 2-(1-oxo-2-oxaspiro[4.5]decan-3-yl)ethyl 4-methylbenzenesulfonate and 7-fluoro-1,2,3,4-tetrahydroisoquinoline was substituted for 1-(5-chloropyridin-2-yl)piperazine. ¹H NMR (400 MHz, CDCl₃) δ 7.06 (dd, J=5.8, 8.3, 1H), 6.84 (td, J=2.7, 8.5 1H), 6.73 (dd, J=2.5, 9.5, 1H), 4.54 (m, 1H), 3.62 (s, 2H), 2.86 (m, 2H), 2.75 (m, 2H), 2.68 (m, 2H), 2.16 (dd, J=6.8, 13.0, 4H), 1.90 (m, 3H), 1.64 (qt, J=1.7, 7.6, 4H), 0.94 (dt, J=7.5, 15.8, 6H) LC/MS [M+H]=m/z 320.1.

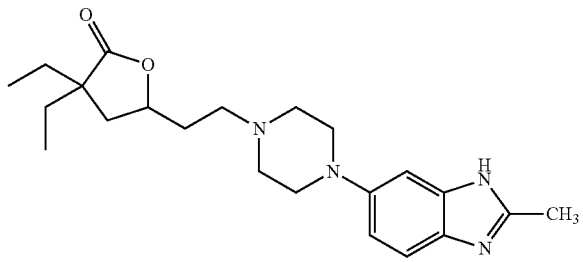 [SMILES: CCC1(CC)CC(CCN2CCN(c3ccc4nc(C)[nH]c4c3)CC2)OC1=O]

Procedure for 3,3-diethyl-dihydro-5-(2-(4-(2-methyl-1H-benzo[d]imidazol-6-yl)piperazin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-(4,4-diethyl-5-oxotetrahydrofuran-2-yl)ethyl 4-methylbenzenesulfonate was substituted for 2-(1-oxo-2-oxaspiro[4.5]decan-3-yl)ethyl 4-methylbenzenesulfonate and 2-methyl-6-(piperazin-1-yl)-1H-benzo[d]imidazole was substituted for 1-(5-chloropyridin-2-yl)piperazine. ¹H NMR (400 MHz, CDCl₃) δ 7.35 (d, J=8.8, 1H), 6.95 (s, 1H), 6.86 (dd, J=2.3, 8.7 1H), 4.42 (m, 1H), 3.10 (m, 4H), 2.61-2.42 (m, 9H), 2.07 (dd, J=6.6, 12.9, 1H), 1.80 (m, 3H), 1.56 (m, 4H), 0.86 (dt, J=7.3, 19.5, 6H) LC/MS [M+H]=m/z 385.1.

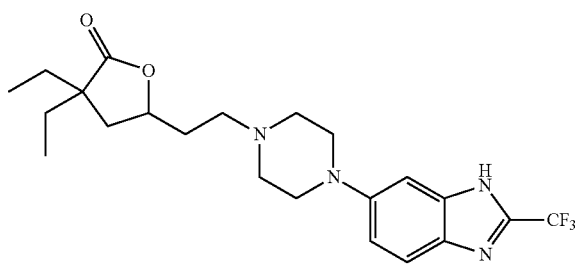 [SMILES: CCC1(CC)CC(CCN2CCN(c3ccc4nc(C(F)(F)F)[nH]c4c3)CC2)OC1=O]

Preparation of 3,3-diethyl-5-(2-(4-(2-(trifluoromethyl)-1H-benzo[d]imidazol-6-yl)piperazin-1-yl)ethyl)-dihydrofuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-(4,4-diethyl-5-oxotetrahydrofuran-2-yl)ethyl 4-methylbenzenesulfonate was substituted for 2-(1-oxo-2-oxaspiro[4.5]decan-3-yl)ethyl 4-methylbenzenesulfonate and 2-(trifluoromethyl)-6-(piperazin-1-yl)-1H-benzo[d]imidazole was substituted for 1-(5-chloropyridin-2-yl)piperazine. 1H NMR (400 MHz, CDCl₃) δ 7.59 (b, 1H), 7.02 (b, 1H), 6.85 (b, 1H), 4.43 (m, 1H), 3.11 (m, 4H), 2.61-2.39 (m, 6H), 2.08 (dd, J=6.9, 13.0, 1H), 1.79 (m, 3H), 1.56 (m, 4H), 0.85 (dt, J=7.6, 19.5, 6H) LC/MS [M+H]=m/z 439.2.

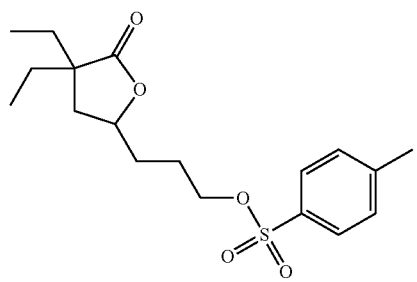 [SMILES: CCC1(CC)CC(CCCOS(=O)(=O)c2ccc(C)cc2)OC1=O]

Preparation of 3-(4,4-diethyl-tetrahydro-5-oxofuran-2-yl)propyl 4-methylbenzenesulfonate: The title compound was prepared according to the procedure for 2-(4,4-dimethyl-5-oxotetrahydrofuran-2-yl)ethyl 4-methylbenzenesulfonate.

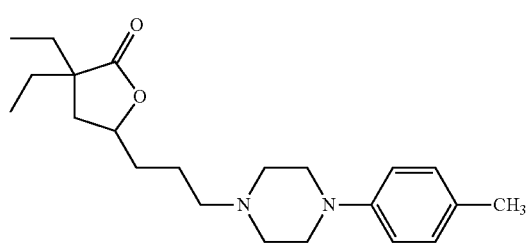 [SMILES: CCC1(CC)CC(CCCN2CCN(c3ccc(C)cc3)CC2)OC1=O]

Preparation of 3,3-diethyl-dihydro-5-(3-(4-p-tolylpiperazin-1-yl)propyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 1-p-tolylpiperazine was substituted for 1-(5-chloropyridin-2-yl)piperazine. ¹H NMR (400 MHz, CDCl₃) δ 7.14 (d, J=8.3, 1H), 6.91 (d, J=8.4, 1H), 4.40 (m, 1H), 3.86-2.95 (m, 10H), 2.31 (s, 3H), 2.16 (dd, J=6.7, 13.0, 1H), 2.00 (m, 2H), 1.80 (m, 2H), 1.63 (m, 5H), 0.93 (dt, J=7.4, 22.7, 6H) LC/MS [M+H]=m/z 359.2.

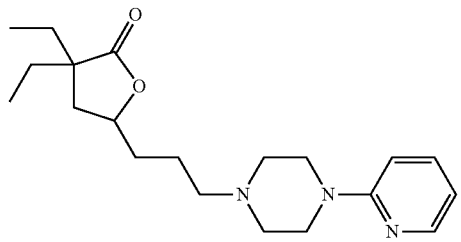 [SMILES: CCC1(CC)CC(CCCN2CCN(c3ccccn3)CC2)OC1=O]

Preparation of 3,3-diethyl-dihydro-5-(3-(4-(pyridin-2-yl)piperazin-1-yl)propyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 1-(pyridin-2-yl)piperazine was substituted for 1-(5-chloropyridin-2-yl)piperazine. 1H NMR (400 MHz, CDCl₃) δ 5.15 (d, J=4.8, 1H), 7.97 (t, J=8.3, 1H), 7.11 (d, J=8.9, 1H), 7.03 (t, J=6.3, 1H), 4.40 (m, 1H), 4.10 (b, 4H), 3.48 (b, 4H), 3.19 (b, 2H), 2.14 (dd, J=6.8, 13.3, 1H), 1.98 (m, 2H), 1.78 (dd, J=9.3, 15.0, 2H), 1.62 (m, 5H), 0.90 (dt, J=7.5, 20.9, 6H) LC/MS [M+H]=m/z 346.2.

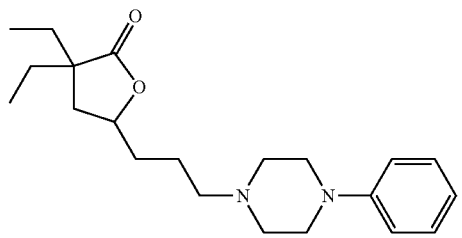 [SMILES: CCC1(CC)CC(CCCN2CCN(c3ccccc3)CC2)OC1=O]

Preparation of 3,3-diethyl-dihydro-5-(3-(4-phenylpiperazin-1-yl)propyl)furan-2(3H)-one: The title compound was prepared according to the procedure for 3-{2-[4-(5-Chloropyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 1-phenylpiperazine was substituted for 1-(5-chloropyridin-2-yl)piperazine. 1H NMR (400 MHz, CDCl₃) δ 7.32 (td, J=1.1, 7.7, 2H), 7.00 (t, J=7.4, 1H), 6.95 (d, J=8.6, 1H), 4.40 (m, 1H), 3.70 (m, 4H), 3.35 (m, 2H), 3.16 (t, J=8.1, 2H), 3.01 (b, 2H), 2.16 (dd, J=6.7, 13.4, 1H), 2.01 (m, 2H), 1.81 (m, 2H), 1.64 (m, 5H), 0.94 (dt, J=7.5, 22.4, 6H) LC/MS [M+H]=m/z 345.2.

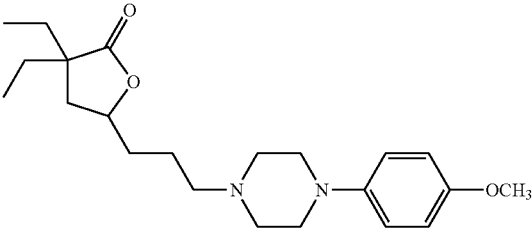 [SMILES: CCC1(CC)CC(CCCN2CCN(c3ccc(OC)cc3)CC2)OC1=O]

Preparation of 3,3-diethyl-dihydro-5-(3-(4-(4-methoxyphenyl)piperazin-1-yl)propyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 1-(4-methoxyphenyl)piperazine was substituted for 1-(5-chloropyridin-2-yl)piperazine. $^1$H NMR (400 MHz, CDCl$_3$) δ 7.03 (d, J=8.9, 2H), 6.89 (d, J=8.9, 2H), 4.40 (m, 1H), 3.90-2.96 (m, 13H), 2.15 (dd, J=6.8, 12.9, 1H), 1.99 (m, 2H), 1.80 (m, 2H), 1.64 (m, 5H), 0.92 (dt, J=7.6, 22.3, 6H) LC/MS [M+H]=m/z 375.2.

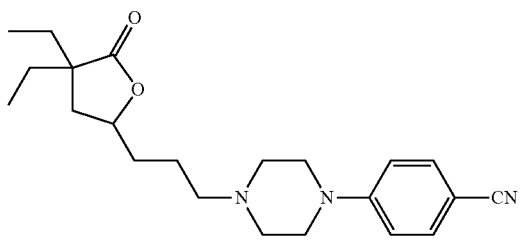

Preparation of 4-(4-(3-(4,4-diethyl-tetrahydro-5-oxofuran-2-yl)propyl)piperazin-1-yl)benzonitrile: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 4-(piperazin-1-yl)benzonitrile was substituted for 1-(5-chloropyridin-2-yl)piperazine. $^1$H NMR (400 MHz, CDCl$_3$) δ 7.49 (d, J=8.9, 2H), 6.84 (d, J=8.9, 2H), 4.32 (m, 1H), 3.98-2.61 (m, 10H), 2.07 (dd, J=6.8, 13.5, 1H), 1.93 (m, 2H), 1.73 (m, 2H), 1.55 (m, 5H), 0.84 (dt, J=7.4, 22.4, 6H) LC/MS [M+H]=m/z 370.2

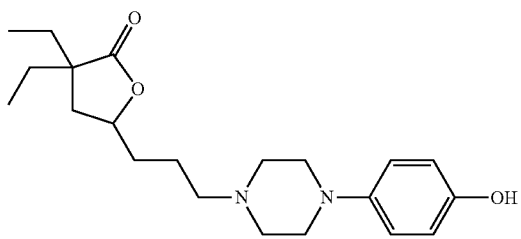

Preparation of 3,3-diethyl-dihydro-5-(3-(4-(4-hydroxyphenyl)piperazin-1-yl)propyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 4-(piperazin-1-yl)phenol was substituted for 1-(5-chloropyridin-2-yl)piperazine. $^1$H NMR (400 MHz, CDCl$_3$) δ 6.73 (dd, J=8.5, 28.7, 4H), 4.31 (m, 1H), 3.78-2.76 (m, 10H), 2.07 (dd, J=6.7, 13.2, 1H), 1.87 (m, 2H), 1.70 (dd, J=9.5, 14.1, 2H), 1.53 (m, 5H), 0.83 (dt, J=7.4, 21.3, 6H) LC/MS [M+H]=m/z 361.2.

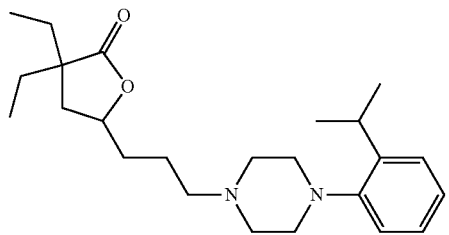 [SMILES: CCC1(CC)CC(CCCN2CCN(c3ccccc3C(C)C)CC2)OC1=O]

Preparation of 3,3-diethyl-dihydro-5-(3-(4-(2-isopropylphenyl)piperazin-1-yl)propyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 3-(4,4-diethyl-tetrahydro-5-oxofuran-2-yl)propyl 4-methylbenzenesulfonate was substituted for 2-(1-oxo-2-oxaspiro[4.5]decan-3-yl)ethyl 4-methylbenzenesulfonate and 1-(2-isopropylphenyl)piperazine was substituted for 1-(5-chloropyridin-2-yl)piperazine. $^1$H NMR (400 MHz, CDCl$_3$) δ 7.30 (m, 1H), 7.27-7.11 (m, 3H), 4.41 (m, 1H), 3.77 (t, J=10.8, 2H), 3.64-3.14 (m, 9H), 2.11 (dd, J=6.8, 13.1, 1H), 1.93 (m, 2H), 1.77 (m, 2H), 1.57 (m, 5H), 1.16 (s, 3H), 1.14 (s, 3H), 0.84 (dt, J=7.4, 21.4, 6H) LC/MS [M+H]=m/z 387.2.

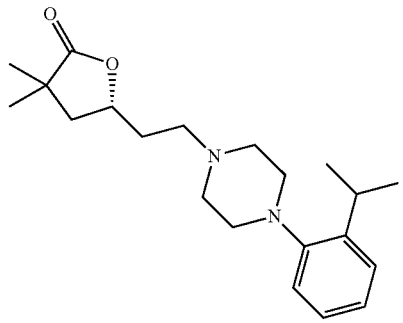 [SMILES: CC(C)c1ccccc1N1CCN(CC[C@@H]2CC(C)(C)C(=O)O2)CC1]

Preparation of (S)-dihydro-5-(2-(4-(2-isopropylphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(2-isopropylphenyl)piperazine was substituted for 1-(5-chloropyridin-2-yl)piperazine. $^1$H NMR (400 MHz, CDCl$_3$) δ 7.30 (m, 1H), 7.20 (m, 2H), 7.14 (m, 1H), 4.52 (m, 1H), 3.75 (m, 2H), 3.35 (m, 6H), 3.08 (m, 4H), 2.32 (m, 2H), 2.08 (m, 1H), 1.81 (dd, J=10.3, 13.0, 1H), 1.30 (d, J=8.4, 6H), 1.22 (d, J=8.4, 6H) LC/MS [M+H]=m/z 345.2.

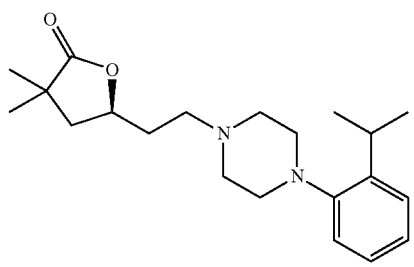 [SMILES: CC(C)c1ccccc1N1CCN(CC[C@H]2CC(C)(C)C(=O)O2)CC1]

Preparation of (R)-dihydro-5-(2-(4-(2-isopropylphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(2-isopropylphenyl)piperazine was substituted for 1-(5-chloropyridin-2-yl)piperazine. ¹H NMR (400 MHz, CDCl₃) δ 7.30 (m, 1H), 7.20 (m, 2H), 7.14 (m, 1H), 4.52 (m, 1H), 3.75 (m, 2H), 3.35 (m, 6H), 3.08 (m, 4H), 2.32 (m, 2H), 2.08 (m, 1H), 1.81 (dd, J=10.3, 13.0, 1H), 1.30 (d, J=8.4, 6H), 1.22 (d, J=8.4, 6H) LC/MS [M+H]=m/z 345.2.

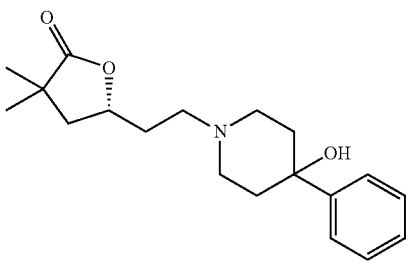 [SMILES: CC1(C)C[C@@H](CCN2CCC(O)(c3ccccc3)CC2)OC1=O]

Preparation of (S)-dihydro-5-(2-(4-hydroxy-4-phenylpiperidin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl)}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 4-phenylpiperidin-4-ol was substituted for 1-(5-chloropyridin-2-yl)piperazine. ¹H NMR (400 MHz, MeOD) δ 7.40 (dd, J=1.3, 8.5, 2H), 7.24 (t, J=7.4, 2H), 7.1 (tt, J=1.1, 7.4, 1H), 4.48 (m, 1H), 2.90 (d, J=11.3, 2H), 2.67 (m, 4H), 2.18 (dd, J=6.1, 12.6, 1H), 2.08 (td, J=4.5, 13.6, 2H), 1.89 (m, 2H), 1.72 (m, 3H), 1.16 (s, 3H), 1.15 (s, 3H), LC/MS [M+H]=m/z 302.1.

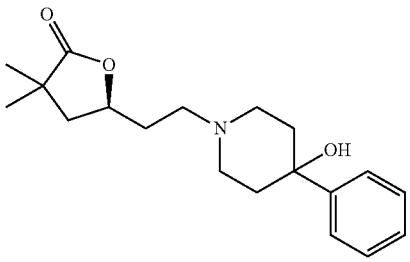 [SMILES: CC1(C)C[C@H](CCN2CCC(O)(c3ccccc3)CC2)OC1=O]

Preparation of (R)-dihydro-5-(2-(4-hydroxy-4-phenylpiperidin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl)}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 4-phenylpiperidin-4-ol was substituted for 1-(5-chloropyridin-2-yl)piperazine. ¹H NMR (400 MHz, MeOD) δ 7.40 (dd, J=1.3, 8.5, 2H), 7.24 (t, J=7.4, 2H), 7.1 (tt, J=1.1, 7.4, 1H), 4.48 (m, 1H), 2.90 (d, J=11.3, 2H), 2.67 (m, 4H), 2.18 (dd, J=6.1, 12.6, 1H), 2.08 (td, J=4.5, 13.6, 2H), 1.89 (m, 2H), 1.72 (m, 3H), 1.16 (s, 3H), 1.15 (s, 3H), LC/MS [M+H]=m/z 302.1.

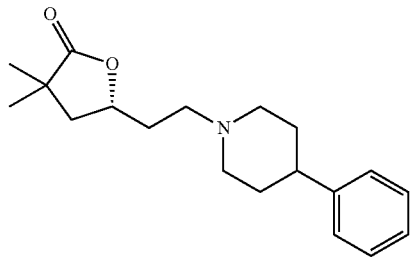 [SMILES: CC1(C)C[C@@H](CCN2CCC(c3ccccc3)CC2)OC1=O]

Preparation of (S)-dihydro-3,3-dimethyl-5-(2-(4-phenylpiperidin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 4-phenylpiperidine was substituted for 1-(5-chloropyridin-2-yl)piperazine. ¹H NMR (400 MHz, MeOD) δ 7.32-7.13 (m, 5H), 4.58 (m, 1H), 3.11 (d, J=11.8, 2H), 2.59 (m, 3H), 2.28 (dd, J=6.2, 12.8, 1H), 2.18 (tt, J=3.5, 11.7, 2H), 1.99-1.72 (m, 7H), 1.27 (s, 3H), 1.1.26 (s, 3H), LC/MS [M+H]=m/z 302.1.

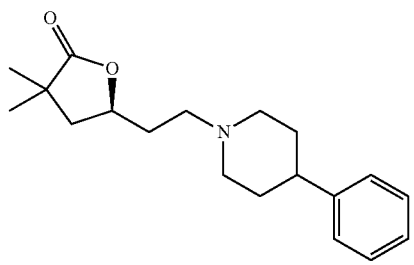 [SMILES: CC1(C)C[C@H](CCN2CCC(c3ccccc3)CC2)OC1=O]

Preparation of (R)-dihydro-3,3-dimethyl-5-(2-(4-phenylpiperidin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 4-phenylpiperidine was substituted for 1-(5-chloropyridin-2-yl)piperazine. ¹H NMR (400 MHz, MeOD) δ 7.32-7.13 (m, 5H), 4.58 (m, 1H), 3.11 (d, J=11.8, 2H), 2.59 (m, 3H), 2.28 (dd, J=6.2, 12.8, 1H), 2.18 (tt, J=3.5, 11.7, 2H), 1.99-1.72 (m, 7H), 1.27 (s, 3H), 1.1.26 (s, 3H), LC/MS [M+H]=m/z 302.1.

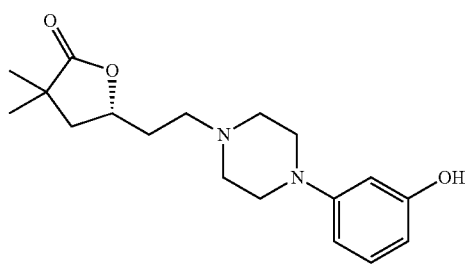 [SMILES: CC1(C)C[C@@H](CCN2CCN(c3cccc(O)c3)CC2)OC1=O]

Preparation of (S)-dihydro-5-(2-(4-(3-hydroxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 3-(piperazin-1-yl)phenol was substituted for 1-(5-chloropyridin-2-yl)piperazine. 1H NMR (400 MHz, CDCl₃) δ 7.16 (t, J=7.9, 1H), 6.50 (m, 3H), 4.50 (m, 1H), 4.01-2.86 (m, 10H), 2.26 (m, 2H), 2.06 (m, 1H), 1.80 (dd, J=10.0, 13.1, 1H), 1.30 (s, 3H), 1.28 (s, 3H) LC/MS [M+H]=m/z 319.1.

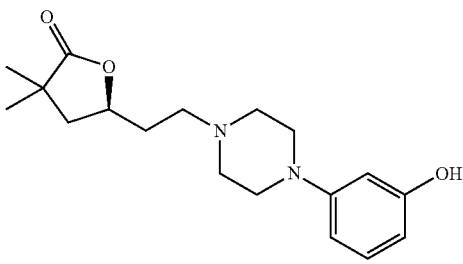 [SMILES: CC1(C)C[C@H](CCN2CCN(c3cccc(O)c3)CC2)OC1=O]

Preparation of (R)-dihydro-5-(2-(4-(3-hydroxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 3-(piperazin-1-yl)phenol was substituted for 1-(5-chloropyridin-2-yl)piperazine. ¹H NMR (400 MHz, CDCl₃) δ 7.16 (t, J=7.9, 1H), 6.50 (m, 3H), 4.50 (m, 1H), 4.01-2.86 (m, 10H), 2.26 (m, 2H), 2.06 (m, 1H), 1.80 (dd, J=10.0, 13.1, 1H), 1.30 (s, 3H), 1.28 (s, 3H) LC/MS [M+H]=m/z 319.1.

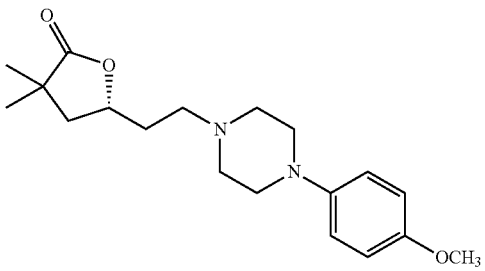 [SMILES: COc1ccc(N2CCN(CC[C@@H]3CC(C)(C)C(=O)O3)CC2)cc1]

Preparation of (S)-dihydro-5-(2-(4-(4-methoxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(4-methoxyphenyl)piperazine was substituted for 1-(5-chloropyridin-2-yl)piperazine. ¹H NMR (400 MHz, CDCl₃) δ 7.04 (d, J=8.8, 2H), 6.90 (d, J=8.8, 2H), 4.50 (m, 1H), 3.89-2.84 (m, 13H), 2.27 (m, 2H), 2.08 (m, 1H), 1.81 (dd, J=10.0, 13.0, 1H), 1.30 (s, 3H), 1.28 (s, 3H) LC/MS [M+H]=m/z 333.1.

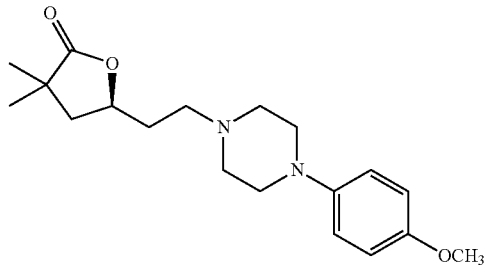 [SMILES: COc1ccc(N2CCN(CC[C@H]3CC(C)(C)C(=O)O3)CC2)cc1]

Preparation of (R)-dihydro-5-(2-(4-(4-methoxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(4-methoxyphenyl)piperazine was substituted for 1-(5-chloropyridin-2-yl)piperazine. ¹H NMR (400 MHz, CDCl₃) δ 7.04 (d, J=8.8, 2H), 6.90 (d, J=8.8, 2H), 4.50 (m, 1H), 3.89-2.84 (m, 13H), 2.27 (m, 2H), 2.08 (m, 1H), 1.81 (dd, J=10.0, 13.0, 1H), 1.30 (s, 3H), 1.28 (s, 3H) LC/MS [M+H]=m/z 333.1.

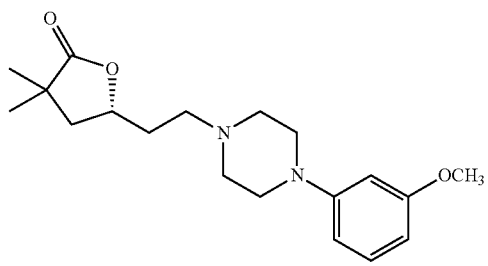 [SMILES: COc1cccc(N2CCN(CC[C@@H]3CC(C)(C)C(=O)O3)CC2)c1]

Preparation of (S)-dihydro-5-(2-(4-(3-methoxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-dimethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(3-methoxyphenyl)piperazine was substituted for 1-(5-chloropyridin-2-yl)piperazine. 1H NMR (400 MHz, CDCl₃) δ 7.22 (J=8.2, 1H), 6.54 (m, 2H), 6.47 (t, J=2.3, 1H), 4.49 (m, 1H), 3.94-2.80 (m, 13H), 2.26 (m, 2H), 2.07 (m, 1H), 1.79 (dd, J=10.0, 13.3, 1H), 1.28 (s, 3H), 1.26 (s, 3H) LC/MS [M+H]=m/z 333.1.

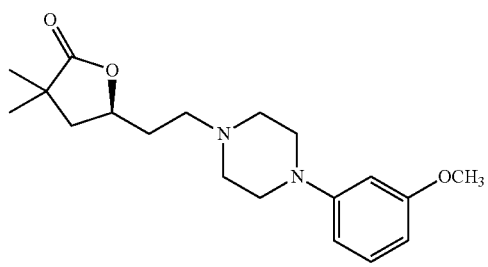 [SMILES: COc1cccc(N2CCN(CC[C@H]3CC(C)(C)C(=O)O3)CC2)c1]

Preparation of (R)-dihydro-5-(2-(4-(3-methoxyphenyl)piperazin-1-yl)ethyl)-3,3-dimethylfuran-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-dimethyl-5-oxofuran-2-yl)ethyl 4-methylbenzenesulfonate was substituted for 2-(1-oxo-2-oxaspiro[4.5]decan-3-yl) ethyl 4-methylbenzenesulfonate and 1-(3-methoxyphenyl)piperazine was substituted for 1-(5-chloropyridin-2-yl)piperazine. $^1$H NMR (400 MHz, CDCl$_3$) δ 7.22 (J=8.2, 1H), 6.54 (m, 2H), 6.47 (t, J=2.3, 1H), 4.49 (m, 1H), 3.94-2.80 (m, 13H), 2.26 (m, 2H), 2.07 (m, 1H), 1.79 (dd, J=10.0, 13.3, 1H), 1.28 (s, 3H), 1.26 (s, 3H) LC/MS [M+H]=m/z 333.1.

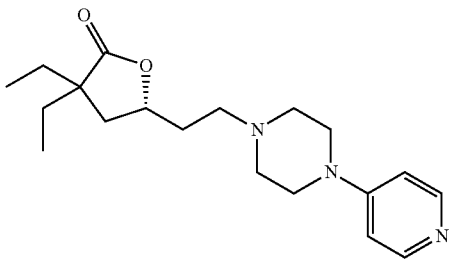 [SMILES: CCC1(CC)C[C@@H](CCN2CCN(c3ccncc3)CC2)OC1=O]

Preparation of (S)-3,3-diethyl-dihydro-5-(2-(4-(pyridin-4-yl)piperazin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((S)-tetrahydro-4,4-diethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(pyridin-4-yl)piperazine was substituted for 1-(5-chloropyridin-2-yl)piperazine. $^1$H NMR (400 MHz, CDCl$_3$) δ 8.25 (b, 2H), 6.67 (d, J=5.2, 2H), 4.49 (m, 1H), 3.35 (t, J=5.2, 4H), 2.55 (m, 6H), 2.15 (dd, J=6.7, 12.8 1H), 1.86 (m, 3H), 1.63 (m, 4H), 0.93 (dt J=7.6, 19.2, 6H), LC/MS [M+H]=m/z 332.2.

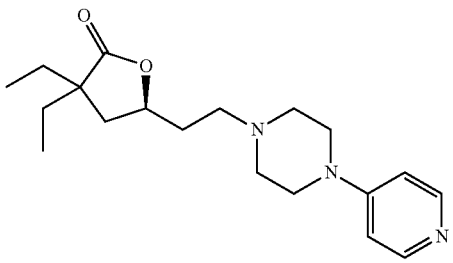

Preparation of (R)-3,3-diethyl-dihydro-5-(2-(4-(pyridin-4-yl)piperazin-1-yl)ethyl)furan-2(3H)-one: The title compound was prepared according to the procedure for 3-{2-[4-(5-Chloro-pyridin-2-yl)-piperazin-1-yl]-ethyl}-2-oxa-spiro[4.5]decan-1-one except 2-((R)-tetrahydro-4,4-diethyl-5-oxofuran-2-yl)ethyl 4-methylbenzenesulfonate was substituted for 2-(1-oxo-2-oxaspiro[4.5]decan-3-yl)ethyl 4-methylbenzenesulfonate and 1-(pyridin-4-yl)piperazine was substituted for 1-(5-chloropyridin-2-yl)piperazine. $^1$H NMR (400 MHz, CDCl$_3$) δ 8.25 (b, 2H), 6.67 (d, J=5.2, 2H), 4.49 (m, 1H), 3.35 (t, J=5.2, 4H), 2.55 (m, 6H), 2.15 (dd, J=6.7, 12.8 1H), 1.86 (m, 3H), 1.63 (m, 4H), 0.93 (dt J=7.6, 19.2, 6H), LC/MS [M+H]=m/z 332.2.

Formulations

The present invention also relates to compositions or formulations which comprise the 5-hydroxytryptamine receptor 7 activity modulators according to the present invention. In general, the compositions of the present invention comprise an effective amount of one or more compounds of the disclosure and salts thereof according to the present invention which are effective for providing modulation of 5-hydroxytryptamine receptor 7 activity; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known 5-hydroxytryptamine receptor 7 activity modulators. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.]

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention; and one or more excipients.

Procedures

The following procedures can be utilized in evaluating and selecting compounds as 5-hydroxytryptamine receptor 7 activity modulators.

Radiolabel Binding Studies for Serotonin 5HT7 receptors, method 1:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5× assay concentration) of the compound of the disclosure and chlorpromazine are prepared in the Assay Buffer by serial dilution to yield final corresponding assay concentrations ranging from 10 pM to 10 µM.

A stock concentration of 5 nM [$^3$H]LSD (lysergic acid diethyl amide) is prepared in 50 mM Tris-HCl, 10 mM $MgCl_2$, 1 mM EDTA, pH 7.4 (Assay Buffer). Aliquots (50 µl) of radioligand are dispensed into the wells of a 96-well plate containing 100 µl of Assay Buffer. Duplicate 50-µl aliquots of the compound of the disclosure test and chlorpromazine positive control reference compound serial dilutions are added.

Membrane fractions of cells expressing recombinant $5HT_7$ receptors (50 µL) are dispensed into each well. The membranes are prepared from stably transfected cell lines expressing $5HT_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-µl reactions are incubated at room temperature for 1.5 hours, then harvested by rapid filtration onto 0.3% polyethyleneimine-treated, 96-well filter mats using a 96-well Filtermate harvester. Four rapid 500-µl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+[(\text{top}-\text{bottom})/(1+10^{x-\log IC_{50}})]$$

where bottom equals the residual radioligand binding measured in the presence of 10 μM reference compound (i.e., non-specific binding) and top equals the total radioligand binding observed in the absence of competitor. The log IC$_{50}$ (i.e., the log of the ligand concentration that reduces radioligand binding by 50%) is thus estimated from the data and used to obtain the Ki by applying the Cheng-Prusoff approximation:

$Ki=IC_{50}/(1+[\text{ligand}]/KD)$ where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Serotonin 5HT$_7$ receptors to determine the percent inhibition of [$^3$H]LSD binding.

Radiolabel Binding Studies for Serotonin 5-HT7 receptors, method 2:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5× assay concentration) of the compound of the disclosure and chlorpromazine are prepared in the Assay Buffer by serial dilution to yield final corresponding assay concentrations ranging from 10 pM to 10 μM.

A stock concentration of 5 nM [$^3$H]-5-Hydroxytryptamine ([$^3$H]-5HT) is prepared in 50 mM Tris-HCl, 10 mM MgCl$_2$, 1 mM EDTA, pH 7.4 (Assay Buffer). Aliquots (50 μl) of radioligand are dispensed into the wells of a 96-well plate containing 100 μl of Assay Buffer. Duplicate 50-μl aliquots of the compound of the disclosure test and chlorpromazine positive control reference compound serial dilutions are added.

Membrane fractions of cells expressing recombinant 5HT$_7$ receptors (50 μL) are dispensed into each well. The membranes are prepared from stably transfected cell lines expressing 5HT$_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$y=\text{bottom}+[(\text{top}-\text{bottom})/(1+10^{x-\log IC_{50}})]$ where bottom equals the residual radioligand binding measured in the presence of 10 μM reference compound (i.e., non-specific binding) and top equals the total radioligand binding observed in the absence of competitor. The log IC$_{50}$ (i.e., the log of the ligand concentration that reduces radioligand binding by 50%) is thus estimated from the data and used to obtain the Ki by applying the Cheng-Prusoff approximation:

$Ki=IC_{50}/(1+[\text{ligand}]/KD)$ where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Serotonin 5HT$_7$ receptors to determine the percent inhibition of [$^3$H]-5HT binding.

Results for representative compounds according to the present invention are listed in Table 2.

TABLE 2

Radiolabel Binding Studies for Serotonin 5HT$_7$ receptors results for exemplary compounds of the disclosure

| Entry | Structure | 5-HT7 % inhib @ 10 uM | 5-HT7 IC$_{50}$ (nm) |
|---|---|---|---|
| 230010 | 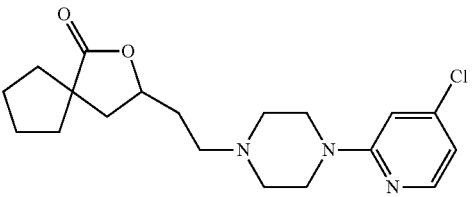 [SMILES: O=C1OC(CCN2CCN(c3cc(Cl)ccn3)CC2)CC12CCCC2] | 33.5 | N.D. |
| 230012 | 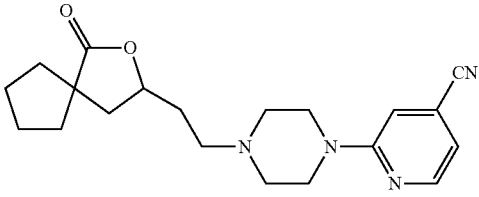 [SMILES: N#Cc1ccnc(N2CCN(CCC3CC4(CCCC4)C(=O)O3)CC2)c1] | 76.6 | 436 |

TABLE 2-continued

Radiolabel Binding Studies for Serotonin 5HT$_7$ receptors results for exemplary compounds of the disclosure

| Entry | Structure | 5-HT7 % inhib @ 10 uM | 5-HT7 IC$_{50}$ (nm) |
|---|---|---|---|
| 230009 | 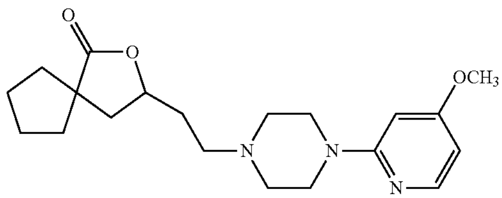 [SMILES: COc1ccnc(N2CCN(CCC3CC4(CCCC4)C(=O)O3)CC2)c1] | 90 | 124 |
| 230011 | 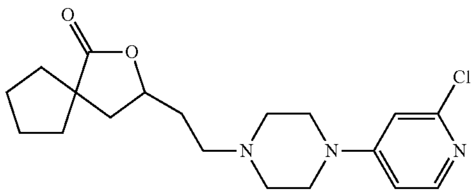 [SMILES: O=C1OC(CCN2CCN(c3ccnc(Cl)c3)CC2)CC12CCCC2] | 40.3 | N.D. |
| 230016 | 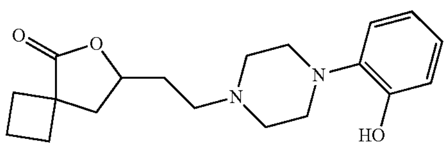 [SMILES: O=C1OC(CCN2CCN(c3ccccc3O)CC2)CC12CCC2] | 84.7 | 299 |
| 230015 | 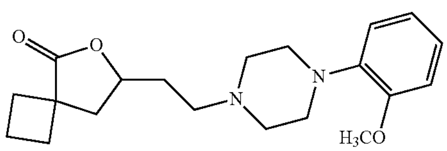 [SMILES: COc1ccccc1N1CCN(CCC2CC3(CCC3)C(=O)O2)CC1] | 83.4 | 319 |
| 230014 | 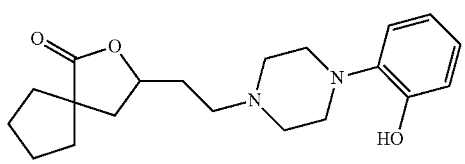 [SMILES: O=C1OC(CCN2CCN(c3ccccc3O)CC2)CC12CCCC2] | 91.5 | 78 |
| 230013 | 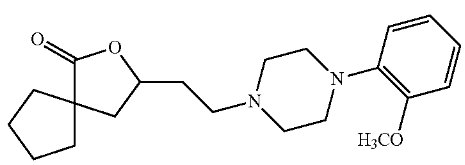 [SMILES: COc1ccccc1N1CCN(CCC2CC3(CCCC3)C(=O)O2)CC1] | 90.9 | 146 |
| 230008 | 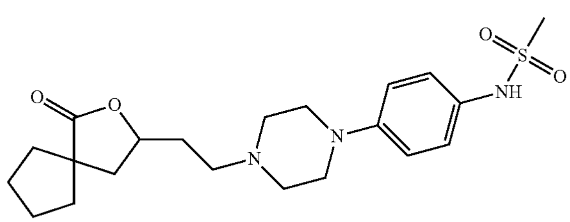 [SMILES: CS(=O)(=O)Nc1ccc(N2CCN(CCC3CC4(CCCC4)C(=O)O3)CC2)cc1] | 33.2 | N.D. |
| 160145 | 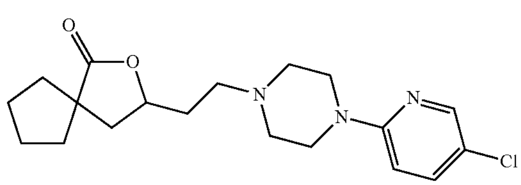 [SMILES: O=C1OC(CCN2CCN(c3ccc(Cl)cn3)CC2)CC12CCCC2] | 96.7 | 33 |

TABLE 2-continued

Radiolabel Binding Studies for Serotonin 5HT$_7$ receptors results for exemplary compounds of the disclosure

| Entry | Structure | 5-HT7 % inhib @ 10 uM | 5-HT7 IC$_{50}$ (nm) |
|---|---|---|---|
| 230039 | *(structure)* | 42.6 | 10000 |
| 230046 | *(structure)* | 53.5 | 10000 |
| 230040 | *(structure)* | 89.1 | 417 |
| 230047 | *(structure)* | 93 | 151 |
| 230057 | *(structure)* | 98.5 | 55 |
| 230058 | *(structure)* | 78.6 | 965 |

TABLE 2-continued
Radiolabel Binding Studies for Serotonin 5HT$_7$ receptors results for exemplary compounds of the disclosure
| Entry | Structure | 5-HT7 % inhib @ 10 uM | 5-HT7 IC$_{50}$ (nm) |
|---|---|---|---|
| 230059 | 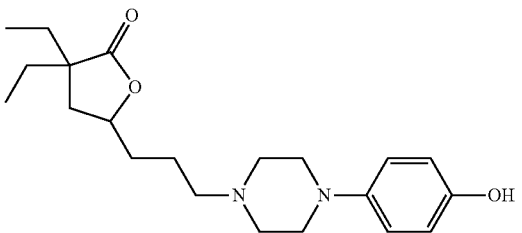 [SMILES: CCC1(CC)CC(CCCN2CCN(c3ccc(C#N)cc3)CC2)OC1=O] | 88.8 | 353 |
| 230060 | 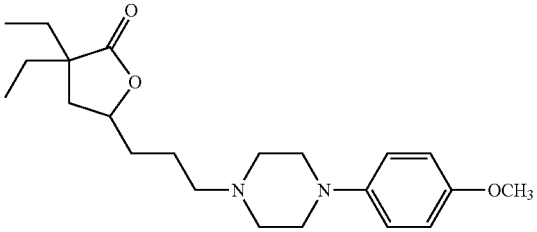 [SMILES: CCC1(CC)CC(CCCN2CCN(c3ccc(OC)cc3)CC2)OC1=O] | 43.6 | 10000 |
| 230061 | 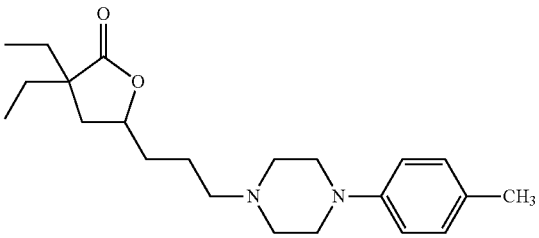 [SMILES: CCC1(CC)CC(CCCN2CCN(c3ccc(C)cc3)CC2)OC1=O] | 94.9 | 168 |
| 230062 | 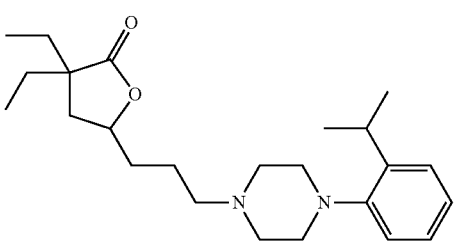 [SMILES: CCC1(CC)CC(CCCN2CCN(c3ccccc3C(C)C)CC2)OC1=O] | 98.6 | 12 |
| 230063 | 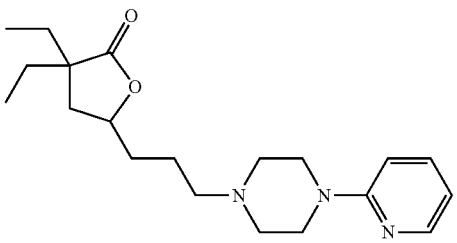 [SMILES: CCC1(CC)CC(CCCN2CCN(c3ccccn3)CC2)OC1=O] | 98.9 | 93 |
| 230068 | 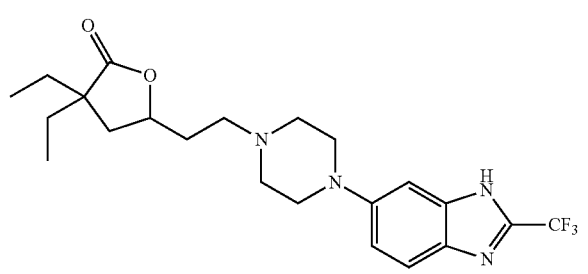 [SMILES: CCC1(CC)CC(CCN2CCN(c3ccc4nc(C(F)(F)F)[nH]c4c3)CC2)OC1=O] | 44 | 10000 |

TABLE 2-continued
Radiolabel Binding Studies for Serotonin 5HT₇ receptors results for exemplary compounds of the disclosure
| Entry | Structure | 5-HT7 % inhib @ 10 uM | 5-HT7 IC$_{50}$ (nm) |
|---|---|---|---|
| 230069 | 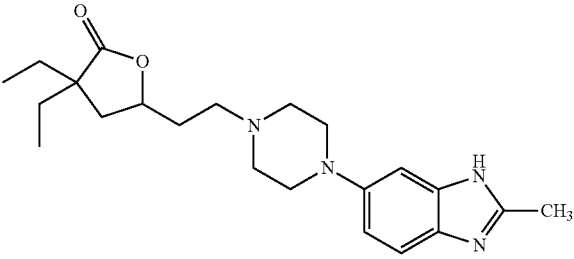 [SMILES: CCC1(CC)CC(CCN2CCN(c3ccc4nc(C)[nH]c4c3)CC2)OC1=O] | 15..9 | 10000 |
| 230070 | 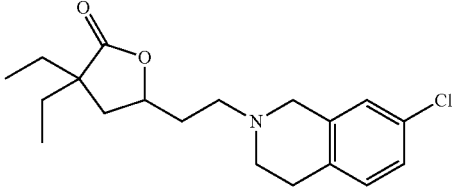 [SMILES: CCC1(CC)CC(CCN2CCc3ccc(Cl)cc3C2)OC1=O] | 100 | 7.5 |
| 230071 | 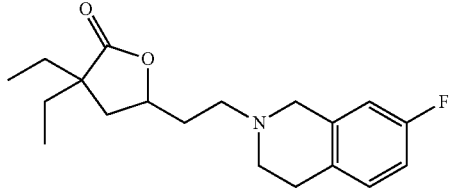 [SMILES: CCC1(CC)CC(CCN2CCc3ccc(F)cc3C2)OC1=O] | 99.3 | 9.9 |
| 230083 | 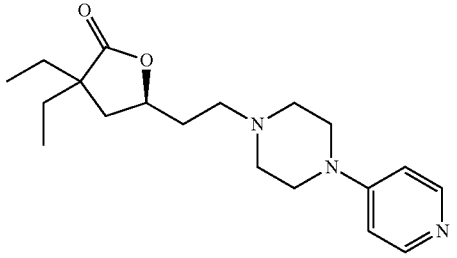 [SMILES: CCC1(CC)C[C@H](CCN2CCN(c3ccncc3)CC2)OC1=O] | 51 | 5818 |
| 160146 | 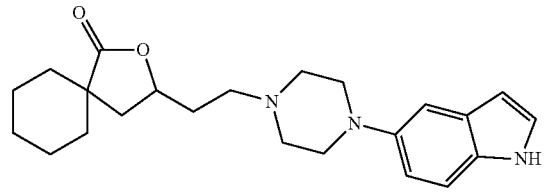 [SMILES: O=C1OC(CCN2CCN(c3ccc4[nH]ccc4c3)CC2)CC12CCCCC2] | 97.9 | 65.3 |
| 160147 | 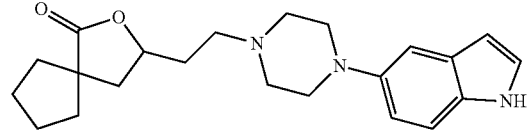 [SMILES: O=C1OC(CCN2CCN(c3ccc4[nH]ccc4c3)CC2)CC12CCCC2] | 99.6 | 56 |
| 160148 | 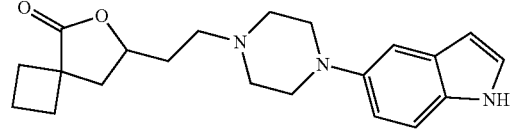 [SMILES: O=C1OC(CCN2CCN(c3ccc4[nH]ccc4c3)CC2)CC12CCC2] | 96.5 | 88 |

TABLE 2-continued

Radiolabel Binding Studies for Serotonin 5HT$_7$ receptors results for exemplary compounds of the disclosure

| Entry | Structure | 5-HT7 % inhib @ 10 uM | 5-HT7 IC$_{50}$ (nm) |
|---|---|---|---|
| 160149 | 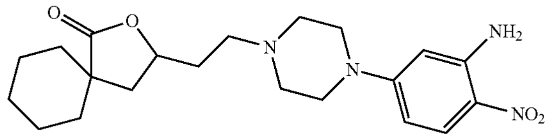 [SMILES: Nc1cc(N2CCN(CCC3CC4(CCCCC4)C(=O)O3)CC2)ccc1[N+](=O)[O-]] | 84.7 | 500 |
| 160150 | 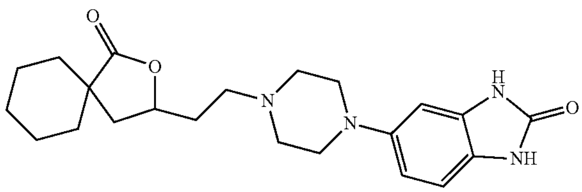 [SMILES: O=C1OC(CCN2CCN(c3ccc4[nH]c(=O)[nH]c4c3)CC2)CC12CCCCC2] | 76.9 | 1232 |
| 160151 | 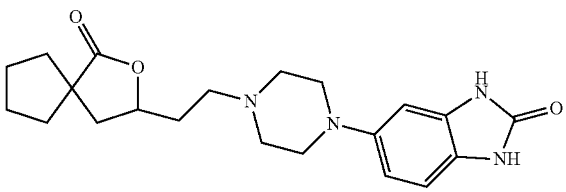 [SMILES: O=C1OC(CCN2CCN(c3ccc4[nH]c(=O)[nH]c4c3)CC2)CC12CCCC2] | 35.9 | N.D. |
| 160152 | 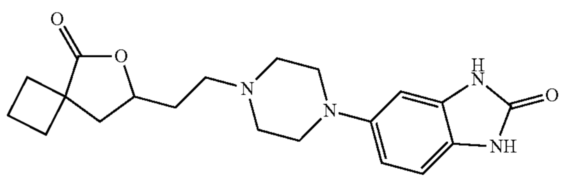 [SMILES: O=C1OC(CCN2CCN(c3ccc4[nH]c(=O)[nH]c4c3)CC2)CC12CCC2] | 59.5 | 2250 |
| 160153 | 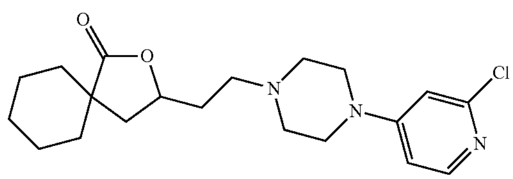 [SMILES: O=C1OC(CCN2CCN(c3ccnc(Cl)c3)CC2)CC12CCCCC2] | 58.2 | 4355 |

N.D. = not determined

Functional Serotonin 5HT$_7$ assay, method 1:

Cell lines stably expressing human 5HT$_7$ receptors are seeded in 96-well, poly-L-lysine-coated plates 48 hours prior to the assay (40,000 cells per well) in Dulbecco's Modified Eagle Medium (DMEM) containing 5% dialyzed serum. Twenty hours prior to the assay, the medium is changed to serum-free DMEM. On the day of the assay, the DMEM is washed and replaced with 30 µl of assay buffer (1× Krebs-Ringer bicarbonate glucose buffer, 0.75 mM IBMX, pH 7.4). A 10-min pre-incubation is performed in a 37-degree centigrade, humidified incubator. Then, the cells are stimulated by addition of 30 µl of 2× dilutions of compounds of the disclosure or chlorpromazine (final concentrations ranging from 0.1 nM to 10 µM, each concentration assayed in triplicate). A positive control (100 µM forskolin) is also included. Accumulation of cAMP is allowed to continue for 15 min, after which the buffer is removed and the cells are lysed with Cell Lysis Buffer (CatchPoint cAMP Assay Kit, Molecular Devices). Next, the lysates are transferred to 96-well, glass-bottom plates coated with goat anti-rabbit IgG and adsorbed with rabbit anti-cAMP (Molecular Devices). Following a 5 minute incubation, horseradish peroxidase-cAMP conjugate is added (Molecular Devices) and a 2-hour incubation is performed at room temperature. Then, after three washes with Wash Buffer (Molecular Devices), Stoplight Red substrate (Molecular Devices), reconstituted in Substrate Buffer (Molecular Devices) containing freshly-added 1 mM H$_2$O$_2$, is added and, after a 15-min incubation at room temperature, fluorescence is measured (excitation 510-545 nm, emission 565-625 nm). For each assay, a cAMP calibration curve is generated and controls without lysate and without antibody are included.

For agonist tests, raw data (maximum fluorescence, fluorescence units) for each concentration of the compounds of the disclosure or chlorpromazine are normalized to the basal (vehicle-stimulated) fluorescence (reported as fold increase over basal) and plotted as a function of the logarithm of the molar concentration of the drug (i.e., test or reference compound). Non-linear regression of the normalized data is performed in Prism 4.0 (GraphPad Software) using the built-in three parameter logistic model (i.e., sigmoidal concentration-response) describing agonist-stimulated activation of one receptor population:

$$y = \text{bottom} + [(\text{top} - \text{bottom})/(1 + 10^{x - \log EC50})]$$

where bottom equals the best-fit basal fluorescence and top equals the best-fit maximal fluorescence stimulated by the compound of the disclosure or chlorpromazine. The log $EC_{50}$ (i.e., the log of the drug concentration that increases fluorescence by 50% of the maximum fluorescence observed for the compound of the disclosure or chlorpromazine is thus estimated from the data, and the $EC_{50}$ (agonist potency) is obtained. To obtain an estimate of the relative efficacy of the test compound (Rel. Emax), its best-fit top is compared to and expressed as a ratio of that for the chlorpromazine (Rel. Emax of the reference agonist is 1.00).

To ascertain whether compounds of the disclosure are antagonists, a double-addition paradigm is employed. First, 30 µl of a compound of the disclosure (20 µM) is added (10 µM final concentration) and a 15 minute incubation is performed. Then, 30 µl of chlorpromazine (3×; $EC_{90}$) is added (final concentration of agonist is $EC_{30}$) and cAMP accumulation is allowed to proceed for 15 minutes. The samples are then processed for cAMP measurements as detailed above. Measurements of chlorpromazine-induced cAMP accumulation are compared to the signals elicited by the chlorpromazine following addition of vehicle instead of test compound and expressed as a ratio. 'Hits' (compounds that antagonize chlorpromazine-stimulated increases in baseline-normalized fluorescence by at least 50%) are then characterized by a modified Schild analysis.

For modified Schild analysis, a family of chlorpromazine concentration-response isotherms is generated in the absence and presence of graded concentrations of test compound (added 15 min prior to reference agonist). Theoretically, compounds that are competitive antagonists cause a dextral shift of agonist concentration-response isotherms without reducing the maximum response to agonist (i.e., surmountable antagonism). However, on occasion, factors such as non-competitive antagonism, hemiequilibria, and/or receptor reserve cause apparent insurmountable antagonism. To account for such deviations, we apply the modified Lew-Angus method to ascertain antagonist potency (Christopoulos et al., 1999). Briefly, equieffective concentrations of agonist (concentrations of agonist that elicit a response equal to the $EC_{25\%}$ of the agonist control curve) are plotted as a function of the compound of the disclosure concentration present in the wells in which they were measured. Non-linear regression of the baseline-normalized data is performed in Prism 4.0 using the following equation:

$$pEC_{25\%} = -\log([B]+10-pK) - \log c$$

where EC25% equals the concentration of agonist that elicits a response equal to 25% of the maximum agonist control curve response and [B] equals the antagonist concentration; K, c, and s are fit parameters. The parameter s is equal to the Schild slope factor. If s is not significantly different from unity, pK equals pKB; otherwise, pA2 is calculated (pA2=pK/s). The parameter c equals the ratio $EC_{25\%}/[B]$.

Functional Efficacy Assay for 5-HT7 Receptors Method 2:

Functional efficacy of the compounds of the disclosure on 5-HT7 serotonin receptors were measured in a cell based cAMP enzyme fragment complementation assay using the HitHunter cAMP assay (DiscoveRx). Cells stably expressing human 5HT7 receptors were plated in 96-well plates at 4000 cells/well, 16-20 hours prior to assay in growth media (Ultraculture medium, 2 mM GlutaMax and G418 1 mg/mL. Serial dilutions of the agonist, 5-Carboxamidotryptamine (5-CT), were prepared in a final concentration range of 10 µM to 10 nM. Compounds of the disclosure were prepared in 3-fold serial dilutions to obtain a final concentration range of 10 µM to 0.1 nM. Compounds of the disclosure are tested for agonist activity in the absence of 5-CT and antagonist activity in the presence of 5-CT. For the cAMP assay, the protocol was followed according to the instructions provided by the supplier. Briefly, cells were incubated with a compound of the disclosure for 30 minutes at 37° C. prior to addition of $EC_{70}$ concentration of 5-CT. After an additional 30 minutes, cAMP antibody/cell lysis solution was added (20 µL/well) and incubated for 60 minutes at room temperature. cAMP XS+EA reagent is added (20 µL/well) and incubated for 2 hours at room temperature. Luminescence was read on the Envision Multilabel plate reader.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A compound selected from the group consisting of:
(R)-3-{2-[4-(5-Chloro-pyridin-2-yl)-piperazin-1-yl]-ethyl}-2-oxa-spiro[4.5]decan-1-one;
(S)-3-{2-[4-(5-Chloro-pyridin-2-yl)-piperazin-1-yl]-ethyl}-2-oxa-spiro[4.5]decan-1-one;
(R)-3-{2-[4-(1H-Indol-5-yl)-piperazin-1-yl]-ethyl}-2-oxa-spiro[4.5]decan-1-one;
(S)-3-{2-[4-(1H-Indol-5-yl)-piperazin-1-yl]-ethyl}-2-oxa-spiro[4.5]decan-1-one;
(R)-3-{2-[4-(1H-Indol-5-yl)-piperazin-1-yl]-ethyl}-2-oxa-spiro[4.4]nonan-1-one;
(S)-3-{2-[4-(1H-Indol-5-yl)-piperazin-1-yl]-ethyl}-2-oxa-spiro[4.4]nonan-1-one;
(R)-7-{2-[4-(1H-Indol-5-yl)-piperazin-1-yl]-ethyl}-6-oxa-spiro[3.4]octan-5-one;
(S)-7-{2-[4-(1H-Indol-5-yl)-piperazin-1-yl]-ethyl}-6-oxa-spiro[3.4]octan-5-one;
(R)-3-(2-(4-(-3-amino-4-nitrophenyl)piperazin-1-yl)ethyl)-2-oxaspiro[4.5]decan-1-one;
(S)-3-(2-(4-(-3-amino-4-nitrophenyl)piperazin-1-yl)ethyl)-2-oxaspiro[4.5]decan-1-one;
(R)-5-(4-(2-(1-oxo-2-oxaspiro[4.5]decan-3-yl)ethyl)piperazin-1-yl)-1H-benzo[d]imidazol-2(3H)-one;
(S)-5-(4-(2-(1-oxo-2-oxaspiro[4.5]decan-3-yl)ethyl)piperazin-1-yl)-1H-benzo[d]imidazol-2(3H)-one;
(R)-5-(4-(2-(1-oxo-2-oxaspiro[4.4]nonan-3-yl)piperazin-1-yl)-1H-benzo[d]imidazol-2(3H)-one;
(S)-5-(4-(2-(1-oxo-2-oxaspiro[4.4]nonan-3-yl)piperazin-1-yl)-1H-benzo[d]imidazol-2(3H)-one;
(R)-5-(4-(2-(1-oxo-2-oxaspiro[3.4]octan-3-yl)piperazin-1-yl)-1H-benzo[d]imidazol-2(3H)-one;
(S)-5-(4-(2-(1-oxo-2-oxaspiro[3.4]octan-3-yl)piperazin-1-yl)-1H-benzo[d]imidazol-2(3H)-one;
(R)-3-(2-(4-(2-chloropyridin-4-yl)piperazin-1-yl)ethyl)-2-oxaspiro[4.5]decan-1-one;
(S)-3-(2-(4-(2-chloropyridin-4-yl)piperazin-1-yl)ethyl)-2-oxaspiro[4.5]decan-1-one;
(R)-3-{2-[4-(4-Chloro-pyridin-2-yl)-piperazin-1-yl]-ethyl}-2-oxa-spiro[4.5]decan-1-one;
(S)-3-{2-[4-(4-Chloro-pyridin-2-yl)-piperazin-1-yl]-ethyl}-2-oxa-spiro[4.5]decan-1-one;
(R)-2-(4-(2-(1-oxo-2-oxaspiro[4.5]decan-3-yl)ethyl)piperazin-1-yl)isonicotinonitrile;

(S)-2-(4-(2-(1-oxo-2-oxaspiro[4.5]decan-3-yl)ethyl)piperazin-1-yl)isonicotinonitrile;
(R)-3-(2-(4-(4-methoxypyridin-2-yl)piperazin-1-yl)ethyl)-2-oxaspiro[4.5]decan-1-one;
(S)-3-(2-(4-(4-methoxypyridin-2-yl)piperazin-1-yl)ethyl)-2-oxaspiro[4.5]decan-1-one;
(R)-2-(4-(2-(5-oxo-6-oxaspiro[3.4]octan-7-yl)ethyl)piperazin-1-yl)isonicotinonitrile;
(S)-2-(4-(2-(5-oxo-6-oxaspiro[3.4]octan-7-yl)ethyl)piperazin-1-yl)isonicotinonitrile;
(R)-7-(2-(4-(2-chloropyridin-4-yl)piperazin-1-yl)ethyl)-6-oxaspiro[3.4]octan-5-one;
(S)-7-(2-(4-(2-chloropyridin-4-yl)piperazin-1-yl)ethyl)-6-oxaspiro[3.4]octan-5-one;
(R)-3-(2-(4-(2-methyl-1H-benzo[d]imidazol-4-yl)piperazin-1-yl)ethyl)-2-oxaspiro[4.5]decan-1-one;
(S)-3-(2-(4-(2-methyl-1H-benzo[d]imidazol-4-yl)piperazin-1-yl)ethyl)-2-oxaspiro[4.5]decan-1-one;
(R)-5-(2-(4-(4-(trifluoromethyl)phenyl)piperazin-1-yl)ethyl)-dihydro-3,3-dimethylfuran-2(3H)-one;
(S)-5-(2-(4-(4-(trifluoromethyl)phenyl)piperazin-1-yl)ethyl)-dihydro-3,3-dimethylfuran-2(3H)-one;
(R)-dihydro-3,3-dimethyl-5-(2-(4-p-tolylpiperazin-1-yl)ethyl)furan-2(3H)-one;
(S)-dihydro-3,3-dimethyl-5-(2-(4-p-tolylpiperazin-1-yl)ethyl)furan-2(3H)-one;
(R)-3-(2-(4-(4-chloropyridin-2-yl)piperazin-1-yl)ethyl)-2-oxaspiro[4.4]nonan-1-one;
(S)-3-(2-(4-(4-chloropyridin-2-yl)piperazin-1-yl)ethyl)-2-oxaspiro[4.4]nonan-1-one;
(R)-2-(4-(2-(1-oxo-2-oxaspiro[4.4]nonan-3-yl)ethyl)piperazin-1-yl)isonicotinonitrile;
(S)-2-(4-(2-(1-oxo-2-oxaspiro[4.4]nonan-3-yl)ethyl)piperazin-1-yl)isonicotinonitrile;
(R)-3-(2-(4-(4-methoxypyridin-2-yl)piperazin-1-yl)ethyl)-2-oxaspiro[4.4]nonan-1-one;
(S)-3-(2-(4-(4-methoxypyridin-2-yl)piperazin-1-yl)ethyl)-2-oxaspiro[4.4]nonan-1-one;
(R)-3-(2-(4-(2-chloropyridin-4-yl)piperazin-1-yl)ethyl)-2-oxaspiro[4.4]nonan-1-one;
(S)-3-(2-(4-(2-chloropyridin-4-yl)piperazin-1-yl)ethyl)-2-oxaspiro[4.4]nonan-1-one;
(R)-7-(2-(4-(2-hydroxyphenyl)piperazin-1-yl)ethyl)-6-oxaspiro[3.4]octan-5-one;
(S)-7-(2-(4-(2-hydroxyphenyl)piperazin-1-yl)ethyl)-6-oxaspiro[3.4]octan-5-one;
(R)-7-(2-(4-(2-methoxyphenyl)piperazin-1-yl)ethyl)-6-oxaspiro[3.4]octan-5-one;
(S)-7-(2-(4-(2-methoxyphenyl)piperazin-1-yl)ethyl)-6-oxaspiro[3.4]octan-5-one;
(R)-3-(2-(4-(2-hydroxyphenyl)piperazin-1-yl)ethyl)-2-oxaspiro[4.4]nonan-1-one;
(S)-3-(2-(4-(2-hydroxyphenyl)piperazin-1-yl)ethyl)-2-oxaspiro[4.4]nonan-1-one;
(R)-3-(2-(4-(2-methoxyphenyl)piperazin-1-yl)ethyl)-2-oxaspiro[4.4]nonan-1-one;
(S)-3-(2-(4-(2-methoxyphenyl)piperazin-1-yl)ethyl)-2-oxaspiro[4.4]nonan-1-one;
(R)—N-(4-(4-(2-(1-oxo-2-oxaspiro[4.4]nonan-3-yl)ethyl)piperazin-1-yl)phenyl)methanesulfonamide;
(S)—N-(4-(4-(2-(1-oxo-2-oxaspiro[4.4]nonan-3-yl)ethyl)piperazin-1-yl)phenyl)methanesulfonamide;
(R)-3,3-diethyl-dihydro-5-(2-(4-(2-methyl-1H-benzo[d]imidazol-6-yl)piperazin-1-yl)ethyl)furan-2(3H)-one;
(S)-3,3-diethyl-dihydro-5-(2-(4-(2-methyl-1H-benzo[d]imidazol-6-yl)piperazin-1-yl)ethyl)furan-2(3H)-one;
(R)-3,3-diethyl-5-(2-(4-(2-(trifluoromethyl)-1H-benzo[d]imidazol-6-yl)piperazin-1-yl)ethyl)-dihydrofuran-2(3H)-one;
(S)-3,3-diethyl-5-(2-(4-(2-(trifluoromethyl)-1H-benzo[d]imidazol-6-yl)piperazin-1-yl)ethyl)-dihydrofuran-2(3H)-one;
(R)-3,3-diethyl-dihydro-5-(3-(4-p-tolylpiperazin-1-yl)propyl)furan-2(3H)-one;
(S)-3,3-diethyl-dihydro-5-(3-(4-p-tolylpiperazin-1-yl)propyl)furan-2(3H)-one;
(R)-3,3-diethyl-dihydro-5-(3-(4-(pyridin-2-yl)piperazin-1-yl)propyl)furan-2(3H)-one;
(S)-3,3-diethyl-dihydro-5-(3-(4-(pyridin-2-yl)piperazin-1-yl)propyl)furan-2(3H)-one;
(R)-3,3-diethyl-dihydro-5-(3-(4-(2-isopropylphenyl)piperazin-1-yl)propyl)furan-2(3H)-one;
(S)-3,3-diethyl-dihydro-5-(3-(4-(2-isopropylphenyl)piperazin-1-yl)propyl)furan-2(3H)-one;
(S)-dihydro-5-(2-(4-(2-isopropylphenyl)piperazin-1-yl)ethyl)-3,3-dimethylfuran-2(3H)-one;
(R)-dihydro-5-(2-(4-(2-isopropylphenyl)piperazin-1-yl)ethyl)-3,3-dimethylfuran-2(3H)-one;
(S)-3,3-diethyl-dihydro-5-(2-(4-(pyridin-4-yl)piperazin-1-yl)ethyl)furan-2(3H)-one;
and
(R)-3,3-diethyl-dihydro-5-(2-(4-(pyridin-4-yl)piperazin-1-yl)ethyl)furan-2(3H)-one;
or a pharmaceutically acceptable salt form thereof.

2. A composition comprising at least one excipient and at least one compound in an effective amount for providing modulation of 5-hydroxytryptamine receptor 7 activity, wherein the compound is selected from the list consisting of:
(R)-3-{2-[4-(5-Chloro-pyridin-2-yl)-piperazin-1-yl]-ethyl}-2-oxa-spiro[4.5]decan-1-one;
(S)-3-{2-[4-(5-Chloro-pyridin-2-yl)-piperazin-1-yl]-ethyl}-2-oxa-spiro[4.5]decan-1-one;
(R)-3-{2-[4-(1H-Indol-5-yl)-piperazin-1-yl]-ethyl}-2-oxa-spiro[4.5]decan-1-one;
(S)-3-{2-[4-(1H-Indol-5-yl)-piperazin-1-yl]-ethyl}-2-oxa-spiro[4.5]decan-1-one;
(R)-3-{2-[4-(1H-Indol-5-yl)-piperazin-1-yl]-ethyl}-2-oxa-spiro[4.5]decan-1-one;
(S)-3-{2-[4-(1H-Indol-5-yl)-piperazin-1-yl]-ethyl}-2-oxa-spiro[4.5]decan-1-one;
(R)-3-{2-[4-(1H-Indol-5-yl)-piperazin-1-yl]-ethyl}-2-oxa-spiro[4.4]nonan-1-one;
(S)-3-{2-[4-(1H-Indol-5-yl)-piperazin-1-yl]-ethyl}-2-oxa-spiro[4.4]nonan-1-one;
(R)-7-{2-[4-(1H-Indol-5-yl)-piperazin-1-yl]-ethyl}-6-oxa-spiro[3.4]octan-5-one;
(S)-7-{2-[4-(1H-Indol-5-yl)-piperazin-1-yl]-ethyl}-6-oxa-spiro[3.4]octan-5-one;
(R)-3-(2-(4-(-3-amino-4-nitrophenyl)piperazin-1-yl)ethyl)-2-oxaspiro[4.5]decan-1-one;
(S)-3-(2-(4-(-3-amino-4-nitrophenyl)piperazin-1-yl)ethyl)-2-oxaspiro[4.5]decan-1-one;
(R)-5-(4-(2-(1-oxo-2-oxaspiro[4.5]decan-3-yl)ethyl)piperazin-1-yl)-1H-benzo[d]imidazol-2(3H)-one;
(S)-5-(4-(2-(1-oxo-2-oxaspiro[4.5]decan-3-yl)ethyl)piperazin-1-yl)-1H-benzo[d]imidazol-2(3H)-one;
(R)-5-(4-(2-(1-oxo-2-oxaspiro[4.4]nonan-3-yl)piperazin-1-yl)-1H-benzo[d]imidazol-2(3H)-one;
(S)-5-(4-(2-(1-oxo-2-oxaspiro[4.4]nonan-3-yl)piperazin-1-yl)-1H-benzo[d]imidazol-2(3H)-one;
(R)-5-(4-(2-(1-oxo-2-oxaspiro[3.4]octan-3-yl)piperazin-1-yl)-1H-benzo[d]imidazol-2(3H)-one;

(S)-5-(4-(2-(1-oxo-2-oxaspiro[3.4]octan-3-yl)piperazin-1-yl)-1H-benzo[d]imidazol-2(3H)-one;
(R)-3-(2-(4-(2-chloropyridin-4-yl)piperazin-1-yl)ethyl)-2-oxaspiro[4.5]decan-1-one;
(S)-3-(2-(4-(2-chloropyridin-4-yl)piperazin-1-yl)ethyl)-2-oxaspiro[4.5]decan-1-one;
(R)-3-{2-[4-(4-Chloro-pyridin-2-yl)-piperazin-1-yl]-ethyl}-2-oxa-spiro[4.5]decan-1-one;
(S)-3-{2-[4-(4-Chloro-pyridin-2-yl)-piperazin-1-yl]-ethyl}-2-oxa-spiro[4.5]decan-1-one;
(R)-2-(4-(2-(1-oxo-2-oxaspiro[4.5]decan-3-yl)ethyl)piperazin-1-yl)isonicotinonitrile;
(S)-2-(4-(2-(1-oxo-2-oxaspiro[4.5]decan-3-yl)ethyl)piperazin-1-yl)isonicotinonitrile;
(R)-3-(2-(4-(4-methoxypyridin-2-yl)piperazin-1-yl)ethyl)-2-oxaspiro[4.5]decan-1-one;
(S)-3-(2-(4-(4-methoxypyridin-2-yl)piperazin-1-yl)ethyl)-2-oxaspiro[4.5]decan-1-one;
(R)-2-(4-(2-(5-oxo-6-oxaspiro[3.4]octan-7-yl)ethyl)piperazin-1-yl)isonicotinonitrile;
(S)-2-(4-(2-(5-oxo-6-oxaspiro[3.4]octan-7-yl)ethyl)piperazin-1-yl)isonicotinonitrile;
(R)-7-(2-(4-(2-chloropyridin-4-yl)piperazin-1-yl)ethyl)-6-oxaspiro[3.4]octan-5-one;
(S)-7-(2-(4-(2-chloropyridin-4-yl)piperazin-1-yl)ethyl)-6-oxaspiro[3.4]octan-5-one;
(R)-3-(2-(4-(2-methyl-1H-benzo[d]imidazol-4-yl)piperazin-1-yl)ethyl)-2-oxaspiro[4.5]decan-1-one;
(S)-3-(2-(4-(2-methyl-1H-benzo[d]imidazol-4-yl)piperazin-1-yl)ethyl)-2-oxaspiro[4.5]decan-1-one;
(R)-5-(2-(4-(4-(trifluoromethyl)phenyl)piperazin-1-yl)ethyl)-dihydro-3,3-dimethylfuran-2(3H)-one;
(S)-5-(2-(4-(4-(trifluoromethyl)phenyl)piperazin-1-yl)ethyl)-dihydro-3,3-dimethylfuran-2(3H)-one;
(R)-dihydro-3,3-dimethyl-5-(2-(4-p-tolylpiperazin-1-yl)ethyl)furan-2(3H)-one;
(S)-dihydro-3,3-dimethyl-5-(2-(4-p-tolylpiperazin-1-yl)ethyl)furan-2(3H)-one;
(R)-3-(2-(4-(4-chloropyridin-2-yl)piperazin-1-yl)ethyl)-2-oxaspiro[4.4]nonan-1-one;
(S)-3-(2-(4-(4-chloropyridin-2-yl)piperazin-1-yl)ethyl)-2-oxaspiro[4.4]nonan-1-one;
(R)-2-(4-(2-(1-oxo-2-oxaspiro[4.4]nonan-3-yl)ethyl)piperazin-1-yl)isonicotinonitrile;
(S)-2-(4-(2-(1-oxo-2-oxaspiro[4.4]nonan-3-yl)ethyl)piperazin-1-yl)isonicotinonitrile;
(R)-3-(2-(4-(4-methoxypyridin-2-yl)piperazin-1-yl)ethyl)-2-oxaspiro[4.4]nonan-1-one;
(S)-3-(2-(4-(4-methoxypyridin-2-yl)piperazin-1-yl)ethyl)-2-oxaspiro[4.4]nonan-1-one;
(R)-3-(2-(4-(2-chloropyridin-4-yl)piperazin-1-yl)ethyl)-2-oxaspiro[4.4]nonan-1-one;
(S)-3-(2-(4-(2-chloropyridin-4-yl)piperazin-1-yl)ethyl)-2-oxaspiro[4.4]nonan-1-one;
(R)-7-(2-(4-(2-hydroxyphenyl)piperazin-1-yl)ethyl)-6-oxaspiro[3.4]octan-5-one;
(S)-7-(2-(4-(2-hydroxyphenyl)piperazin-1-yl)ethyl)-6-oxaspiro[3.4]octan-5-one;
(R)-7-(2-(4-(2-methoxyphenyl)piperazin-1-yl)ethyl)-6-oxaspiro[3.4]octan-5-one;
(S)-7-(2-(4-(2-methoxyphenyl)piperazin-1-yl)ethyl)-6-oxaspiro[3.4]octan-5-one;
(R)-3-(2-(4-(2-hydroxyphenyl)piperazin-1-yl)ethyl)-2-oxaspiro[4.4]nonan-1-one;
(S)-3-(2-(4-(2-hydroxyphenyl)piperazin-1-yl)ethyl)-2-oxaspiro[4.4]nonan-1-one;
(R)-3-(2-(4-(2-methoxyphenyl)piperazin-1-yl)ethyl)-2-oxaspiro[4.4]nonan-1-one;
(S)-3-(2-(4-(2-methoxyphenyl)piperazin-1-yl)ethyl)-2-oxaspiro[4.4]nonan-1-one;
(R)—N-(4-(4-(2-(1-oxo-2-oxaspiro[4.4]nonan-3-yl)ethyl)piperazin-1-yl)phenyl)methanesulfonamide;
(S)—N-(4-(4-(2-(1-oxo-2-oxaspiro[4.4]nonan-3-yl)ethyl)piperazin-1-yl)phenyl)methanesulfonamide;
(R)-3,3-diethyl-dihydro-5-(2-(4-(2-methyl-1H-benzo[d]imidazol-6-yl)piperazin-1-yl)ethyl)furan-2(3H)-one;
(S)-3,3-diethyl-dihydro-5-(2-(4-(2-methyl-1H-benzo[d]imidazol-6-yl)piperazin-1-yl)ethyl)furan-2(3H)-one;
(R)-3,3-diethyl-5-(2-(4-(2-(trifluoromethyl)-1H-benzo[d]imidazol-6-yl)piperazin-1-yl)ethyl)-dihydrofuran-2(3H)-one;
(S)-3,3-diethyl-5-(2-(4-(2-(trifluoromethyl)-1H-benzo[d]imidazol-6-yl)piperazin-1-yl)ethyl)-dihydrofuran-2(3H)-one;
(R)-3,3-diethyl-dihydro-5-(3-(4-p-tolylpiperazin-1-yl)propyl)furan-2(3H)-one;
(S)-3,3-diethyl-dihydro-5-(3-(4-p-tolylpiperazin-1-yl)propyl)furan-2(3H)-one;
(R)-3,3-diethyl-dihydro-5-(3-(4-(pyridin-2-yl)piperazin-1-yl)propyl)furan-2(3H)-one;
(S)-3,3-diethyl-dihydro-5-(3-(4-(pyridin-2-yl)piperazin-1-yl)propyl)furan-2(3H)-one;
(R)-3,3-diethyl-dihydro-5-(3-(4-(2-isopropylphenyl)piperazin-1-yl)propyl)furan-2(3H)-one;
(S)-3,3-diethyl-dihydro-5-(3-(4-(2-isopropylphenyl)piperazin-1-yl)propyl)furan-2(3H)-one;
(S)-dihydro-5-(2-(4-(2-isopropylphenyl)piperazin-1-yl)ethyl)-3,3-dimethylfuran-2(3H)-one;
(R)-dihydro-5-(2-(4-(2-isopropylphenyl)piperazin-1-yl)ethyl)-3,3-dimethylfuran-2(3H)-one;
(S)-3,3-diethyl-dihydro-5-(2-(4-(pyridin-4-yl)piperazin-1-yl)ethyl)furan-2(3H)-one; and
(R)-3,3-diethyl-dihydro-5-(2-(4-(pyridin-4-yl)piperazin-1-yl)ethyl)furan-2(3H)-one;
or a pharmaceutically acceptable salt form thereof.

* * * * *

UNITED STATES PATENT AND TRADEMARK OFFICE
CERTIFICATE OF CORRECTION

| | |
|---|---|
| PATENT NO. | : 10,544,117 B2 |
| APPLICATION NO. | : 15/510152 |
| DATED | : January 28, 2020 |
| INVENTOR(S) | : Daniel J. Canney et al. |

It is certified that error appears in the above-identified patent and that said Letters Patent is hereby corrected as shown below:

In the Specification

Column 1, delete Lines 19-24
Replace with -- This invention was made with government support under HHSN-271-2008-00025-C awarded by the National Institutes of Health. The government has certain rights in the invention. --

Signed and Sealed this
Sixteenth Day of April, 2024

Katherine Kelly Vidal
*Director of the United States Patent and Trademark Office*